United States Patent
Takasugi

(10) Patent No.: US 9,933,610 B2
(45) Date of Patent: Apr. 3, 2018

(54) OBLIQUE-VIEWING OBJECTIVE OPTICAL SYSTEM AND ENDOSCOPE FOR OBLIQUE VIEWING USING THE SAME

(71) Applicant: OLYMPUS CORPORATION, Hachioji-shi, Tokyo (JP)

(72) Inventor: Yoshiharu Takasugi, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/719,499

(22) Filed: Sep. 28, 2017

(65) Prior Publication Data

US 2018/0017777 A1 Jan. 18, 2018

Related U.S. Application Data

(63) Continuation of application No. PCT/JP2016/081574, filed on Oct. 25, 2016.

(30) Foreign Application Priority Data

Dec. 14, 2015 (JP) .................................. 2015-243128

(51) Int. Cl.
*G02B 3/00* (2006.01)
*G02B 23/24* (2006.01)
(Continued)

(52) U.S. Cl.
CPC ........ *G02B 23/243* (2013.01); *A61B 1/00174* (2013.01); *G02B 5/04* (2013.01);
(Continued)

(58) Field of Classification Search
CPC .... A61B 1/00174; G02B 5/04; G02B 23/243; G02B 13/24; G02B 13/00; G02B 13/04; G02B 9/62
(Continued)

(56) References Cited

U.S. PATENT DOCUMENTS 4,037,938 A    7/1977  Yamashita et al.
4,387,969 A *  6/1983  Nishioka ................ G03B 17/48
                                                    359/726
(Continued)

FOREIGN PATENT DOCUMENTS

JP     51062053 A    5/1976
JP     09010170 A    1/1997
(Continued)

OTHER PUBLICATIONS

International Search Report (ISR) and Written Opinion dated Jan. 17, 2017 issued in International Application No. PCT/JP2016/081574.

*Primary Examiner* — James Greece
(74) *Attorney, Agent, or Firm* — Holtz, Holtz & Volek PC

(57) ABSTRACT

The oblique-viewing objective optical system includes a front-side lens group having a negative refractive power, an optical path converting element, an aperture stop, and a rear-side lens group having a positive refractive power. The front-side lens group includes a first lens and a second lens, and the rear-side lens group includes a third lens and a cemented lens which includes a positive biconvex lens and a meniscus-shape negative lens. The first lens is a negative lens having a concave surface directed toward an image-plane side, and the second lens is a single lens having a convex surface directed toward the image-plane side or a cemented lens, and the third lens is a positive lens. The following conditional expressions (1) to (3) are satisfied:

$$1.6 < D1/f < 4.7 \quad (1),$$

$$1.0 < D2/f < 3.3 \quad (2), \text{ and}$$

$$9.0 < L/f < 31.0 \quad (3).$$

9 Claims, 38 Drawing Sheets

(51) Int. Cl.
  *A61B 1/00* (2006.01)
  *G02B 5/04* (2006.01)
  *G02B 23/26* (2006.01)
  *H04N 5/225* (2006.01)

(52) U.S. Cl.
  CPC ............ *G02B 23/26* (2013.01); *H04N 5/2254* (2013.01); *H04N 2005/2255* (2013.01)

(58) Field of Classification Search
  USPC .................. 359/737, 754, 755, 756, 761
  See application file for complete search history.

(56) References Cited

U.S. PATENT DOCUMENTS

| | | | |
|---|---|---|---|
| 4,493,537 A * | 1/1985 | Nakahashi | G02B 13/04 359/740 |
| 4,976,522 A * | 12/1990 | Igarashi | G02B 15/177 359/680 |
| 5,916,148 A | 6/1999 | Tsuyuki | |
| 5,936,778 A | 8/1999 | Miyano et al. | |
| 6,206,825 B1 | 3/2001 | Tsuyuki | |
| 2004/0125469 A1 | 7/2004 | Miyano | |
| 2010/0076268 A1 | 3/2010 | Takasugi et al. | |
| 2012/0147164 A1 | 6/2012 | Sasamoto | |
| 2012/0224268 A1 | 9/2012 | Takato | |
| 2014/0092225 A1 | 4/2014 | Sasamoto | |

FOREIGN PATENT DOCUMENTS

| | | |
|---|---|---|
| JP | 10111454 A | 4/1998 |
| JP | 10260348 A | 9/1998 |
| JP | 3359092 B2 | 12/2002 |
| JP | 3385090 B2 | 3/2003 |
| JP | 4265909 B2 | 5/2009 |
| JP | 4556382 B2 | 10/2010 |
| JP | 5558058 B2 | 7/2014 |
| WO | 2011145505 A1 | 11/2011 |
| WO | 2012008312 A1 | 1/2012 |
| WO | 2013042456 A1 | 3/2013 |

* cited by examiner

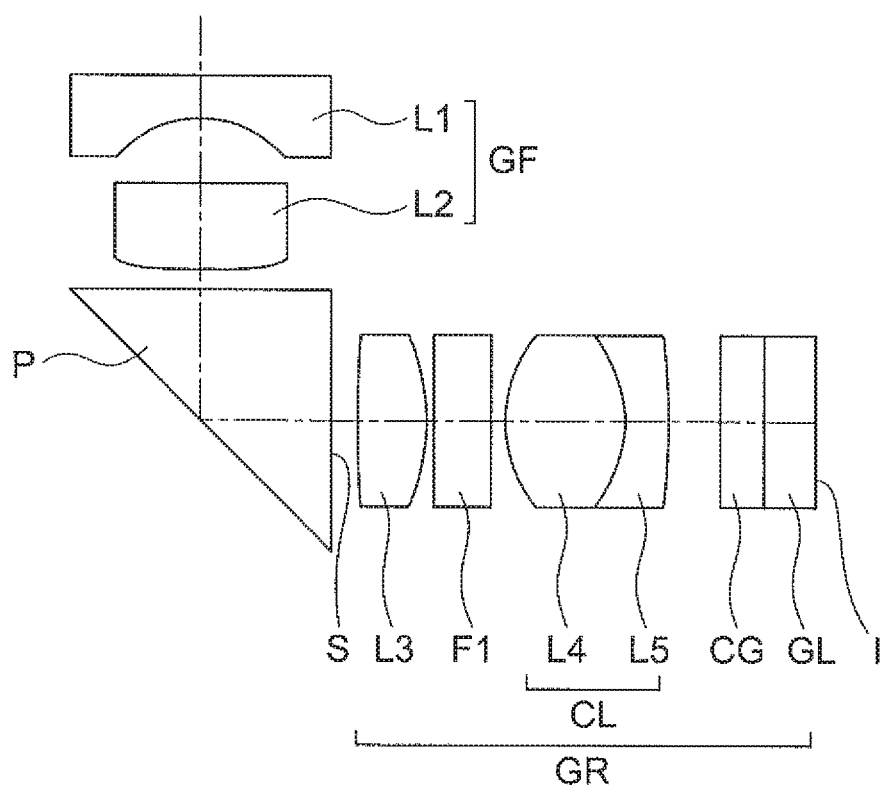

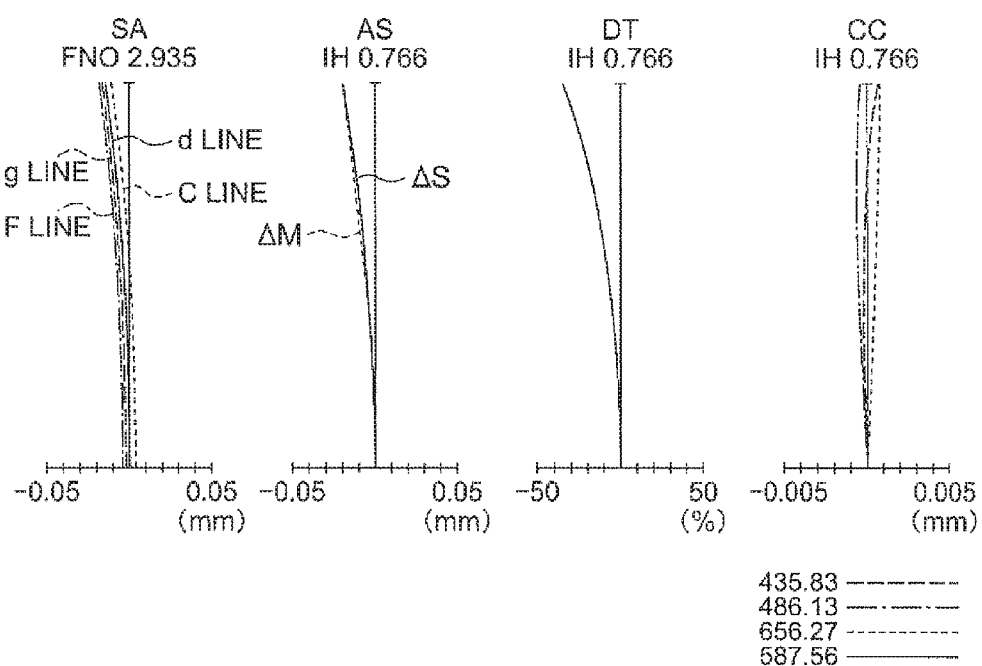

FIG. 8A
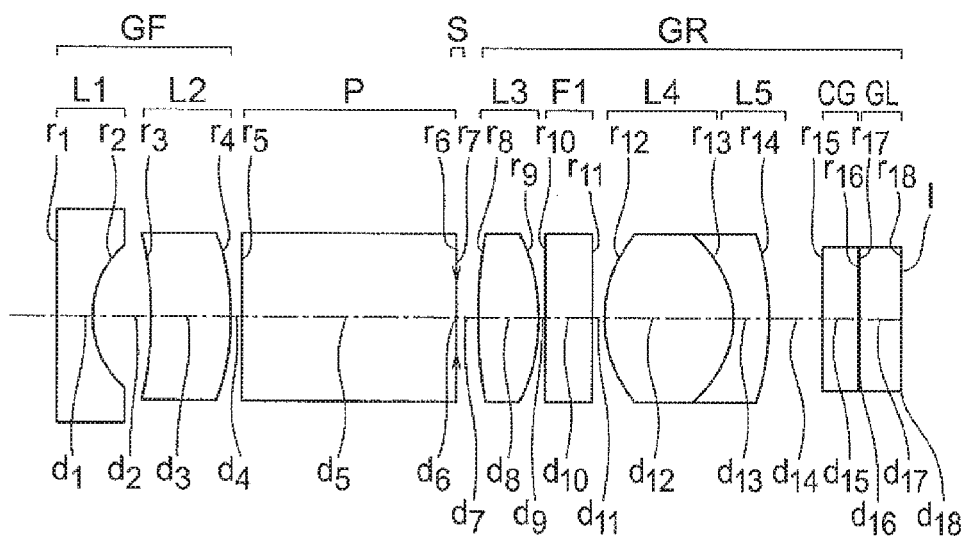
FIG. 8B
SA
FNO 2.969
FIG. 8C
AS
IH 0.778
FIG. 8D
DT
IH 0.778
FIG. 8E
CC
IH 0.778
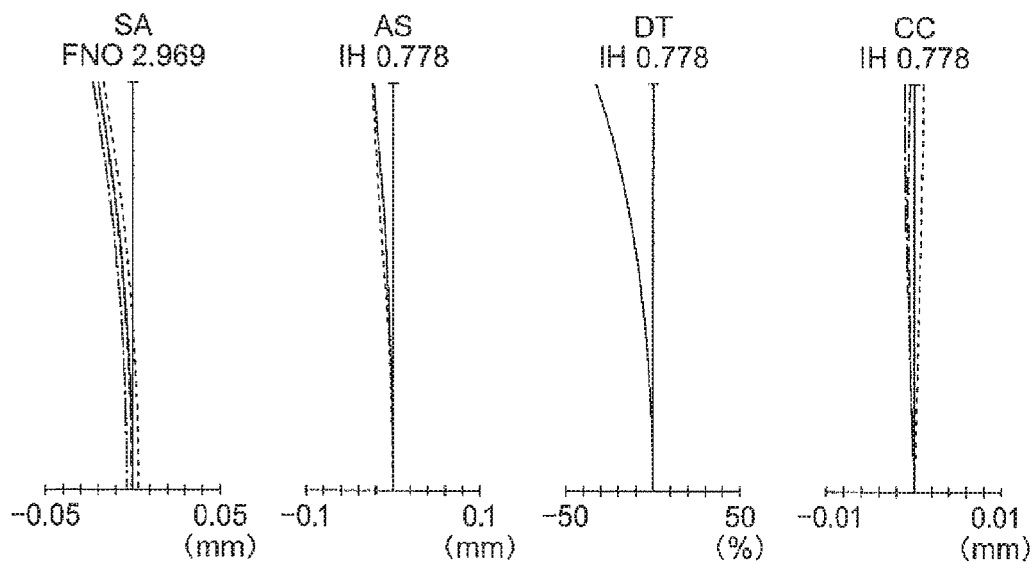

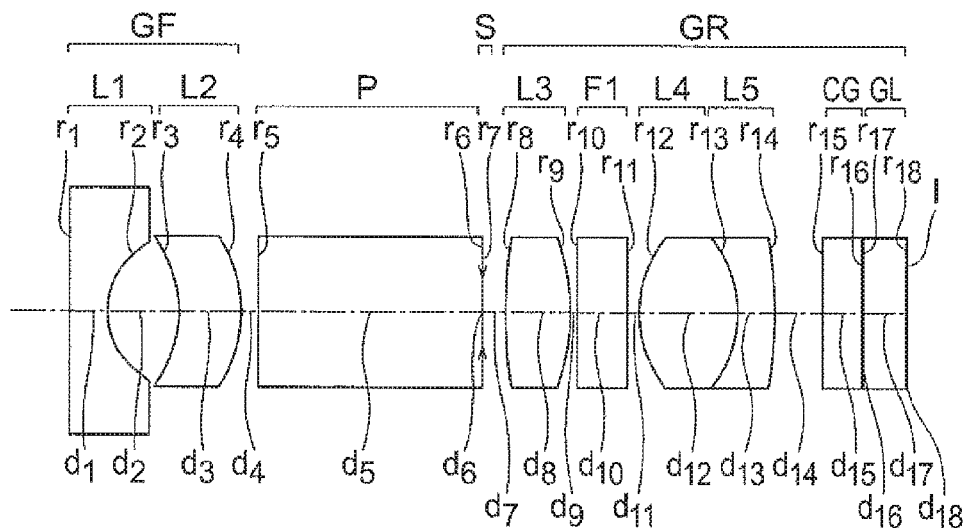
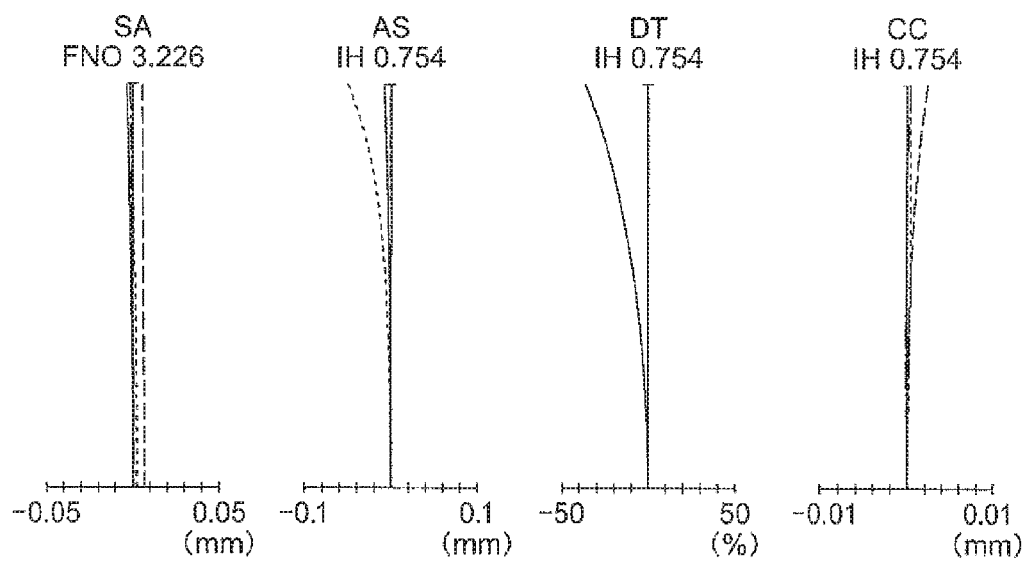

OBLIQUE-VIEWING OBJECTIVE OPTICAL SYSTEM AND ENDOSCOPE FOR OBLIQUE VIEWING USING THE SAME

CROSS-REFERENCE TO RELATED APPLICATION

The present application is a continuation application of PCT/JP2016/081574 filed on Oct. 25, 2016 which is based upon and claims the benefit of priority from Japanese Patent Application No. 2015-243128 filed on Dec. 14, 2015; the entire contents of which are incorporated herein by reference.

BACKGROUND OF THE INVENTION

Field of the Invention

The present invention relates to an oblique-viewing objective optical system provided with an optical path converting element, and an endoscope for oblique viewing using the same.

Description of the Related Art

In recent years, in image pickup elements such as a CCD (Charged Coupled Devices) and a C-MOS (Complementary Metal Oxide Semiconductor), due to the progress in microfabrication technology, refining of pixels and small-sizing of an element have been advancing. Especially, recently, image pickup elements having extremely fine pixels such as an image pickup element with a pixel pitch of approximately 1 μm to 2 μm have been manufactured. Thus, the image pickup elements in recent years have a large number of pixels and a small size as compared to former image pickup elements.

Moreover, when a lens outer-diameter and an overall length of an objective optical system are made small-sized, it becomes difficult to make a light ray emerged from the objective optical system be incident perpendicularly on a light-receiving surface of an image pickup element. In this case, the light ray is incident obliquely (hereinafter, referred to as 'oblique incidence') on the light-receiving surface. Therefore, image pickup elements such as a CCD and a C-MOS of recent years have been designed on the premise that an optimum incidence of a light ray on the light-receiving surface is oblique incidence. In such manner, the image pickup elements in recent years have an oblique-incidence characteristic.

By using the image pickup element with a large number of pixels and small-size in an endoscope, it is possible to achieve a high-quality image and thinning of an endoscope diameter. With this, an objective optical system having a high performance and small-size has been sought for an objective optical system for endoscope. An optical system with a high performance is an optical system with a high resolving power, and in which an aberration is corrected favorably.

When the pixel pitch becomes as small as 1 μm, in a case in which an F-number of an optical system is large, an optical performance is degraded due to an effect of diffraction. For such reason, an optical system to be used for an image pickup element having a small pixel pitch has to be an optical system with a small F-number. However, when the F-number becomes small, a diameter of a light beam passing through the optical system becomes thick. Therefore, when the F-number is made small, it becomes difficult to carry out an aberration correction favorably.

In an optical system used in an image pickup element having a small pixel pitch, with the narrowing of the pixel pitch, each aberration has to be corrected such that an amount of occurrence thereof becomes extremely small. For instance, with regard to an amount of a transverse aberration, the amount of aberration has to be kept to a level of several times of the pixel pitch, or in other words, about few μm, or not more than 10 μm.

When an attempt is made to correct favorably an aberration of an optical system to such level, the number of lenses of the optical system becomes large. However, when the number of lenses is increased excessively, the overall length of the optical system becomes long. Furthermore, when the overall length of the optical system becomes long, since a height of a light ray passing through a lens becomes high, an outer diameter of the lens also becomes large. In an endoscope, an optical system of a small size is sought. Therefore, an objective optical system has to be arranged such that a size applicable to the endoscope and a high imaging performance are secured while suppressing the increase in the number of lenses as much as possible.

Moreover, as an objective optical system for endoscope, an oblique-viewing objective optical system is available. In the oblique viewing objective optical system, a front viewing, a side viewing, and a rear viewing are carried out.

FIG. 1 is an example of a conventional oblique-viewing objective optical system. An oblique-viewing optical system 1 is an oblique-viewing optical system that carries out the side viewing. The oblique-viewing objective optical system 1 includes a front-side lens group 2, a prism 3, and a rear-side lens group 4. In the oblique-viewing objective optical system 1, due to the prism 3, an optical axis of the front-side lens group 2 and an optical axis of the rear-side lens group 4 are orthogonal.

FIG. 2 is another example of the conventional oblique-viewing objective optical system. An oblique-viewing optical system 5 is an oblique-viewing optical system that carries out the front viewing. An oblique-viewing objective optical system 5 includes a front-side lens group 6, a prism 7, and a rear-side lens group 8. In the oblique-viewing objective optical system. 5, due to the prism 7, an optical axis of the front-side lens group 6 and an optical axis of the rear-side lens group intersect.

As shown in FIG. 1 and FIG. 2, in the oblique-viewing objective optical system, an optical path converting element with a large path length in glass is disposed in the optical system. Therefore, especially in the oblique-viewing objective optical system, a large space for disposing an optical path converting element such as a prism is necessary. Consequently, in the oblique-viewing objective optical system, an overall length of the optical system becomes long as compared to a direct-viewing objective optical system. Thus, since an oblique-viewing objective optical system tends to be large-sized as compared to a direct-viewing objective optical system, further small-sizing has been sought in the oblique-viewing objective optical system.

In Japanese Patent Application Laid-open Publication No. Sho 51-62053, Japanese Patent No. 3385090, and Japanese Patent No. 5558058 Publication, oblique-viewing objective optical systems have been disclosed. Moreover, in Japanese Patent Application Laid-open Publication No. Hei 10-111454, Japanese Patent No. 3359092 Publication, International Unexamined Patent Application Publication No. 2012/008312, Japanese Patent No. 4556382 Publication, Japanese Patent Application Laid-open Publication No. Hei 10-260348, and Japanese Patent No. 4265909 Publication, direct-viewing objective optical systems have been disclosed.

In Japanese Patent Application Laid-open Publication No. Sho 51-62053, an oblique-viewing objective optical system and a direct-viewing objecting optical system have been disclosed. The oblique-viewing objective optical system includes a front-group diverging lens system which includes a negative lens, a rear-group converging lens system, and a prism which is disposed between the front-group diverging lens system and the rear-group converging lens system. No prism has been disposed in the direct-viewing objective optical system. Consequently, in the direct-viewing objective optical system, a front-group converging lens system and a rear-group converging lens system are disposed to be separated (with a wide space between lenses).

Moreover, these objective optical systems are optical systems supposed to be used in an image fiber. Therefore, in these objective optical systems, an arrangement is made such a light ray emerged from the objective optical system is incident almost perpendicularly on an end surface of incidence of a fiber.

An oblique-viewing objective optical system disclosed in Japanese Patent No. 3385090 includes a first lens group which includes one negative lens, a prism which is a reflecting member, and a second lens group having a positive refractive power. In this oblique-viewing objective optical system, for correcting a chromatic aberration, a glass material with a small dispersion (a glass material for which Abbe number is large) has been used for the prism and the negative lens in the first lens group.

An oblique-viewing objective optical system disclosed in Japanese Patent No. 5558058 Publication includes a front-side lens group having a positive refractive power, a prism which is a visual-field direction converting element, and a rear-side lens group having a positive refractive power. The front-side lens group includes a negative lens and a positive lens. The rear-side lens group includes a cemented lens.

An objective optical system disclosed in Japanese Patent Application Laid-open Publication No. Hei 10-111454 is a direct-viewing objective optical system. This direct-viewing objective optical system includes a first lens group having a negative refractive power, a second lens group having a negative refractive power, a third lens group having a positive refractive power, and a fourth lens group having a positive refractive power.

An objective optical system disclosed in Japanese Patent No. 3359092 Publication is a direct-viewing objective optical system. This direct-viewing objective optical system includes a first group which includes a negative lens, a second group which includes a positive single lens, and a rear group. The rear group includes a positive single lens, and a cemented lens of a positive lens and a negative lens.

An objective optical system disclosed in International Unexamined Patent Application Publication No. 2012/008312 is a direct-viewing objective optical system, and includes a negative lens, a positive meniscus lens or a cemented lens having a positive refractive power, a positive lens, and a cemented lens.

An objective optical system disclosed in Japanese Patent No. 4556382 Publication is a direct-viewing objective optical system. This direct-viewing objective optical system includes a front group having a negative refractive power and a rear group having a positive refractive power. The front group includes a negative lens and a lens group having a weak refractive power. The rear group includes a positive lens and a cemented lens.

In an objective optical system disclosed in Japanese Patent Application Laid-open Publication No. Hei 10-260348, an optical path converting prism having a long path length in glass has been disposed on an image-plane side. However, this objective optical system is a direct-viewing objective optical system. This direct-viewing objective optical system includes a front-group diverging lens system which includes two negative lenses, and a rear-group converging lens.

In an objective optical system disclosed in Japanese Patent No. 4265909 Publication, an optical path converting prism having a long path length in glass has been disposed on an image-plane side. However, this objective optical system is a direct-viewing objective optical system. This direct-viewing objective optical system includes a first lens having a negative refractive power, a cemented lens having a positive refractive power in which a second lens and a third lens are cemented, a fourth lens having a positive refractive power, and a cemented lens having a positive refractive power in which a fifth lens having a positive refractive power and a sixth lens having a negative refractive power are cemented.

SUMMARY OF THE INVENTION

An oblique-viewing objective optical system of the present invention comprises in order from an object side,
 a front-side lens group having a negative refractive power,
 an optical path converting element,
 an aperture stop, and
 a rear-side lens group having a positive refractive power, wherein
 the front-side lens group includes a first lens and a second lens, and
 the rear-side lens group includes a third lens, and a cemented lens having a positive refractive power, and
 the first lens is a negative lens having a concave surface directed toward an image-plane side, and
 the second lens is a single lens having a convex surface directed toward the image-plane side or a cemented lens, and
 the third lens is a positive lens, and
 the cemented lens in the rear-side lens group includes a positive lens which is a biconvex lens, and a negative lens having a meniscus shape, and
 the following conditional expressions (1) to (3) are satisfied:

$$1.6 < D1/f < 4.7 \tag{1},$$

$$1.0 < D2/f < 3.3 \tag{2, and}$$

$$9.0 < L/f < 31.0 \tag{3}$$

where,
 D1 denotes an air-conversion length from an image-side surface of a lens positioned nearest to an image plane in the front-side lens group up to the aperture stop,
 D2 denotes an air-conversion length from an image-side surface of a rearmost lens in the rear-side lens group up to an image plane,
 L denotes an overall length of the oblique-viewing objective optical system, and
 f denotes a focal length of the overall oblique-viewing objective optical system.

Moreover, an endoscope for oblique viewing of the present invention comprises,
 the oblique-viewing objective optical system described above.

BRIEF DESCRIPTION OF THE DRAWINGS

FIG. 3 is a diagram showing in cross-section, an arrangement of an oblique-viewing objective optical system of the present embodiment;

FIG. 5A is a diagram showing in cross-section, an arrangement of an oblique-viewing objective optical system according to an example 1, and FIG. 5B, FIG. 5C, FIG. 5D, and FIG. 5E are aberration diagrams of the example 1;

FIG. 8A is a diagram showing in cross-section, an arrangement of an oblique-viewing objective optical system according to an example 4, and FIG. 8B, FIG. 8C, FIG. 8D, and FIG. 8E are aberration diagrams of the example 4;

FIG. 26A is a diagram showing in cross-section, an arrangement of an oblique-viewing objective optical system according to an example 22, and FIG. 26B, FIG. 26C, FIG. 26D, and FIG. 26E are aberration diagrams of the example 22;

DETAILED DESCRIPTION OF THE INVENTION

Figure 1:
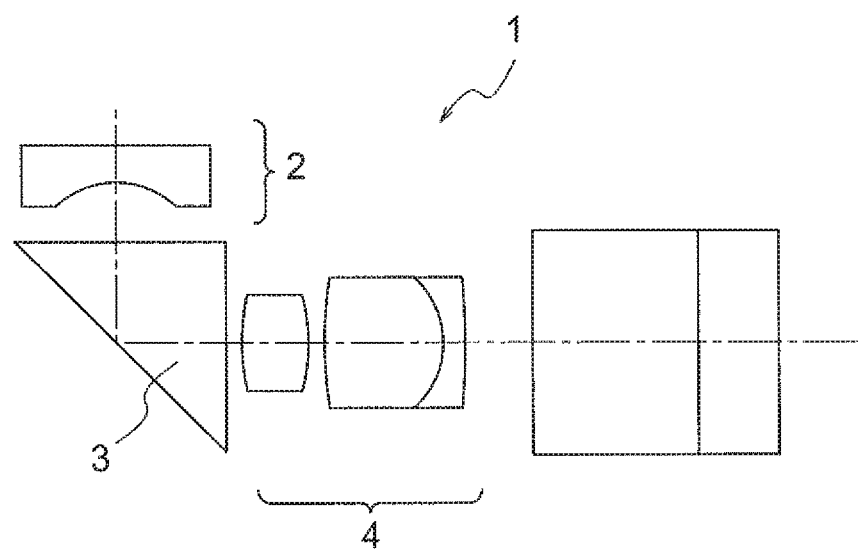
FIG. 1 is a diagram showing a conventional oblique-viewing objective optical system.
Figure 2:
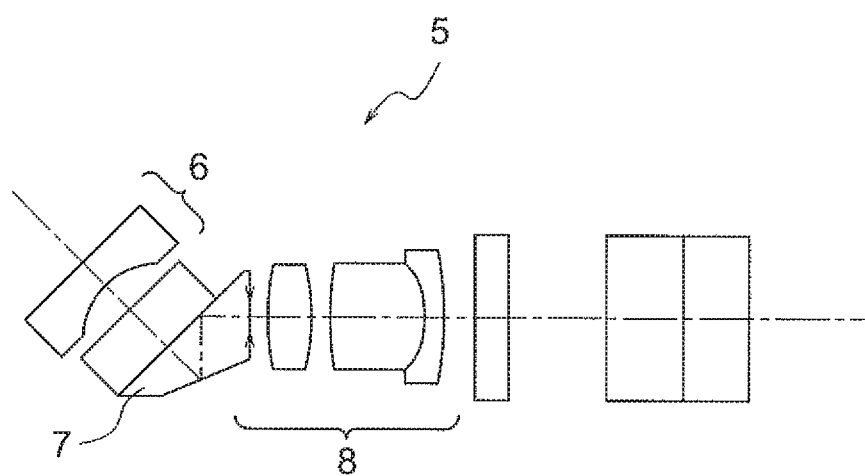
FIG. 2 is a diagram showing another conventional oblique-viewing objective optical system.

Reasons for adopting such arrangements and effects thereof in an oblique-viewing objective optical system and an endoscope for oblique viewing using the same according to the present embodiment, will be described below by referring to the accompanying diagrams. However, the present invention is not restricted to the oblique-viewing objective optical system and the endoscope for oblique viewing using the same according to the following embodiment.

The oblique-viewing objective optical system of the present embodiment includes in order from an object side, a front-side lens group having a negative refractive power, an optical path converting element, an aperture stop, and a rear-side lens group having a positive refractive power. The front-side lens group includes a first lens and a second lens, and the rear-side lens group includes a third lens and a cemented lens having a positive refractive power. The first lens is a negative lens having a concave surface directed toward an image-plane side, and the second lens is a single lens having a convex surface directed toward the image-plane side or a cemented lens. The third lens is a positive lens, and the cemented lens includes a positive lens which is a biconvex lens, and a negative lens having a meniscus shape.

By disposing the optical path converting element near the aperture stop, or in other words, on the object side of the aperture stop or on the image side of the aperture stop, it is possible to suppress a height of a light ray at the optical path converting element to be low. As a result, it is possible to make a size of the optical path converting element small.

However, when the optical path converting element is disposed on the image side of the aperture stop, a distance from the aperture stop up to an image plane becomes longer than at least a path length in glass of the optical path converting element. Consequently, a light ray emerged from the oblique-viewing objective optical system becomes almost perpendicular with respect to a light-receiving surface of an image pickup element. Therefore, an angle of the light ray emerged from the oblique-viewing objective optical system does not become an angle that satisfies oblique incidence characteristic of the image pickup element. As a result, unevenness of brightness and unevenness in color occur in a peripheral portion of image.

Moreover, in assembling of the oblique-viewing objective optical system, focus adjustment is to be carried out. Therefore, when an attempt is made to satisfy forcedly the oblique incidence characteristic of the image pickup element, a distance necessary for the focus adjustment is inadequate. Moreover, since the light ray is to be bent forcedly according to the oblique incidence characteristic, an aberration occurs. As a result, an optical performance is degraded remarkably. The 'focus adjustment' in the following description refers to a focus adjustment at the time of assembling.

Therefore, in the oblique-viewing objective optical system according to the present embodiment, the optical path converting element is disposed on the object side of the aperture stop. Accordingly, since it is possible to shorten a distance from the aperture stop up to the image plane, the angle of a light ray emerging from the oblique-viewing objective optical system can be let to be an angle that satisfies the oblique incidence characteristic of the image pickup element comparatively easily.

However, when the distance from the aperture stop up to the image plane is made too short, a space necessary for the focus adjustment becomes inadequate. Furthermore, it is not possible to dispose various optical elements between the aperture stop and the image plane. The various optical elements are optical elements other than lenses and optical path converting element. Various optical elements include, an infra-red cutting filter, a color-temperature conversion filter, a laser cutting filter, and a cover glass provided to the image pickup element.

When it is not possible to dispose the various optical elements between the aperture stop and the image plane, the various optical elements are to be disposed on the object side of the aperture stop. However, when such an arrangement is made, a length of a lens system disposed on the object side of the aperture stop becomes long. Consequently, since a height of a light ray in this lens system becomes high, a lens outer-diameter becomes large. As a result, the oblique-viewing objective optical system becomes large in size.

In the oblique-viewing objective optical system of the present embodiment, the optical path converting element is disposed on the object side of the aperture stop, and also an arrangement is made such that the distance from the aperture stop up to the image plane does not become excessively short. Consequently, it is possible to dispose the various optical elements on the image-plane side of the aperture stop. Accordingly, it is possible to dispose lenses, the optical path converting element, and the various optical elements in a balanced manner on two sides of the aperture stop. As a result, it is possible to suppress the objective optical system from becoming large-sized.

As mentioned above, in an objective optical system to be used in an image pickup element having a small pixel pitch, the F-number of the optical system has to be small. However, when the F-number is made small, an aperture of the objective optical system becomes large. In this case, aberrations related to a size of the aperture of the optical system, particularly, a spherical aberration and a coma, become large. As a result, an imaging performance of the optical system is degraded remarkably.

Furthermore, for using in an image pickup element having a small pixel pitch, the optical system has to be a high-performance optical system. For this, regarding aberrations such as the spherical aberration, the coma, and a chromatic aberration, it is necessary to make a correction such that an amount of aberration that occurs becomes small.

Moreover, an objective optical system for endoscope is an optical system having a small size and a wide angle of view, and a back focus longer as compared to the focal length. For such reason, in an objective optical system for endoscope, an arrangement of retro focus type is adopted in many cases. In the arrangement of retro focus type, an arrangement of refractive power is in order of a negative refractive power and a positive refractive power from an object side.

For widening an angle in particular, it is necessary to make the negative refractive power of the object side large. However, when the negative refractive power of the object side is made large for widening the angle, an aberration occurs. Besides, an effect of the aberration that occurs is large.

Normally, by adjusting the positive refractive power of the image-plane side, an aberration balance is let to be similar to an aberration balance before making the negative refractive power of the object side large. However, when an attempt is made to make the optical system a high-performance optical system, it is necessary to carryout a more favorable aberration correction by increasing a lens arrangement (the number of lenses).

At this time, a lens is to be disposed on the image-plane side near the negative lens. By making such arrangement, even when an aberration occurs due to making the negative refractive power of the object side large, it is possible to reduce an effect of the aberration that occurs.

In the oblique-viewing objective optical system of the present embodiment, the front-side lens group having a negative refractive power is disposed on the object side of the aperture stop. The front-side lens group includes the first lens and the second lens. Moreover, the rear-side lens group having a positive refractive power is disposed on the image-plane side of the aperture stop. The rear-side lens group includes the third lens, and the cemented lens having a positive refractive power.

The first lens is a negative lens and the third lens is a positive lens. Thus, an arrangement of retro focus type is realized by the first lens and the third lens.

The first lens is positioned nearest to object. In an objective optical system to be used in endoscope, an object-side surface of the first lens is a plane surface in many cases. The following (I) and (II) are the main reasons for this. (I) It is possible to lower a probability of damage of a lens surface. (II) Since water droplets are not susceptible to be accumulated on a peripheral portion of a lens surface, there is no narrowing of an observation range.

In the objective optical system for endoscope, it is necessary to make large an angle of view for observing a wide range. For this, it is necessary to make the first lens to be a negative lens having a large refractive power. When an object-side surface of the first lens is made a plane surface, for achieving the negative refractive power, an image-side surface of the second lens has to be a surface with a concave surface directed toward the image-plane side. Moreover, to achieve a large negative refractive power, the image-side surface of the second lens has to be a lens surface having an extremely large refractive power, or in other words, a lens surface having a small radius of curvature.

Since a light ray is bent substantially at a lens surface having a large refractive power, a large aberration occurs by any means. Particularly, when the F-number becomes small, a diameter of a light beam passing through a lens becomes large. When the diameter of a light beam becomes large, a height of a light ray passing through the optical system becomes high. As a result, an amount of aberration which occurs, increases. In such manner, an effect on aberration when the negative refractive power of the first lens is made large becomes more remarkable as the angle of view is made wider and the F-number is made smaller.

Therefore, by disposing the second lens in the front-side lens group, an effect of the increase in the negative refractive power of the first lens on aberration has been reduced. Specifically, the second lens is to be disposed near the image-plane side of the first lens, to be facing the first lens.

Furthermore, the second lens is to be disposed such that a convex surface is directed toward the image-plane side. An image-side surface of the first lens is a lens surface having a concave surface directed toward the image-plane side. Therefore, the second lens is disposed to be facing the image-side surface of the first lens such that a convex surface of the second lens is directed toward the image-plane side. In the second lens, at least one of the two lens surfaces is a convex lens surface. The second lens may be disposed such that the convex lens surface is made to be a lens surface on the image-plane side.

By making such arrangement, it is possible to bend a light ray in a direction opposite to a direction in which a light ray is bent by the image-side surface of the first lens. As a result, it is possible to correct various aberrations favorably. Therefore, such lens arrangement is effective in aberration correction.

As described above, in the oblique-viewing objective optical system of the present embodiment, the first lens is disposed such that a concave surface is directed toward the image-plane side, and the second lens is disposed such that the convex surface is directed in the opposite direction of the concave surface, or in other words, disposed such that the convex surface is directed toward the image-plane side. In such manner, by providing lens surfaces having an effect of bending a light ray in the opposite directions respectively, an aberration is corrected favorably.

Moreover, it is desirable that the cemented lens in the rear-side lens group includes in order from the object side, the positive lens and the negative lens. By making such arrangement, it is possible to make the oblique-viewing objective optical system small-sized. Moreover, it is possible to let an angle of a light ray that emerges from the oblique-viewing objective optical system to be an angle that satisfies the oblique incidence characteristic of the image pickup element.

When the cemented lens includes in order from the object side, the negative lens and the positive lens, since a height of a light ray at the cemented lens becomes high, an outer diameter of the lens becomes large. Consequently, a workability of the lens is degraded. Moreover, an outer diameter, even as the overall oblique-viewing objective optical system, becomes large.

Furthermore, since a light ray is bent by an effect of the positive lens disposed on the image side, a light ray that emerges from the oblique-viewing objective optical system becomes almost perpendicular to the light-receiving surface of the image pickup element. As a result, it becomes difficult to make an angle of the light ray emerging from the oblique-viewing objective optical system to be an angle that satisfies the oblique incidence characteristic of the image pickup element. When an attempt is made to let the angle that satisfies the oblique incidence characteristic forcedly, since the light ray is bent substantially at the cemented lens surface, an aberration occurs. Consequently, an optical performance is degraded.

The oblique-viewing objective optical system of the present embodiment has the abovementioned arrangement, and the following conditional expressions (1), (2), and (3) are satisfied:

$$1.6 < D1/f < 4.7 \quad (1),$$

$$1.0 < D2/f < 3.3 \quad (2), \text{ and}$$

$$9.0 < L/f < 31.0 \quad (3)$$

where,

D1 denotes an air-conversion length from an image-side surface of a lens positioned nearest to an image plane in the front-side lens group up to the aperture stop, D2 denotes an air-conversion length from an image-side surface of a rearmost lens in the rear-side lens group up to an image plane, L denotes an overall length of the oblique-viewing objective optical system, and f denotes a focal length of the overall oblique-viewing objective optical system.

Conditional expressions (1), (2), and (3) are conditional expressions in which a specific length of the oblique-viewing objective optical system is regulated. These conditional expressions, in particular, are conditional expressions related to an oblique-viewing objective optical system which is necessary for small-sizing and thinning of diameter of an endoscope front-end portion (hereinafter, referred to as 'front-end portion').

Conditional expression (1) is a conditional expression which regulates the air-conversion length from the image-side surface of the lens positioned nearest to the image plane in the front-side lens group up to the aperture stop. For instance, in an example 1 that will be described later, D1 is to be calculated by the following formula.

$$D1 = d4 + d5/n5 + d6$$

In a case of falling below a lower limit value of conditional expression (1), it becomes difficult to secure adequately a space for disposing the optical path converting element having the optimum shape of outer diameter. Consequently, shading of a light ray occurs in the optical path converting element. Moreover, by a light ray being incident on a portion other than an optical surface of the optical path converting element, there is a possibility of a flare occurring in an image.

Moreover, the overall length of the front-side lens group becomes short. At the time of assembling, the front-side lens group of the objective optical system is held by jigs and tools. When the overall length of the front-side lens group becomes short, a portion to be held by the jigs and tools becomes small. Consequently, the optical system cannot be held stably by the jigs and tools, thereby making it difficult to carry out assembling and focus adjustment with high accuracy. Furthermore, it becomes difficult to carry out installation and fixing of an imaging system to the endoscope front-end portion with high accuracy.

In a case of exceeding an upper limit value of conditional expression (1), the space for disposing the optical path converting element can be secured adequately but, a path length in glass from the first lens up to the aperture stop becomes excessively long. In this case, since a light-ray height at the first lens becomes high, an outer diameter of the first lens becomes large. With this, the oblique-viewing objective optical system becomes large-sized. Furthermore, with the oblique-viewing objective optical system becoming large-sized, an outer diameter of an endoscope on which it is to be mounted, becomes large.

Conditional expression (2) is a conditional expression which regulates the air-conversion length from the image-side surface of the rearmost lens in the rear-side lens group up to the image plane. Here, the rearmost lens refers to a lens having a refractive power. Therefore, a power lens or a plane-parallel plat filter such as a color filter is not a rearmost lens. For instance, in the example 1 that will be described later, D2 is calculated by the following formula.

$$D2 = d14 + d15/n15 + d16/n16 + d17/n17 + d18$$

In a case of falling below a lower limit value of conditional expression (2), a distance from the rearmost lens up to the image plane becomes excessively narrow. In this case, since a distance between the image pickup element and the oblique-viewing objective optical system becomes excessively narrow, adequate focus adjustment cannot be carried out at the time of assembling the oblique-viewing objective optical system.

In a case of exceeding an upper limit value of conditional expression (2), since it is possible to secure adequately a distance from the rearmost lens up to the image plane, the focus adjustment is possible. However, since the distance from the rearmost lens up to the image plane becomes excessively long, the objective optical system becomes large-sized.

Furthermore, when the oblique-viewing objective optical system is installed on the endoscope front-end portion, the oblique-viewing objective optical system and the image pickup element (hereinafter, referred to as 'imaging system') become susceptible to interfere with other members. In order to avoid this interference, it is necessary to provide a clearance around the imaging system inside the front-end portion. When the clearance is provided, the overall front-end portion becomes large-sized.

Conditional expression (3) is a conditional expression which regulates the overall length of the oblique-viewing objective optical system. Conditional expression (3) is a condition for optimizing the overall length of the oblique-viewing objective optical system while facilitating a balance of achieving high performance and small-sizing of the optical system.

For small-sizing the endoscope, it is necessary to make the objective optical system small. In a case of falling below a lower limit value of conditional expression (3), since the overall length of the optical system becomes excessively small, a space for disposing the optical path converting element of an appropriate diameter cannot be secured. Moreover, when the overall length of the objective optical system becomes excessively short, a lens arrangement necessary for securing a favorable optical performance cannot be made. Moreover, since it becomes difficult to secure a space necessary for the focus adjustment, a desired depth of field cannot be achieved.

In a case of exceeding an upper limit value of conditional expression (3), it is possible to secure adequately a space for disposing the optical path converting element and lenses. However, since the overall length of the optical system becomes long, an image-ray height in the optical system becomes high. As a result, the lens outer diameter becomes large. Moreover, with the lens outer diameter becoming large, the front-end portion also becomes large.

In the oblique-viewing objective optical system of the present embodiment, it is preferable that the following conditional expression (4) be satisfied:

$$1.0 < D1/D2 < 2.5 \quad (4)$$

where,

D1 denotes the air-conversion length from the image-side surface of the lens positioned nearest to the image plane in the front-side lens group up to the aperture stop, and D2 denotes the air-conversion length from the image-side surface of the rearmost lens in the rear-side lens group up to the image plane.

Conditional expression (4) is a conditional expression which regulates the air-conversion length from the image-side surface of the lens positioned nearest to the image plane in the front-side lens group up to the aperture stop, and the air-conversion length from the image-side surface of the rearmost lens in the rear-side lens group up to the image plane. By satisfying conditional expression (4), it is possible to optimize the balance of the two air-conversion lengths D1 and D2. As a result, it is possible to optimize the size of the optical system.

In a case of falling below a lower limit value of conditional expression (4), the air-conversion length from the image-side surface of the lens positioned nearest to the image plane in the front-side lens group up to the aperture stop becomes excessively short. Consequently, an optical path converting element having the optimum shape of outer diameter cannot be disposed. Or, the air-conversion length from the image-side surface of the rearmost lens in the rear-side lens group up to the image plane becomes excessively short. In this case, since a lens outer diameter of the rear-side lens group in particular, becomes large, the front-end portion becomes large.

In a case of exceeding an upper limit value of conditional expression (4), the air-conversion length from the image-side surface of the lens positioned nearest to the image plane in the front-side lens group up to the aperture stop becomes excessively long. In this case, since the lens outer diameter of the front-side lens group becomes large, the front-end portion becomes large. Or, the air-conversion length from the image-side surface of the rearmost lens in the rear-side lens group up to the image plane becomes excessively short. Consequently, a lens necessary for aberration correction cannot be disposed. Moreover, since the space for focus adjustment cannot be achieved adequately, assembling the imaging system becomes difficult.

In the oblique-viewing objective optical system of the present embodiment, it is preferable that the following conditional expressions (5) and (6) be satisfied:

$$1.6 < |fF/f| < 4.5 \quad (5), \text{ and}$$

$$1.9 < fR/f < 5.3 \quad (6)$$

where, fF denotes a focal length of the front-side lens group, fR denotes a focal length of the rear-side lens group, and f denotes the focal length of the overall oblique-viewing objective optical system.

Conditional expression (5) is a conditional expression which regulates the focal length of the front-side lens group.

In a case of falling below a lower limit value of conditional expression (5), since a refractive power of the front-side lens group becomes large, the angle of view of the oblique-viewing objective optical system becomes large. As the angle of view becomes large, since a light-ray height at the front-side lens group becomes high, the lens outer-diameter becomes large. Furthermore, since the angle of view becomes large, a peripheral portion of an observation image becomes dark. For making the peripheral portion of image bright, illumination light has to be made brighter. However, when the illumination light is made brighter, an illuminating optical system becomes large. None of these is preferable for thinning the diameter of the front-end portion.

Moreover, since a radius of curvature of the first lens in particular, becomes small, processing of the lens becomes difficult. Furthermore, since the refractive power of the first lens becomes large, an aberration of the overall optical system is deteriorated. For correcting this aberration, it is necessary to make the number of lenses in the front-side lens group large. However, when the number of lenses is increased, the optical system becomes large in size.

In a case of exceeding an upper limit value of conditional expression (5), since the refractive power of the front-side lens group becomes small, the angle of view of the oblique-viewing objective optical system becomes small. When an attempt is made to secure a large angle of view in this state, a distance from the first lens of the front-side lens group up to the aperture stop becomes long. As the distance becomes long, since a light-ray height between the first lens and the aperture stop becomes high, the front-side lens group becomes large in size as well as the overall optical system becomes large-sized.

Conditional expression (6) is a conditional expression which regulates the focal length of the rear-side lens group.

In a case of falling below a lower limit value of conditional expression (6), since a refractive power of the rear-side lens group becomes large, an image position comes excessively closer to the rear-side lens group. As the image position becomes excessively closer, since the space for focus adjustment becomes narrow, the space necessary for the focus adjustment is inadequate. Consequently, a depth of a far-point side becomes shallower than a depth which is necessary essentially.

Furthermore, as the refractive power of the rear-side lens group becomes large, a refractive power of each lens in the rear-side lens group becomes large. In this case, since a radius of curvature of each lens becomes small, processing of the lens becomes difficult.

In a case of exceeding an upper limit value of conditional expression (6), since the refractive power of the rear-side lens group becomes small, the image position is excessively away from the rear-side lens group. In this case, since a path length in glass from the aperture stop up to the image position becomes long, the overall optical system becomes large-sized.

In the oblique-viewing objective optical system of the present embodiment, it is preferable that the following conditional expressions (7) and (8) be satisfied:

$$1.2 < |f1/f| < 4.5 \quad (7), \text{ and}$$

$$0.001 < |f1/f2| < 0.9 \quad (8)$$

where, f1 denotes a focal length of the first lens, f2 denotes a focal length of the second lens, and f denotes the focal length of the overall oblique-viewing objective optical system.

Conditional expression (7) is a conditional expression which regulates the focal length of the first lens.

In a case of falling below a lower limit value of conditional expression (7), since the refractive power of the first lens becomes large, the angle of view of the oblique-viewing objective optical system becomes large. As the angle of view becomes large, since the height of a light ray at a lens in the front-side lens group becomes high, the lens outer diameter becomes large. Therefore, falling below the lower limit value of conditional expression (7) is not preferable for thinning the diameter of the front-end portion.

Moreover, since the radius of curvature of the first lens becomes small, processing of the lens becomes difficult. Furthermore, by the refractive power of the first lens becoming large, a degradation of optical performance in a case of decentering of lens in particular, becomes large. As a result, it becomes difficult to realize an oblique-viewing objective optical system having a stable optical performance.

In a case of exceeding an upper limit value of conditional expression (7), since the refractive power of the first lens becomes small, the angle of view of the oblique-viewing objective optical system becomes small. When an attempt is made to secure a large angle of view in this state, the distance from the first lens up to the aperture stop becomes long. As the distance from the first lens up to the aperture stop becomes long, since a height of the light ray from the first lens up to the aperture stop becomes high, the first lens becomes large in size, as well as the overall optical system becomes large-sized. Therefore, exceeding the upper limit value of conditional expression (7) is not preferable for thinning the diameter of the front-end portion.

Conditional expression (8) is a conditional expression which regulates a ratio of the focal length of the first lens and the focal length of the second lens is regulated.

In a case of falling below a lower limit value of conditional expression (8), since the refractive power of the second lens becomes small, an aberration correction by the second lens becomes difficult. In this case, since occurrence of an aberration such as a spherical aberration and a coma cannot be suppressed, an optical system having a high performance cannot be achieved.

Furthermore, since the refractive power of the first lens becomes large, the radius of curvature of the first lens becomes small. In this case, the processing of the first lens becomes difficult. Moreover, in a case of decentering of the first lens, the optical performance is degraded substantially.

In a case of exceeding an upper limit value of conditional expression (8), since the refractive power of the first lens becomes small, the radius of curvature of the first lens becomes large. In this case, the angle of view of the optical system becomes small, as well as the outer diameter of the first lens becomes large. Furthermore, the overall optical system becomes large-sized.

In the oblique-viewing objective optical system of the present embodiment, it is preferable that the second lens has a positive refractive power, and the following conditional expression (7') be satisfied:

$$1.2<|f1/f|<2.4 \qquad (7')$$

where, f1 denotes the focal length of the first lens, and f denotes the focal length of the overall oblique-viewing objective optical system.

The front-side lens group has a negative refractive power. Therefore, the size of the angle of view of the optical system is determined by the magnitude of the refractive power of the front-side lens group. The front-side lens group includes the first lens having a negative refractive power and the second lens. In a case in which the second lens has a positive refractive power, the size of the angle of view of the optical system is determined by the magnitude of the negative refractive power of the first lens.

In a case in which the second lens has a positive refractive power, and in a case in which the second lens does not have a positive refractive power, when an attempt is made to let the negative refractive of the front-side lens group to be the same, in the case in which the second lens has a positive refractive power, it is necessary to make the negative refractive power of the first lens to be even larger. Moreover, when an attempt is made to cope even with further widening of angle of the optical system, it is necessary to make the negative refractive power of the first lens even larger.

For such reasons, in the case in which the second lens has a positive refractive power, it is preferable to satisfy conditional expression (7'). By satisfying conditional expression (7'), even in the case in which the second lens has a positive refractive power, it is possible to secure a wide angle of view, and besides, by the positive refractive power of the second lens, it is possible to correct an aberration favorably.

In the oblique-viewing objective optical system of the present embodiment, it is preferable that the second lens has a negative refractive power, and the following conditional expression (7") be satisfied:

$$1.9<|f1/f|<4.5 \qquad (7")$$

where, f1 denotes the focal length of the first lens, and f denotes the focal length of the overall oblique-viewing objective optical system.

By the second lens having a negative refractive power, the negative refractive power necessary for the front-side lens group can be let to be shared by the first lens and the second lens. Consequently, as compared to the case in which the second lens does not have a negative refractive power, it is possible to make the negative refractive power of the first lens small.

For such reasons, in the case in which the second lens has a negative refractive power, it is preferable to satisfy conditional expression (7"). By satisfying conditional expression (7"), even in the case in which the second lens has a negative refractive power, a wide angle of view can be secured. Besides, when compared to a case in which the first lens group includes one negative lens, since it is possible to make the negative refractive power of the first lens small, it is possible suppress an occurrence of aberration.

In the oblique-viewing objective optical system of the present embodiment, it is preferable that the second lens has a positive refractive power, and the following condition expression (8') be satisfied:

$$0.02<|f1/f2|<0.22 \qquad (8')$$

where, f1 denotes the focal length of the first lens, and f2 denotes the focal length of the second lens.

Conditional expression (8') is a conditional expression related to a ratio of the focal length of the first lens and the focal length of the second lens. This conditional expression (8'), in particular, is a conditional expression related to a balance of the negative refractive power of the first lens and the positive refractive power of the second lens.

In a case of falling below a lower limit value of conditional expression (8'), since the positive refractive power in the second lens becomes small, an effect of aberration correction becomes small. In a case of exceeding an upper limit value of conditional expression (8'), since the negative refractive power in the first lens becomes small, the angle of view of the optical system becomes small. Moreover, the outer diameter of the first lens becomes large, and also the overall optical system becomes large-sized.

In the oblique-viewing objective optical system of the present embodiment, it is preferable that the second lens is a cemented lens, and the following conditional expression (9) be satisfied:

$$|nd(L2f)-nd(L2b)| \leq 0.1 \qquad (9)$$

where, nd (L2f) denotes a refractive index of an object-side lens in the cemented lens of the second lens, and nd (L2b) denotes a refractive index of an image-plane side lens in the cemented lens of the second lens.

When a pixel pitch of the image pickup element becomes small, the image height of the objective optical system also becomes small. Consequently, a difference between a light-ray height of a light beam which is focused axially (hereinafter, referred to as 'axial light-ray height) and a light-ray height of a light beam which is focused at a position of the maximum image height (hereinafter, referred to as 'off-axis light-ray height') becomes small at each lens surface. When the difference in the heights becomes small in such manner, particularly, correction of a longitudinal chromatic aberration and correction of a chromatic aberration of magnification become difficult.

The longitudinal chromatic aberration is affected substantially by a lens disposed at a position where the axial light-ray height is high, and the longitudinal chromatic aberration is affected substantially by a lens disposed at a position where the off-axis light-ray height is high. Therefore, as to which one of an effect of correction on the longitudinal chromatic aberration and an effect of correction on the chromatic aberration of magnification is more, is verified for each lens, and a balance of a glass-material arrangement for each is facilitated.

However, when both of the axial light-ray height and the off-axis light ray height become low, there is no difference in the magnitude of the effect of correction on the longitudinal chromatic aberration and the magnitude of the effect of correction on the chromatic aberration of magnification occurring at each lens. Consequently, it becomes difficult to suppress both the chromatic aberrations to be small.

Therefore, a cemented lens is disposed in each of the front-side lens group and the rear-side lens group, and the chromatic aberration in each lens group and the chromatic aberration in the overall optical system are corrected favorably. As mentioned above, in the front-side lens group, the first lens has mainly a role of determining the angle of view of the optical system. Therefore, letting the second lens to be a cemented lens, the chromatic aberration in the front-side lens group is to be corrected.

The optical path converting element is disposed between the second lens and the aperture stop, but a position of the second lens is near the aperture stop. Consequently, both the axial light-ray height and the off-axis light ray height in the second lens are low, and there is not much difference between the two light-ray heights.

For such reason, in a case of forming the second lens by a cemented lens, it is preferable to make small a difference in the refractive index of the positive lens and the refractive index of the negative lens, or in other words, to satisfy conditional expression (9). By satisfying conditional expression (9), it is possible to correct the longitudinal chromatic aberration and the chromatic aberration of magnification in the front-side lens group favorably.

In a case of exceeding an upper limit value of conditional expression (9), a difference in the refractive indices of the two lenses in the cemented lens becomes large. In this case, since a radius of curvature of a cemented surface of the cemented lens becomes excessively large, an effect of correction on the chromatic aberration by the cemented lens becomes small. As a result, the chromatic aberration in the front-side lens group and the chromatic aberration in the overall objective optical system cannot be corrected favorably.

The second lens may be a single lens having a positive refractive power or a single lens having a negative refractive power.

In a case in which the second lens is a single lens having a positive refractive power, it is preferable that the glass material for the second lens be a high-dispersion glass material. When Abbe number for the second lens is let to be vd(L2), specifically, it is preferable that vd (L2) be not more than 50, and it is more preferable that vd (L2) be not more than 45.

Moreover, in a case in which the second lens is a single lens having a negative refractive power, it is preferable that the glass material for the second lens be a low-dispersion glass material. Specifically, it is preferable that vd (L2) be not less than 50, and it is more preferable that vd (L2) be not less than 60.

By satisfying these conditions, it is possible to correct the chromatic aberration such that the chromatic aberration of the optical system becomes small. When these conditions are not satisfied, since the chromatic aberration of the optical system cannot be corrected favorably, an objective optical system with a high performance cannot be achieved.

Moreover, in the cemented lens in the rear-side lens group, it is preferable to use a low-dispersion glass material for the glass material of the positive lens and a high-dispersion glass material for the glass material of the negative lens. Particularly, for the glass material of the negative lens, it is preferable to use a glass material having an anomalous dispersion. By doing so, it is possible to correct the chromatic aberration. Furthermore, it is possible to make the aberration of the overall objective optical system in a balanced state.

Moreover, an endoscope for oblique viewing of the present embodiment includes the abovementioned oblique-viewing objective optical system.

The oblique-viewing objective optical system of the present embodiment is an oblique-viewing objective optical system having a small size and a high performance. Therefore, by including such oblique-viewing objective optical system, it is possible to realize an endoscope in which a high quality image is achieved, and which has a front-end portion having a thinned diameter.

Moreover, it is possible to use the oblique-viewing objective optical system of the present invention in an endoscope apparatus. An endoscope apparatus includes at least the oblique-viewing objective optical system of the present embodiment and an image pickup element.

Prior to the description of examples, a general outline of the oblique-viewing objective optical system will be described below. In a lens cross-sectional view of each example, the optical path converting element is indicated as a diagram of an unfolded prism. Therefore, the optical path converting element has been depicted as a plane parallel plate.

An example of a prism in a state of not being unfolded is shown in FIG. 3. FIG. 3 is a lens cross-sectional view when the prism is depicted in the state of not being unfolded. Here, an oblique-viewing objective optical system according to the example 1 has been exemplified. The oblique-viewing objective optical system includes a front-side lens group GF and a rear-side lens group GR disposed via a prism P, and an aperture stop S is disposed between the prism P and the rear-side lens group GR.

In other words, in the oblique-viewing objective optical system, the front-side lens group GF is disposed on an object side of the prism P, and the rear-side lens group GR is disposed on an image side of the prism P. The front-side lens group GF has a negative refractive power and includes a first lens L1 and a second lens L2. The rear-side lens group GR has a positive refractive power, and includes a third lens L3 and a cemented CL.

The first lens L1 includes a negative lens having a concave surface directed toward the image-plane side. The second lens L2 includes a single lens having a convex surface directed toward the image-plane side. The second lens L2 may be a cemented lens having a convex surface directed toward the image-plane side. The third lens L3 includes a positive lens. The cemented lens CL includes a positive lens L4 which is a biconvex lens, and a negative lens L5 having a meniscus shape.

Figure 4A:
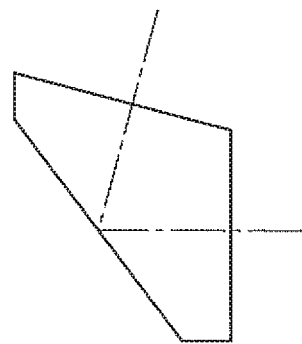
FIG. 4A, FIG. 4B, FIG. 4C, and FIG. 4D are diagrams showing prisms.
Figure 4B:
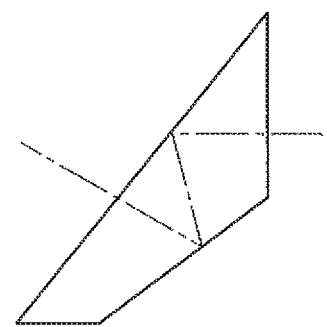

When the prism P depicted as a plane-parallel plate is arranged as a one-time reflection prism, as shown in FIG. 4A, it is possible to arrange an objective optical system for side viewing that enables 90° lateral observation. Moreover, as shown in FIG. 4B, when a reflecting surface of the prism is set to an angle other than 45°, it is possible to form an objective optical system for front viewing or rear viewing for an angle other than 45°. Moreover, as shown in FIG. 4B, when the prism is arranged as a two-times reflection prism, it is also possible to form an objective optical system for front viewing of 45°.

Figure 4C:
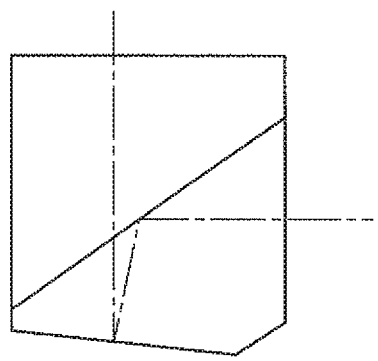
Figure 4D:
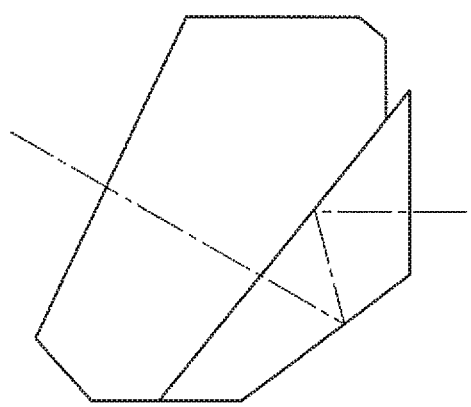
Figure 6A:
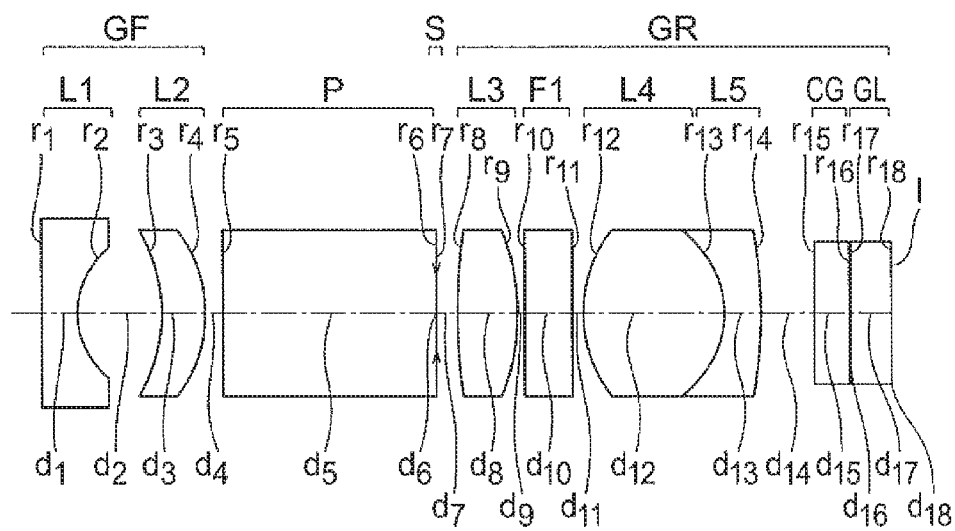
FIG. 6A is a diagram showing in cross-section, an arrangement of an oblique-viewing objective optical system according to an example 2.
Figures 6B, 6C, 6D, 6E:
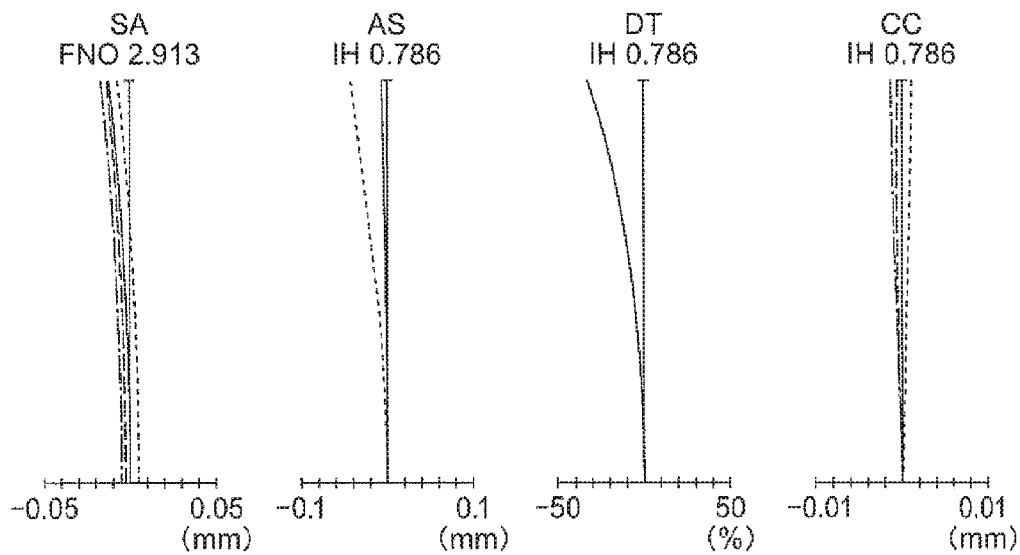
FIG. 6B, FIG. 6C, FIG. 6D, and FIG. 6E are aberration diagrams of the example 2.
Figure 7A:
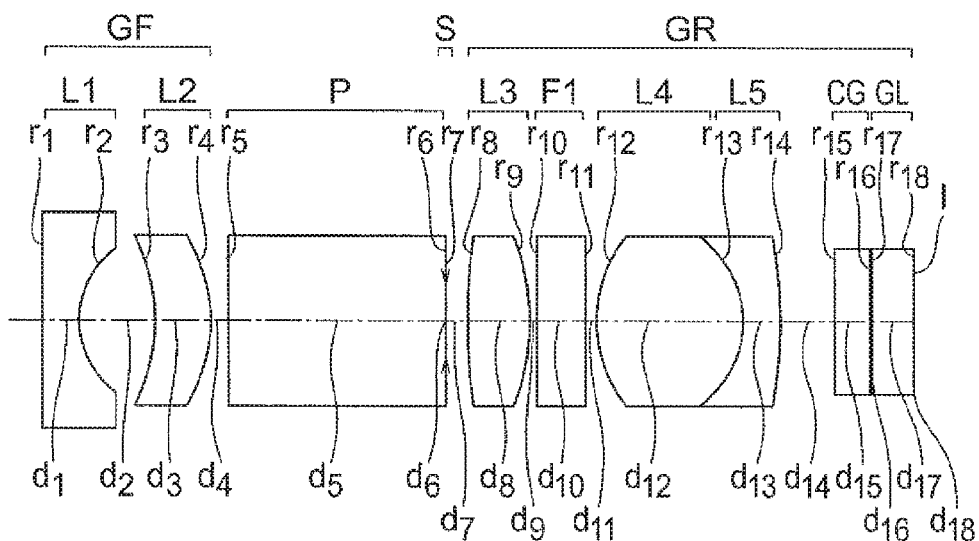
FIG. 7A is a diagram showing in cross-section, an arrangement of an oblique-viewing objective optical system according to an example 3.
Figures 7B, 7C, 7D, 7E:
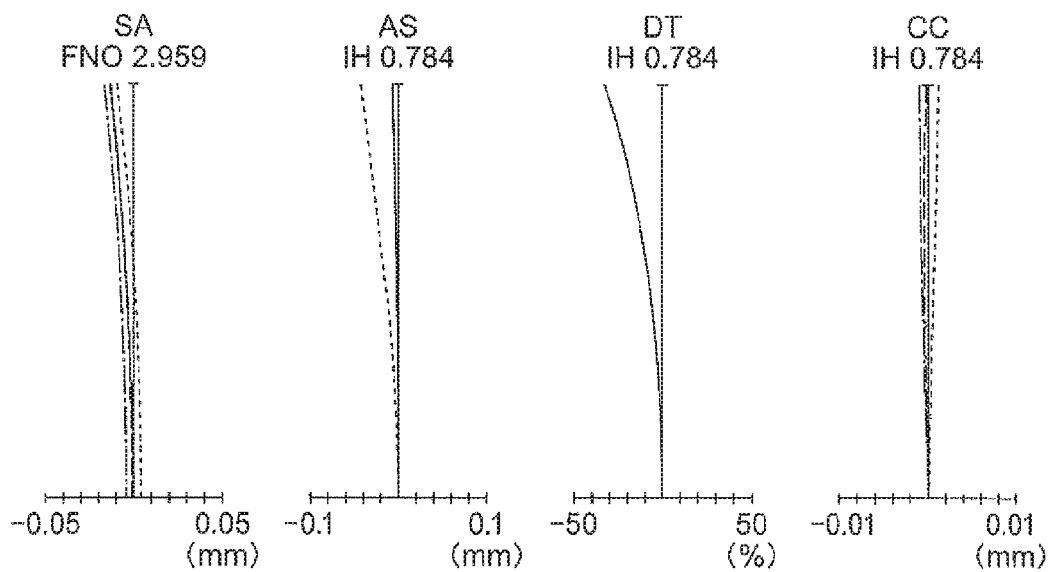
FIG. 7B, FIG. 7C, FIG. 7D, and FIG. 7E are aberration diagrams of the example 3.
Figure 9A:
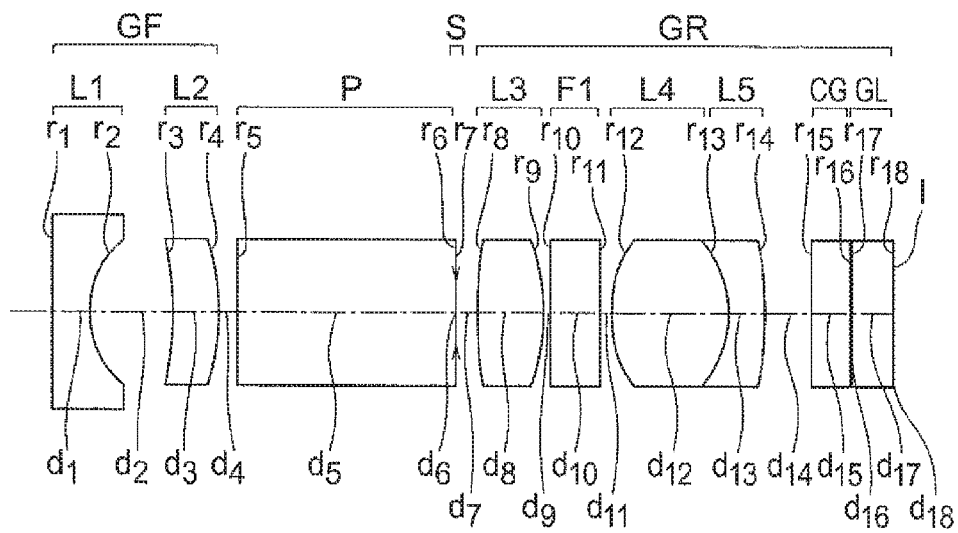
FIG. 9A is a diagram showing in cross-section, an arrangement of an oblique-viewing objective optical system according to an example 5.
Figures 9B, 9C, 9D, 9E:
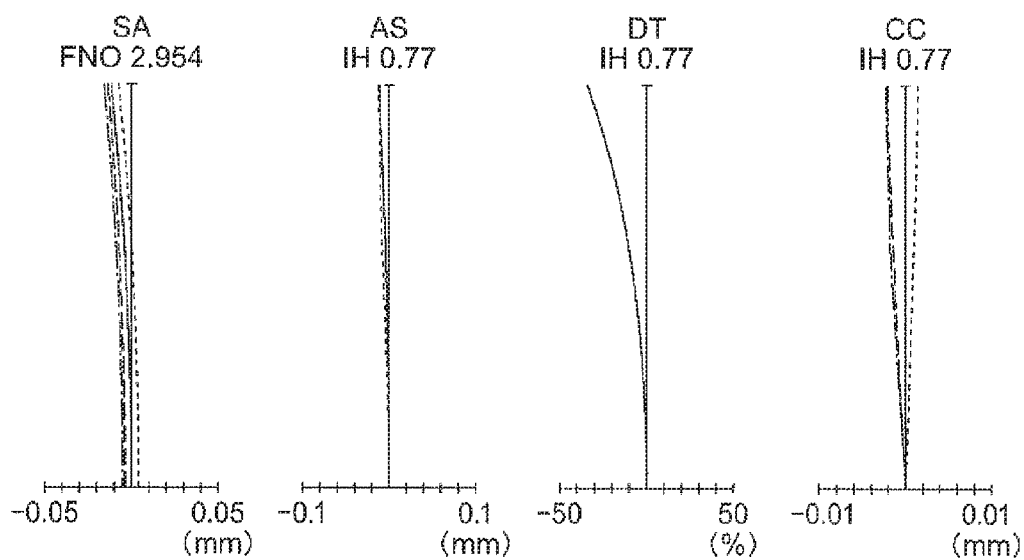
FIG. 9B, FIG. 9C, FIG. 9D, and FIG. 9E are aberration diagrams of the example 5.
Figure 10A:
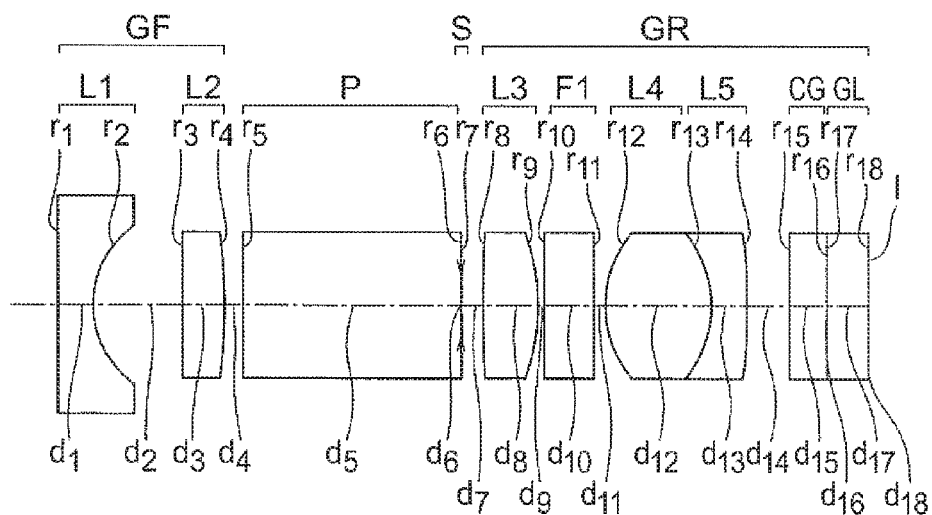
FIG. 10A is a diagram showing in cross-section, an arrangement of an oblique-viewing objective optical system according to an example 6.
Figures 10B, 10C, 10D, 10E:
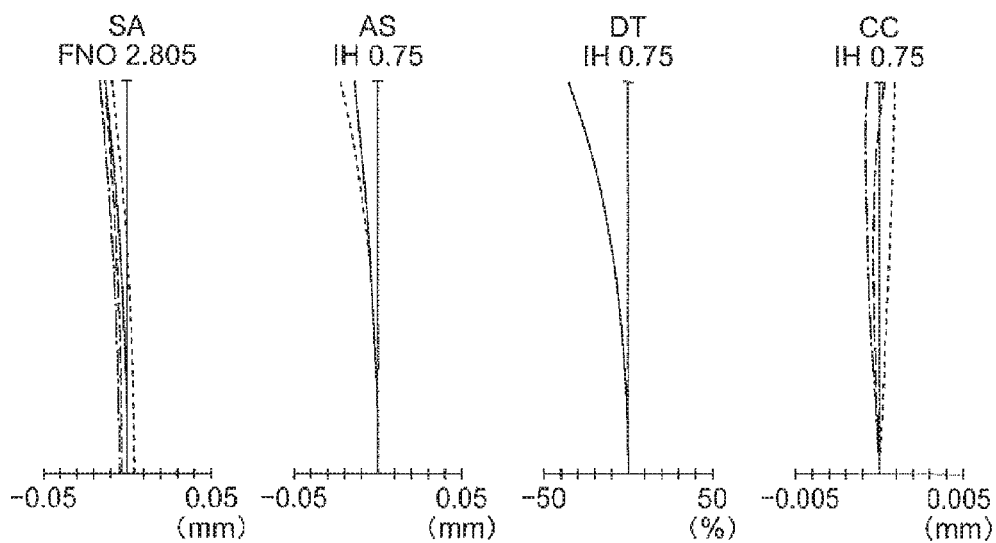
FIG. 10B, FIG. 10C, FIG. 10D, and FIG. 10E are aberration diagrams of the example 6.
Figure 11A:
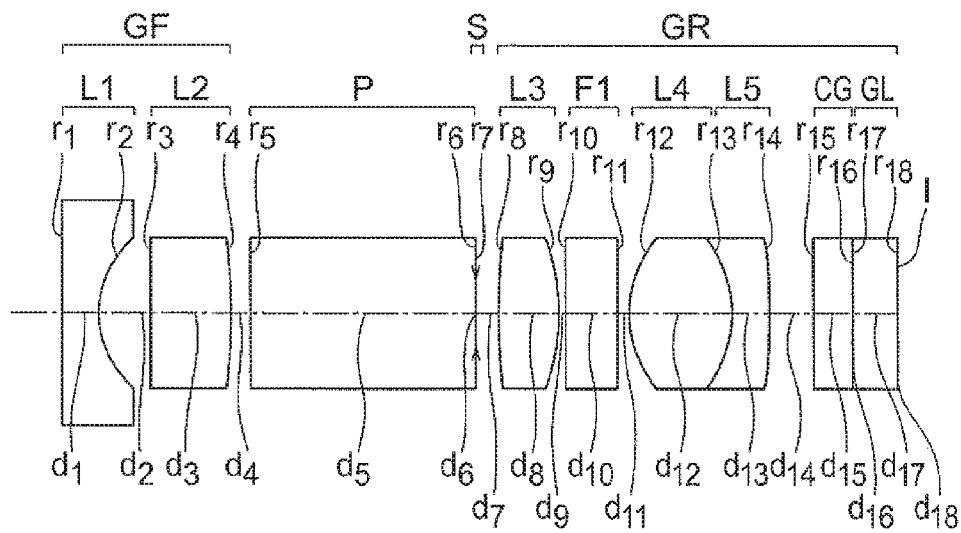
FIG. 11A is a diagram showing in cross-section, an arrangement of an oblique-viewing objective optical system according to an example 7.
Figures 11B, 11C, 11D, 11E:
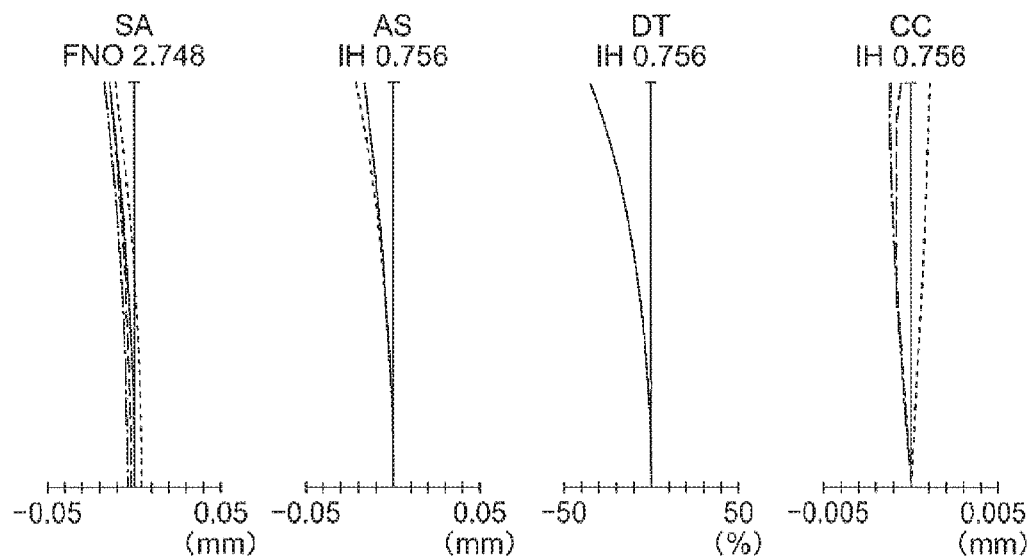
FIG. 11B, FIG. 11C, FIG. 11D, and FIG. 11E are aberration diagrams of the example 7.
Figure 12A:
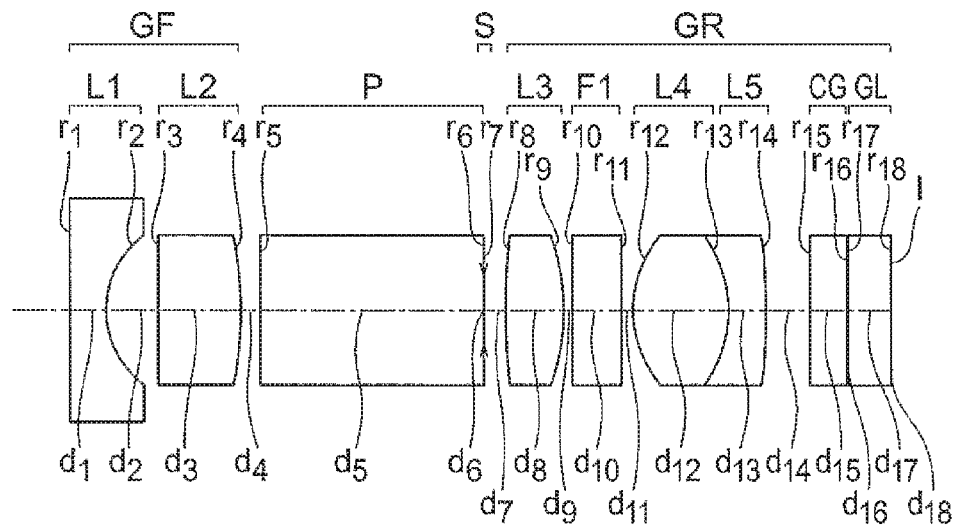
FIG. 12A is a diagram showing in cross-section, an arrangement of an oblique-viewing objective optical system according to an example 8.
Figures 12B, 12C, 12D, 12E:
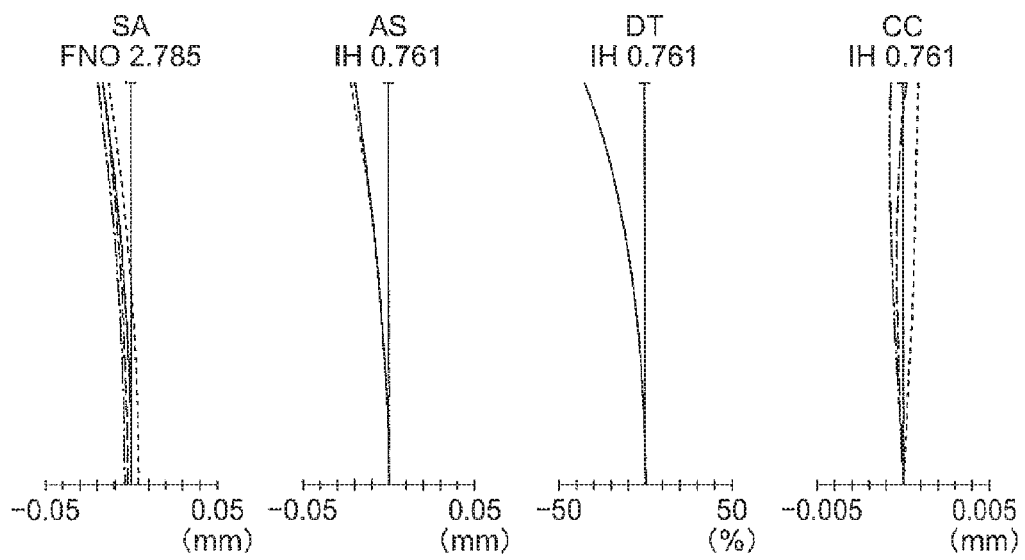
FIG. 12B, FIG. 12C, FIG. 12D, and FIG. 12E are aberration diagrams of the example 8.
Figure 13A:
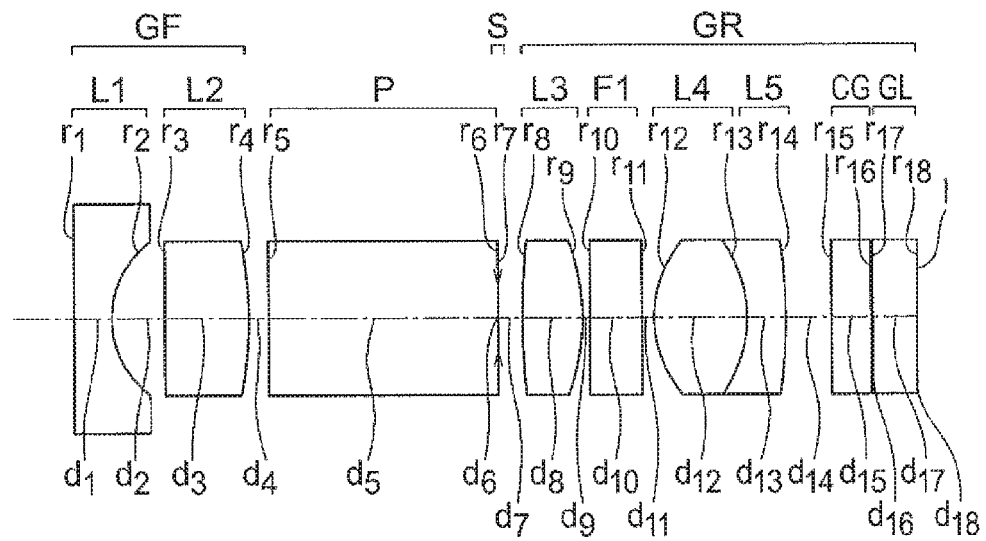
FIG. 13A is a diagram showing in cross-section, an arrangement of an oblique-viewing objective optical system according to an example 9.
Figures 13B, 13C, 13D, 13E:
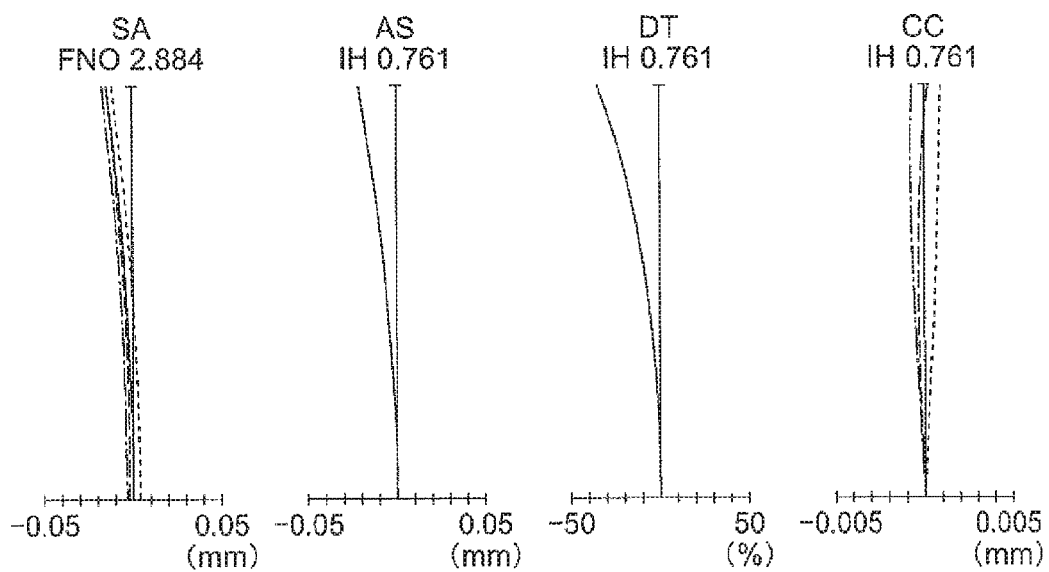
FIG. 13B, FIG. 13C, FIG. 13D, and FIG. 13E are aberration diagrams of the example 9.
Figure 14A:
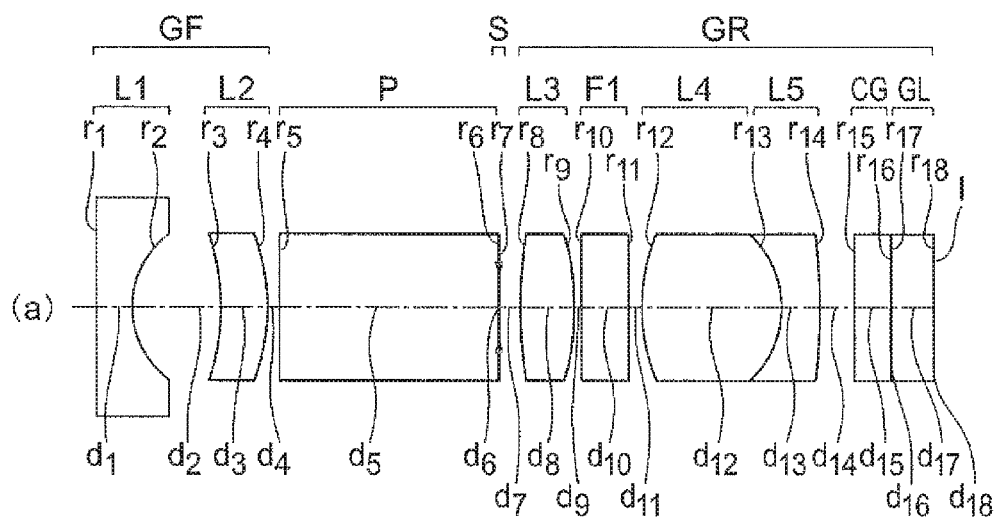
FIG. 14A is a diagram showing in cross-section, an arrangement of an oblique-viewing objective optical system according to an example 10.
Figures 14B, 14C, 14D, 14E:
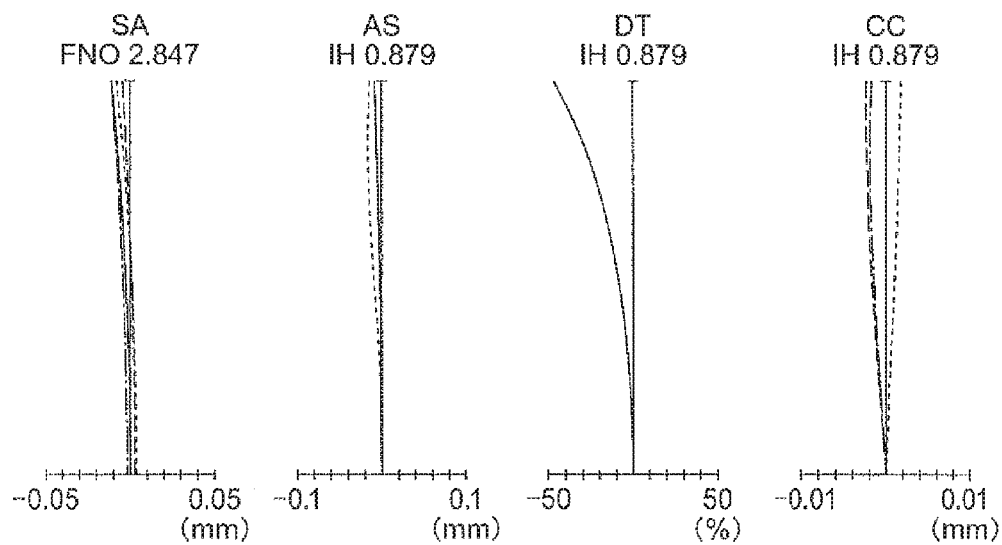
FIG. 14B, FIG. 14C, FIG. 14D, and FIG. 14E are aberration diagrams of the example 10.
Figure 15A:
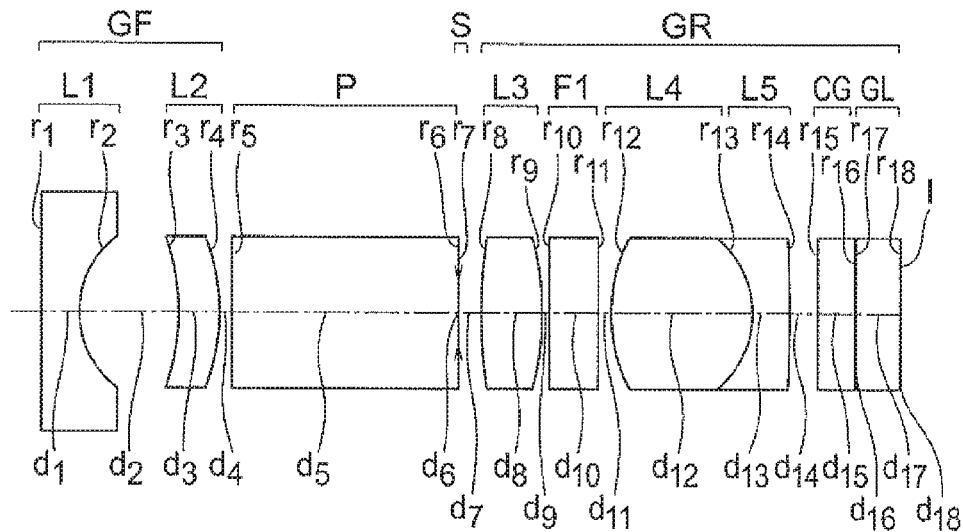
FIG. 15A is a diagram showing in cross-section, an arrangement of an oblique-viewing objective optical system according to an example 11.
Figures 15B, 15C, 15D, 15E:
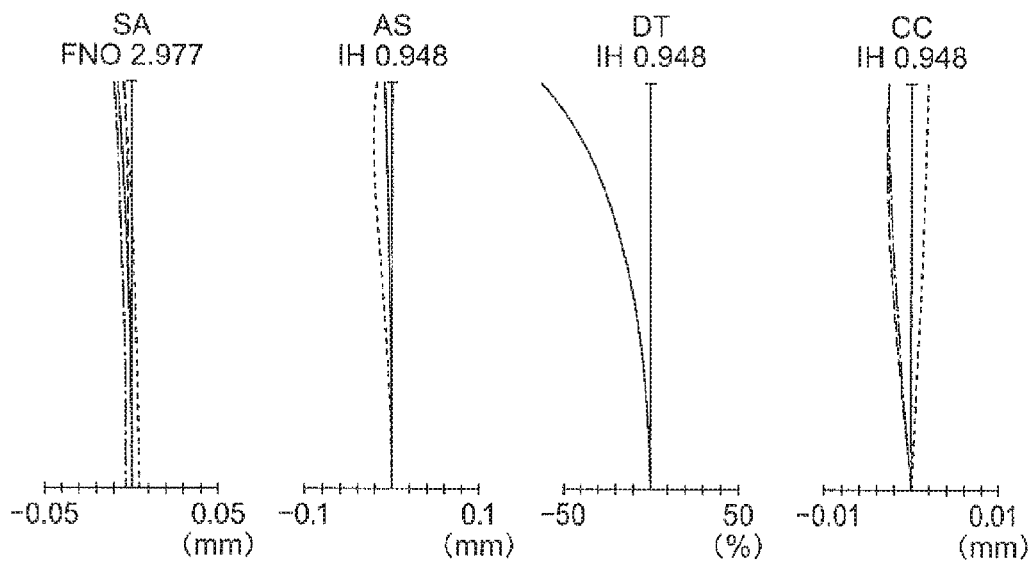
FIG. 15B, FIG. 15C, FIG. 15D, and FIG. 15E are aberration diagrams of the example 11.
Figure 16A:
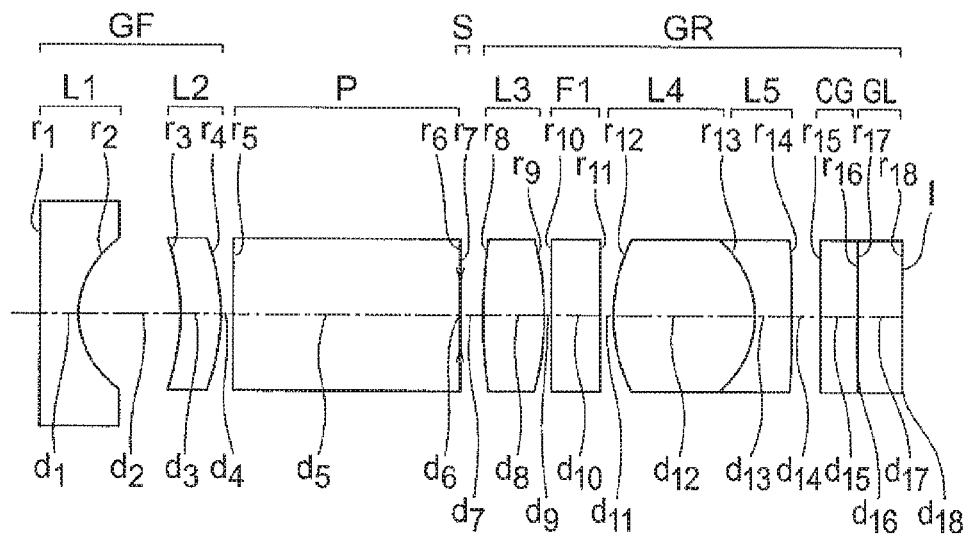
FIG. 16A is a diagram showing in cross-section, an arrangement of an oblique-viewing objective optical system according to an example 12.
Figures 16B, 16C, 16D, 16E:
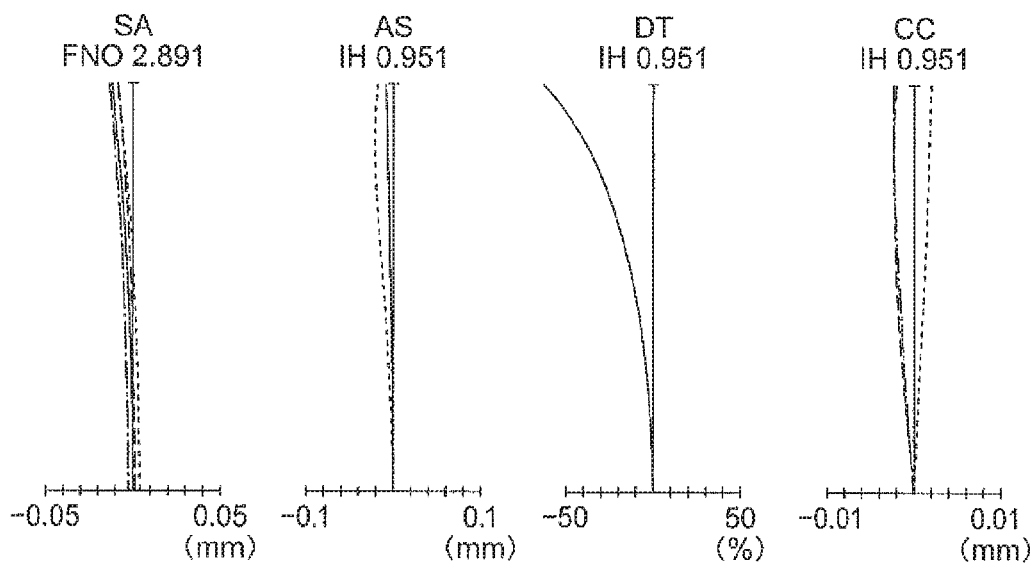
FIG. 16B, FIG. 16C, FIG. 16D, and FIG. 16E are aberration diagrams of the example 12.
Figure 17A:
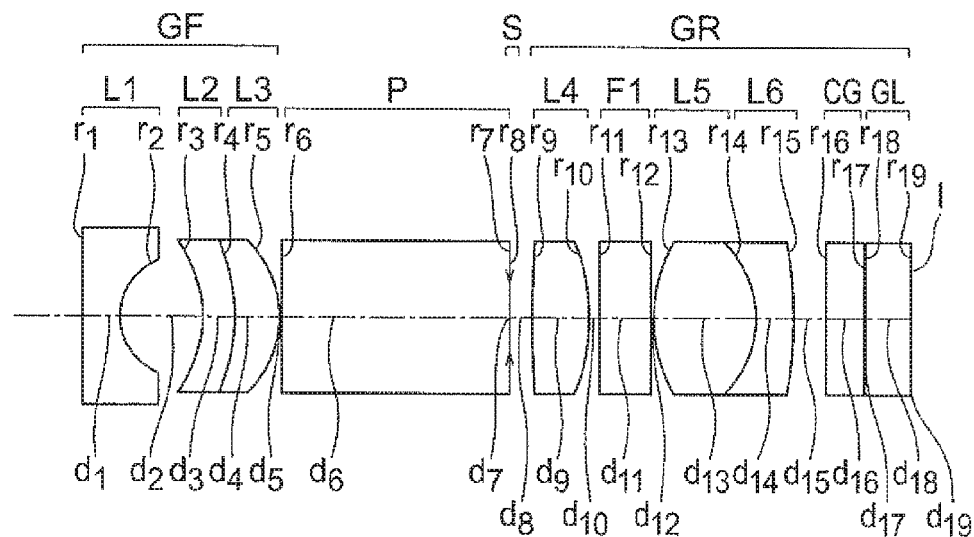
FIG. 17A is a diagram showing in cross-section, an arrangement of an oblique-viewing objective optical system according to an example 13.
Figures 17B, 17C, 17D, 17E:
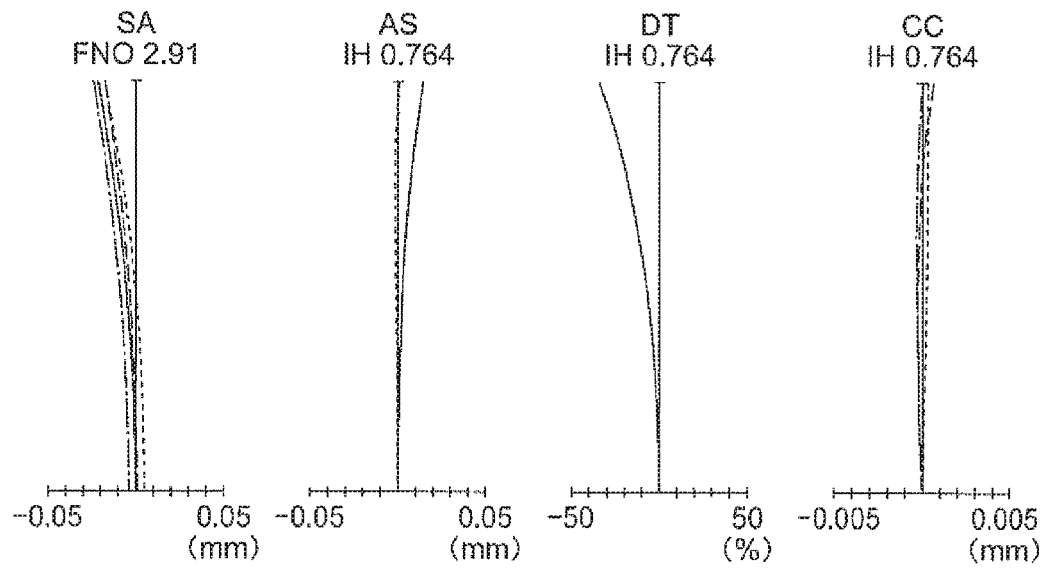
FIG. 17B, FIG. 17C, FIG. 17D, and FIG. 17E are aberration diagrams of the example 13.
Figure 18A:
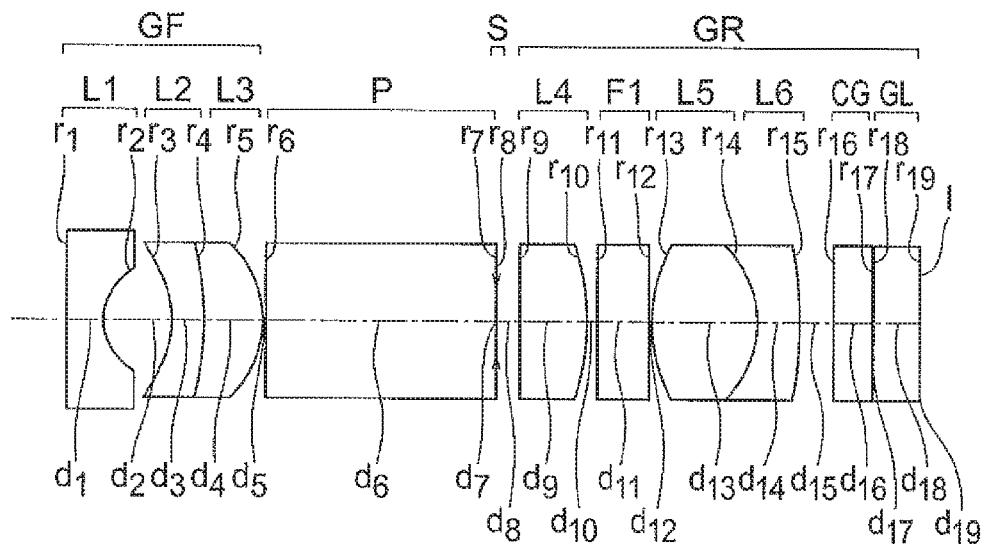
FIG. 18A is a diagram showing in cross-section, an arrangement of an oblique-viewing objective optical system according to an example 14.
Figures 18B, 18C, 18D, 18E:
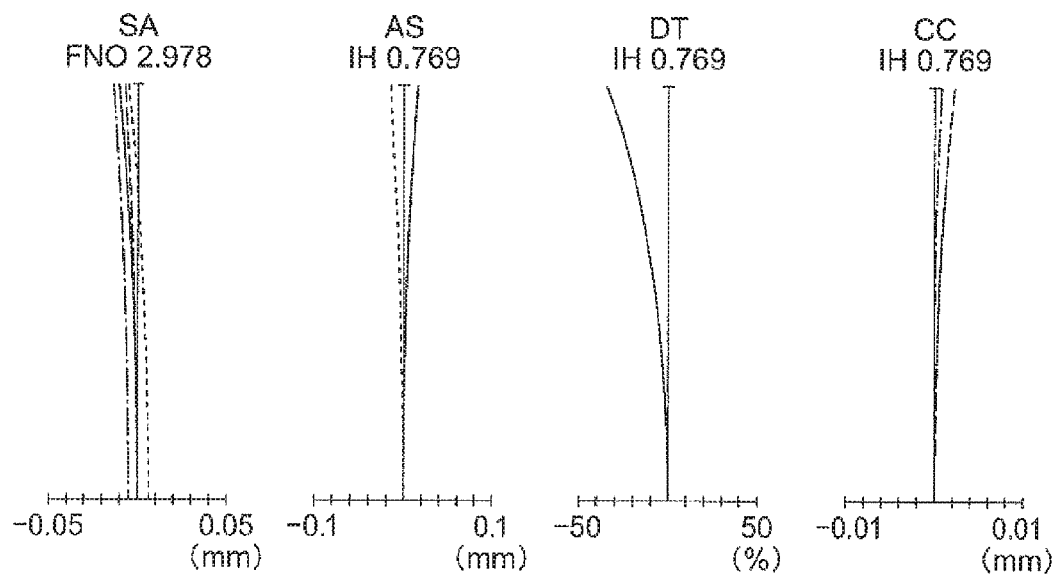
FIG. 18B, FIG. 18C, FIG. 18D, and FIG. 18E are aberration diagrams of the example 14.
Figure 19A:
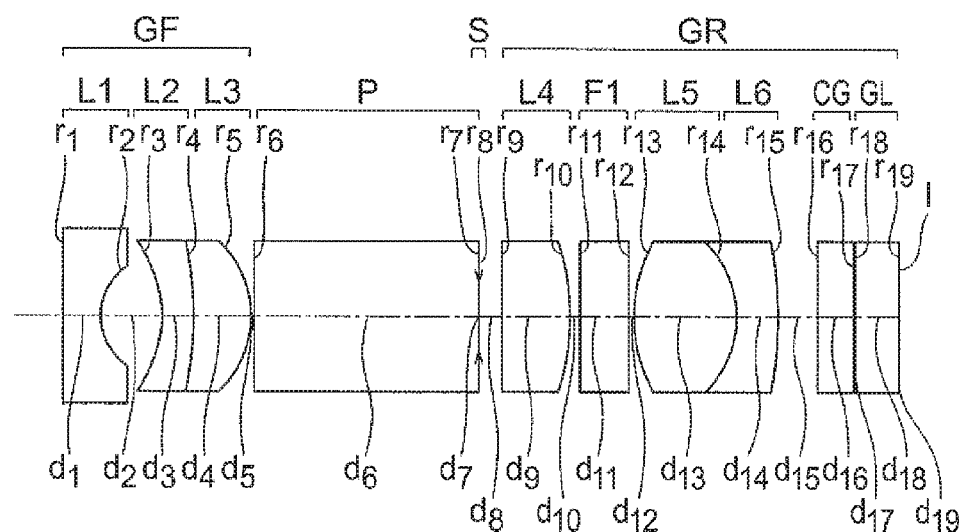
FIG. 19A is a diagram showing in cross-section, an arrangement of an oblique-viewing objective optical system according to an example 15.
Figures 19B, 19C, 19D, 19E:
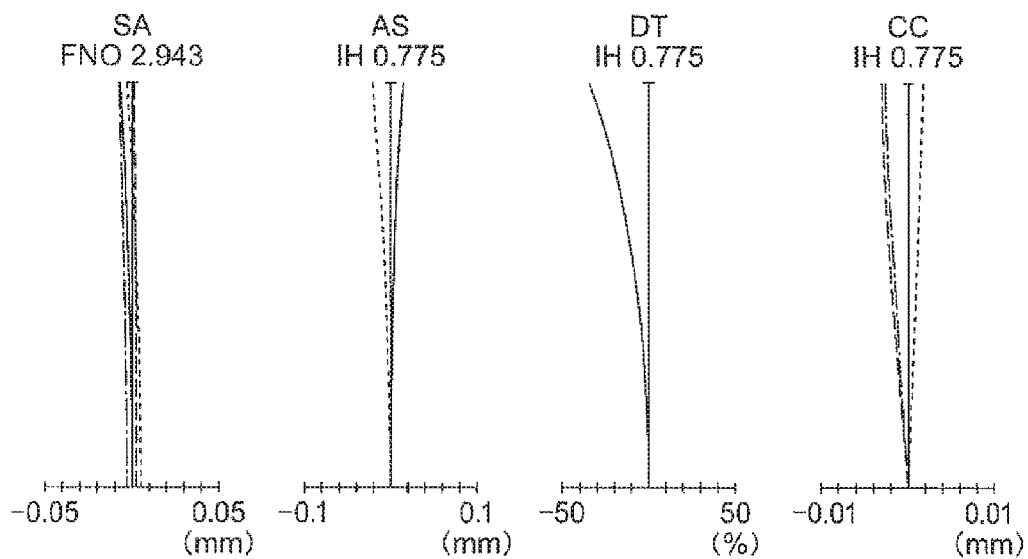
FIG. 19B, FIG. 19C, FIG. 19D, and FIG. 19E are aberration diagrams of the example 15.
Figure 20A:
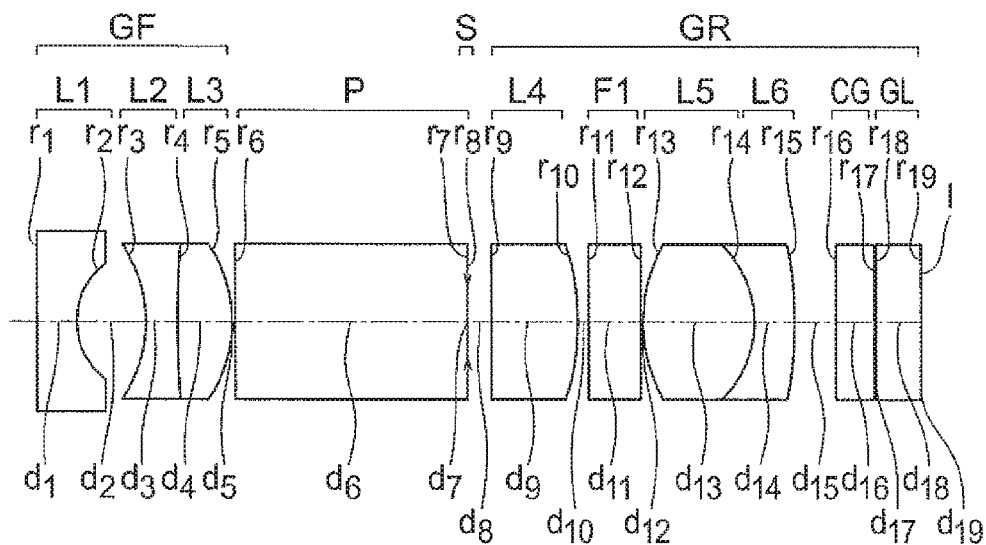
FIG. 20A is a diagram showing in cross-section, an arrangement of an oblique-viewing objective optical system according to an example 16.
Figures 20B, 20C, 20D, 20E:
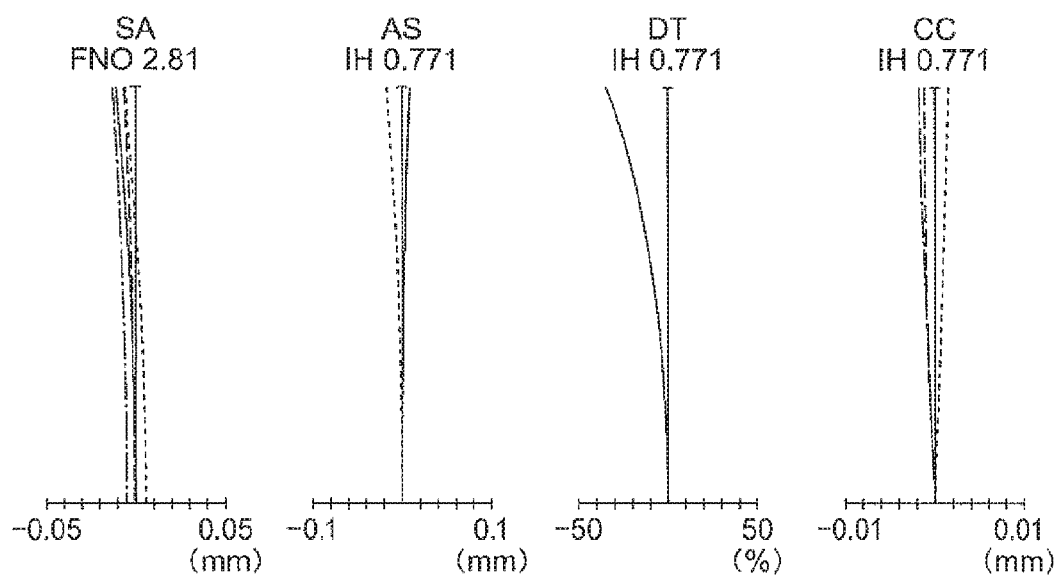
FIG. 20B, FIG. 20C, FIG. 20D, and FIG. 20E are aberration diagrams of the example 16.
Figure 21A:
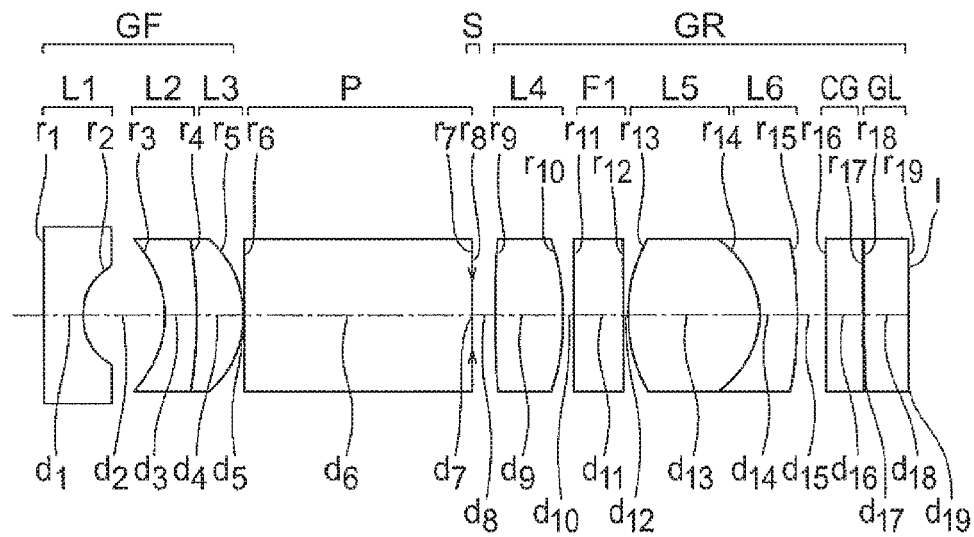
FIG. 21A is a diagram showing in cross-section, an arrangement of an oblique-viewing objective optical system according to an example 17.
Figures 21B, 21C, 21D, 21E:
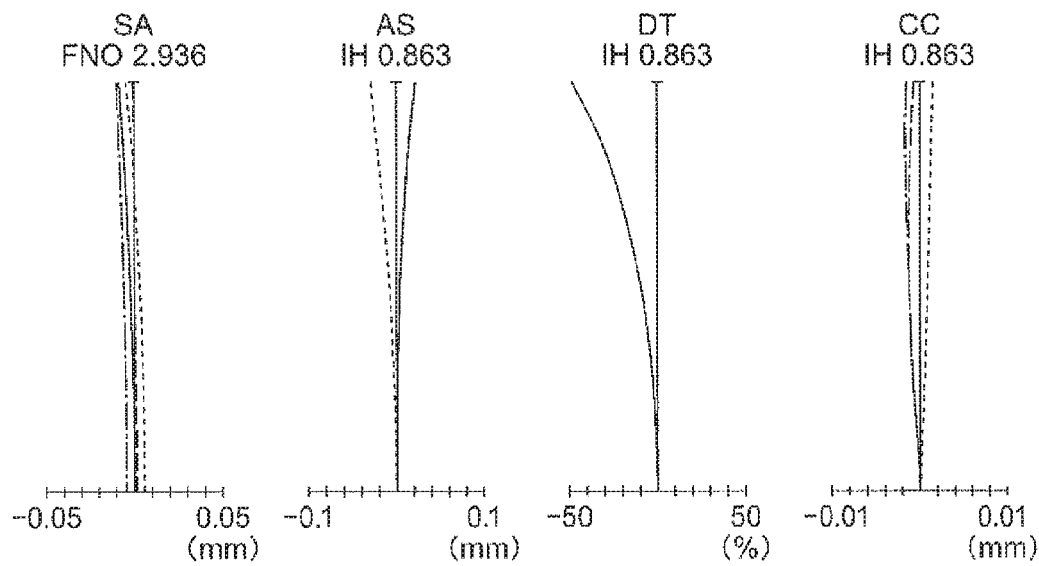
FIG. 21B, FIG. 21C, FIG. 21D, and FIG. 21E are aberration diagrams of the example 17.
Figure 22A:
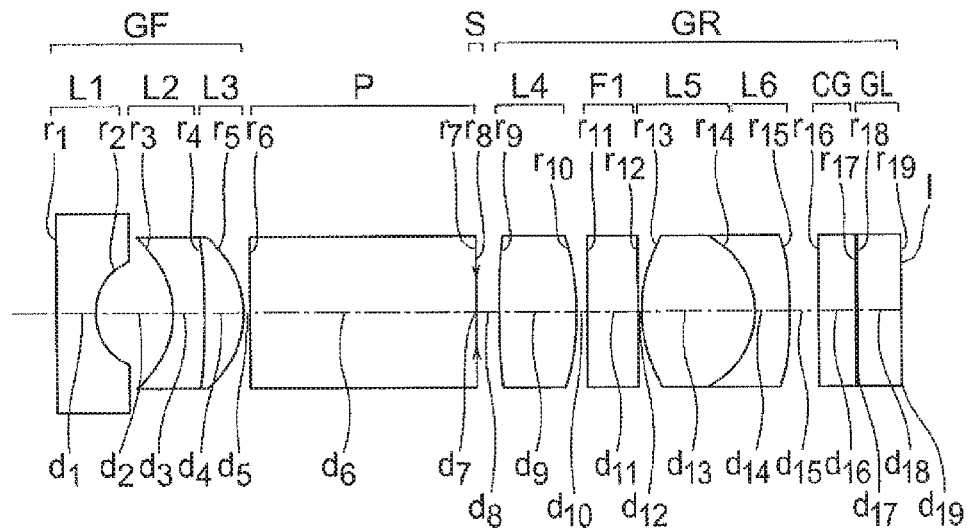
FIG. 22A is a diagram showing in cross-section, an arrangement of an oblique-viewing objective optical system according to an example 18.
Figures 22B, 22C, 22D, 22E:
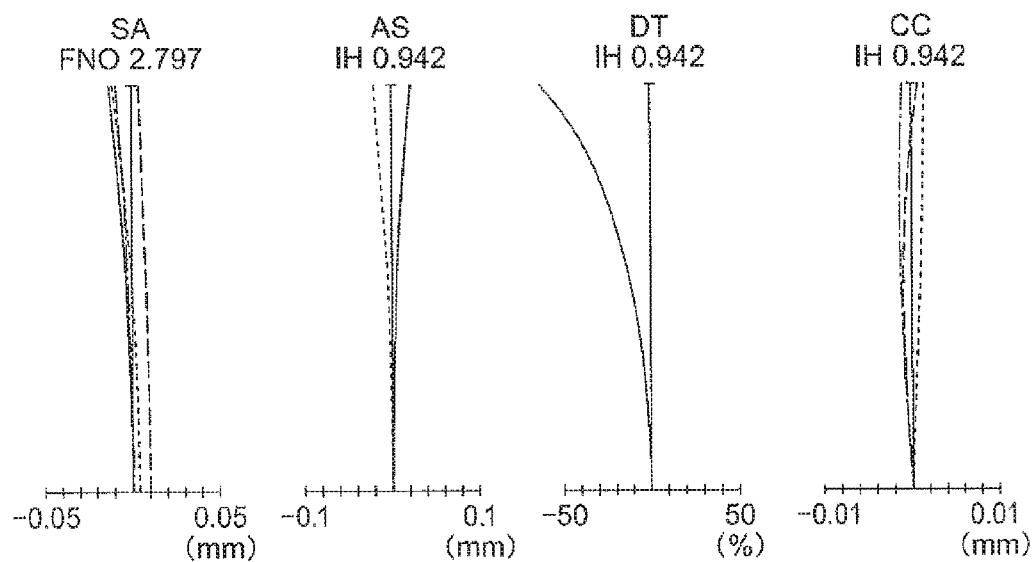
FIG. 22B, FIG. 22C, FIG. 22D, and FIG. 22E are aberration diagrams of the example 18.
Figure 23A:
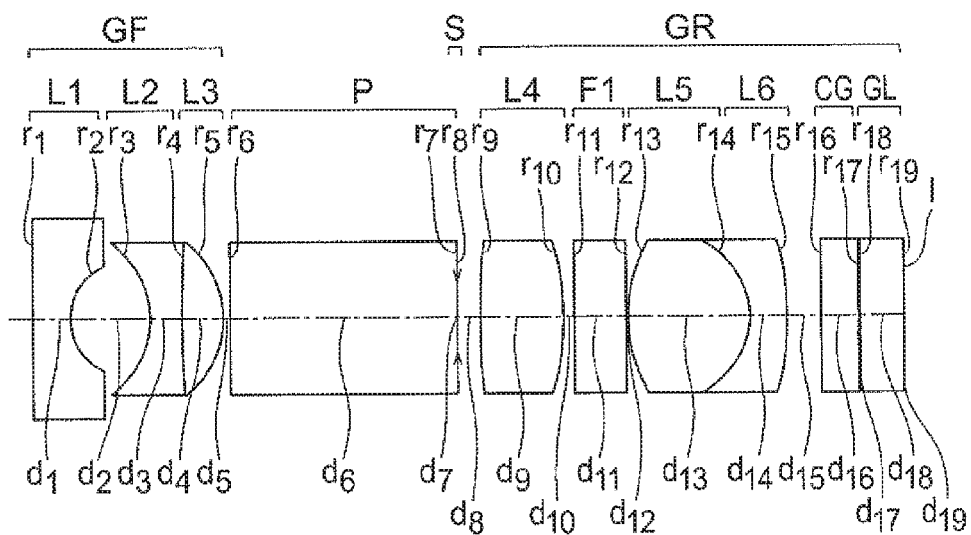
FIG. 23A is a diagram showing in cross-section, an arrangement of an oblique-viewing objective optical system according to an example 19.
Figures 23B, 23C, 23D, 23E:
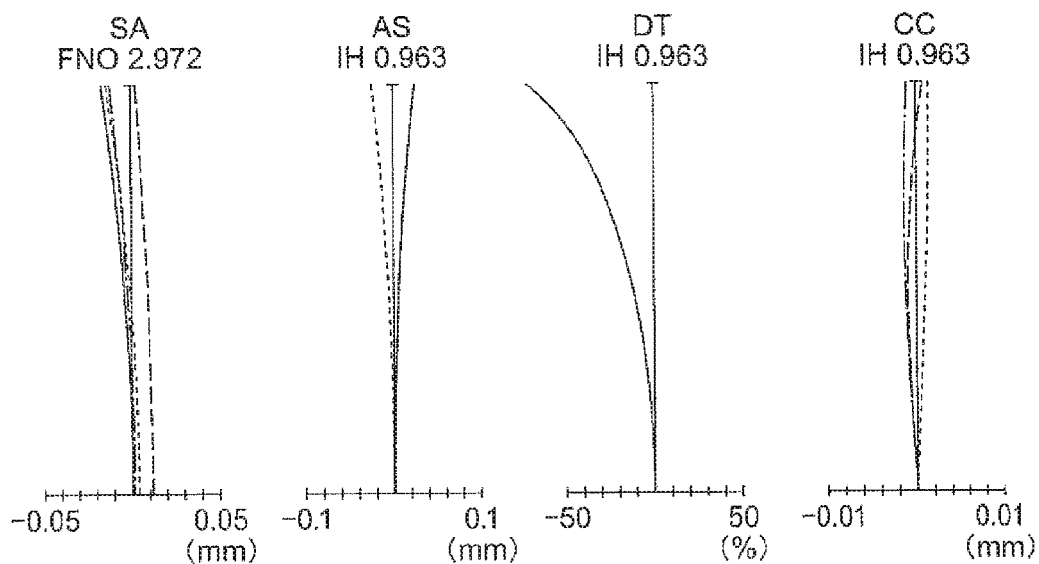
FIG. 23B, FIG. 23C, FIG. 23D, and FIG. 23E are aberration diagrams of the example 19.
Figure 24A:
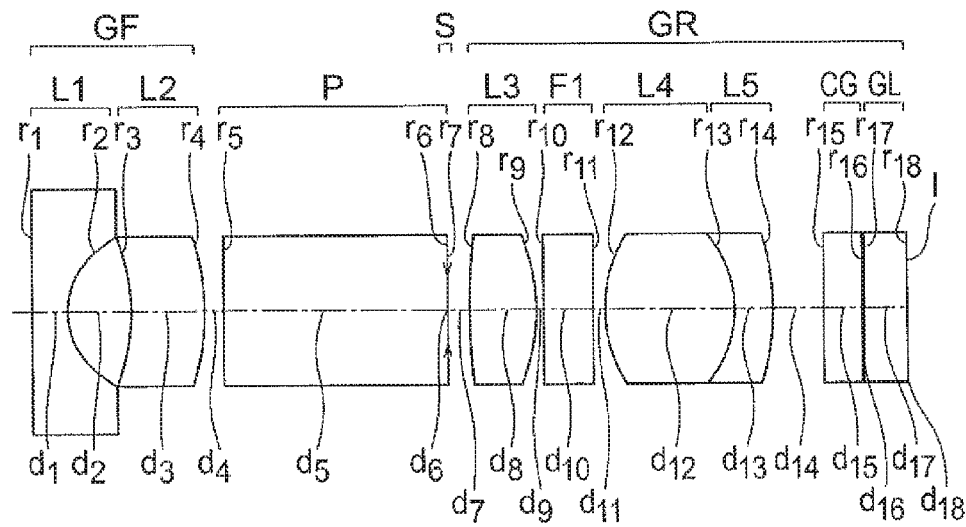
FIG. 24A is a diagram showing in cross-section, an arrangement of an oblique-viewing objective optical system according to an example 20.
Figures 24B, 24C, 24D, 24E:
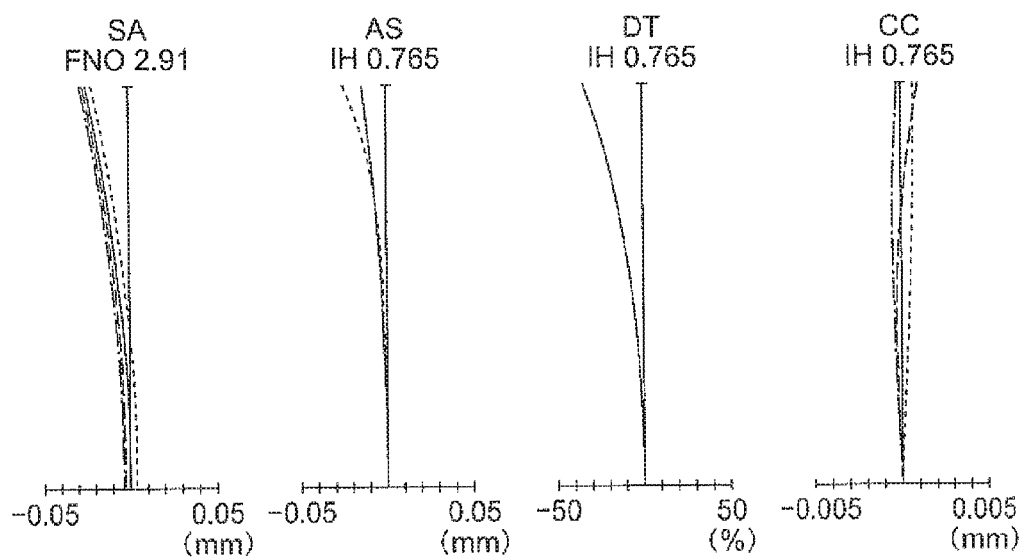
FIG. 24B, FIG. 24C, FIG. 24D, and FIG. 24E are aberration diagrams of the example 20.
Figure 25A:
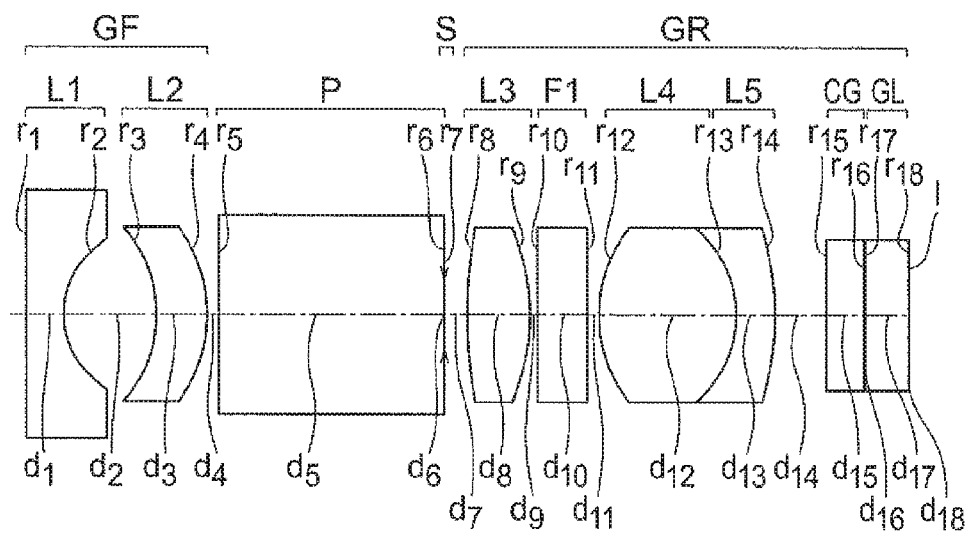
FIG. 25A is a diagram showing in cross-section, an arrangement of an oblique-viewing objective optical system according to an example 21.
Figures 25B, 25C, 25D, 25E:
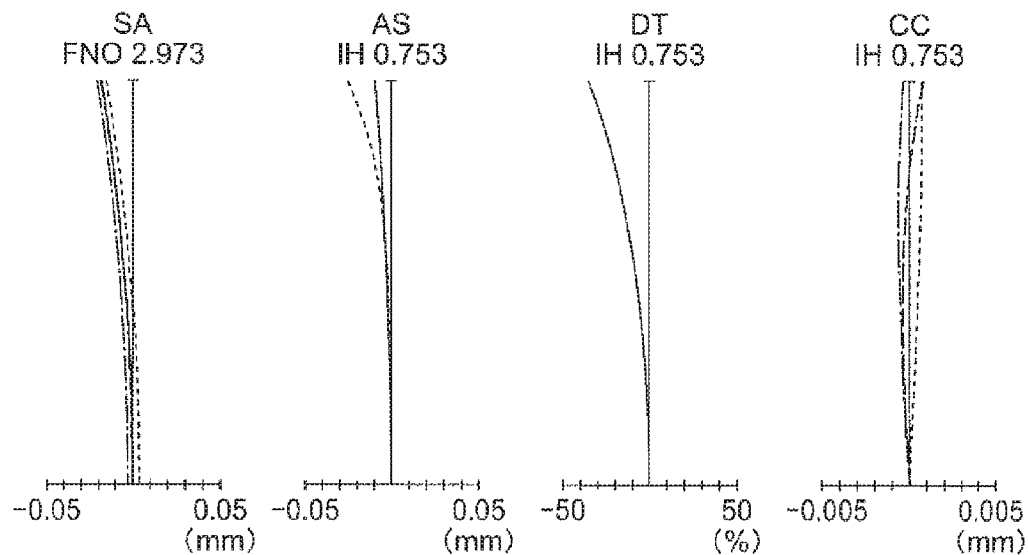
FIG. 25B, FIG. 25C, FIG. 25D, and FIG. 25E are aberration diagrams of the example 21.
Figure 27A:
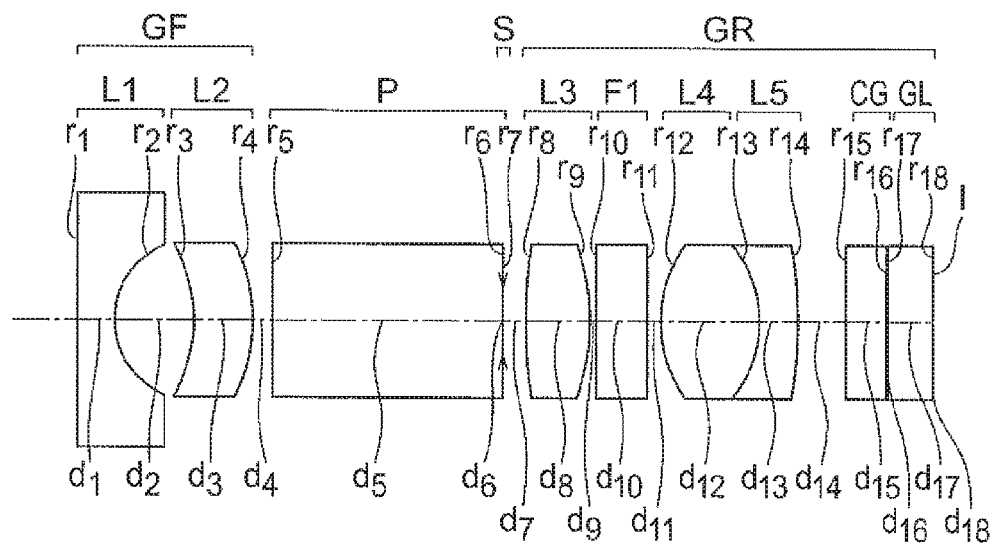
FIG. 27A is a diagram showing in cross-section, an arrangement of an oblique-viewing objective optical system according to an example 23.
Figures 27B, 27C, 27D, 27E:
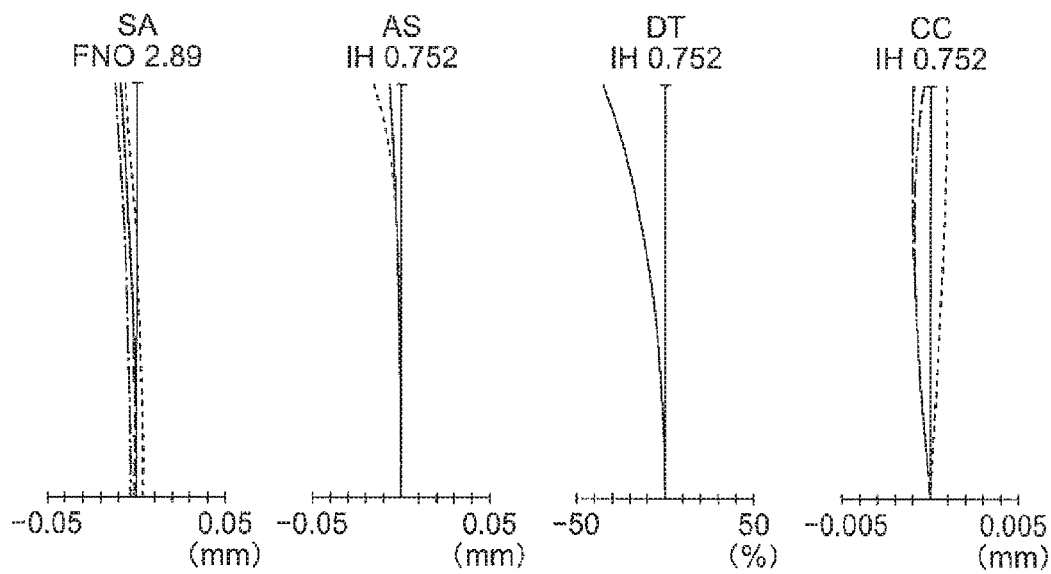
FIG. 27B, FIG. 27C, FIG. 27D, and FIG. 27E are aberration diagrams of the example 23
Figure 28A:
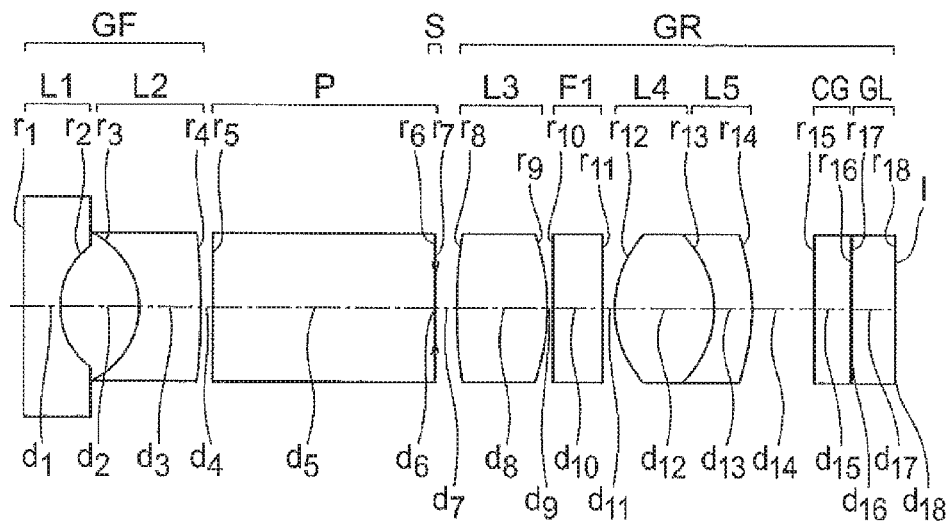
FIG. 28A is a diagram showing in cross-section, an arrangement of an oblique-viewing objective optical system according to an example 24.
Figures 28B, 28C, 28D, 28E:
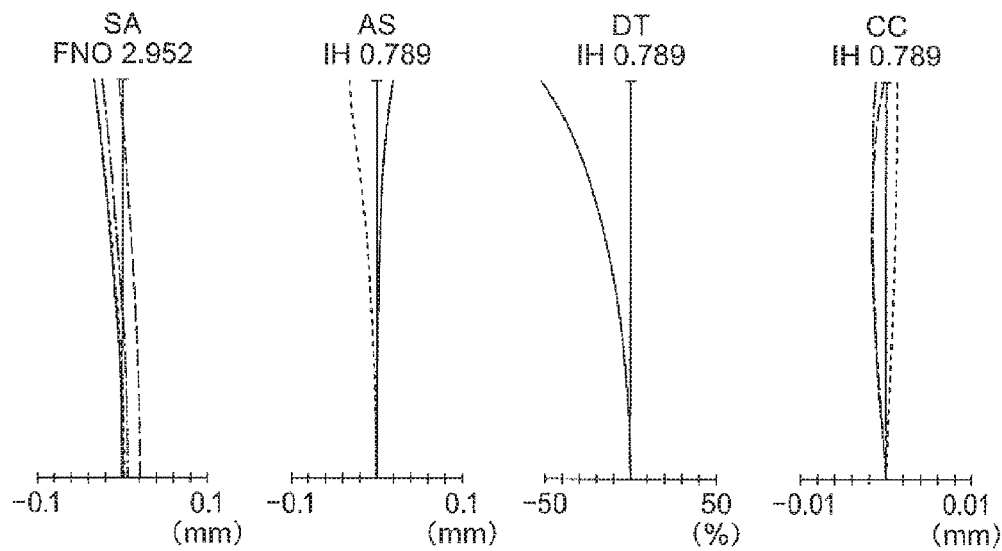
FIG. 28B, FIG. 28C, FIG. 28D, and FIG. 28E are aberration diagrams of the example 24.
Figure 29A:
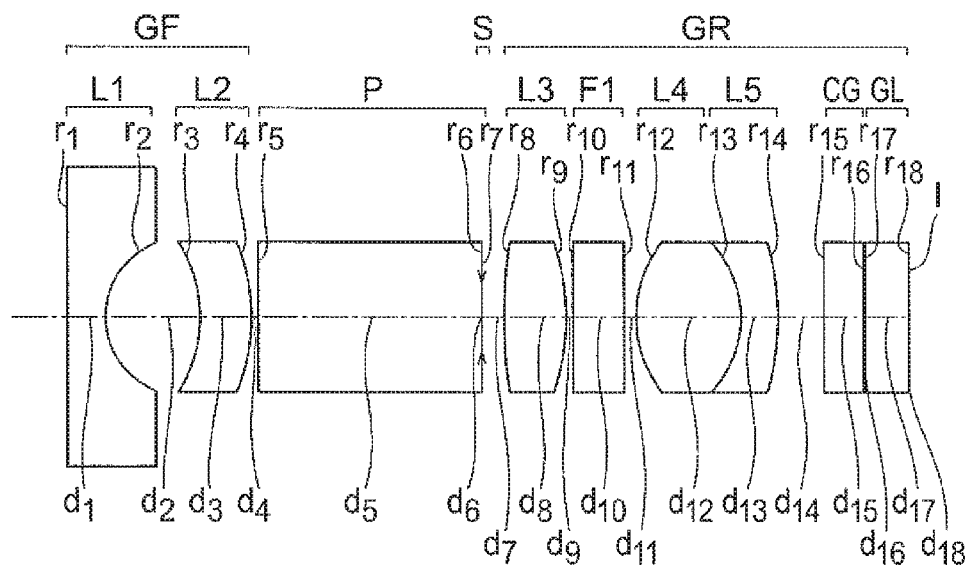
FIG. 29A is a diagram showing in cross-section, an arrangement of an oblique-viewing objective optical system according to an example 25.
Figures 29B, 29C, 29D, 29E:
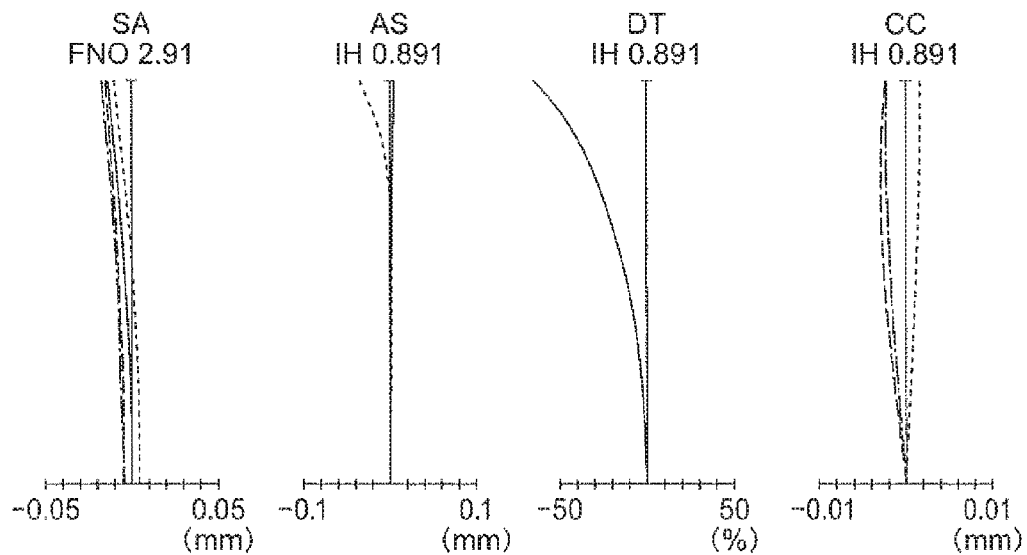
FIG. 29B, FIG. 29C, FIG. 29D, and FIG. 29E are aberration diagrams of the example 25.
Figure 30A:
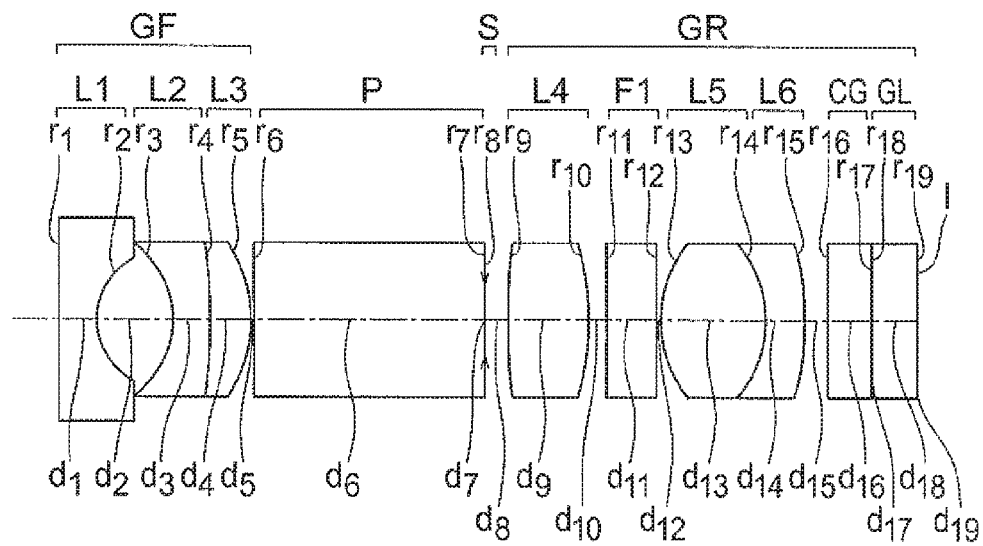
FIG. 30A is a diagram showing in cross-section, an arrangement of an oblique-viewing objective optical system according to an example 26.
Figures 30B, 30C, 30D, 30E:
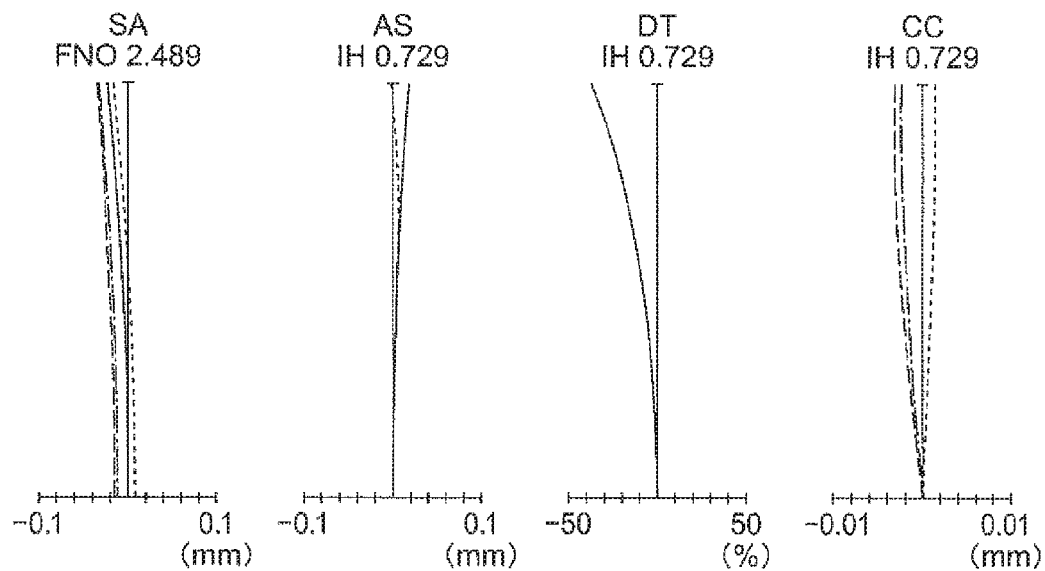
FIG. 30B, FIG. 30C, FIG. 30D, and FIG. 30E are aberration diagrams of the example 26.
Figure 31A:
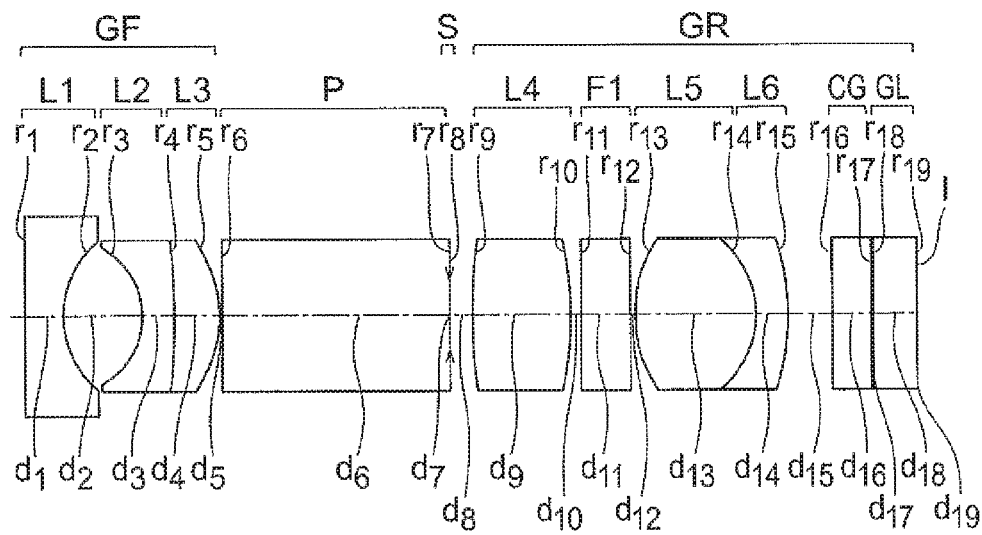
FIG. 31A is a diagram showing in cross-section, an arrangement of an oblique-viewing objective optical system according to an example 27.
Figures 31B, 31C, 31D, 31E:
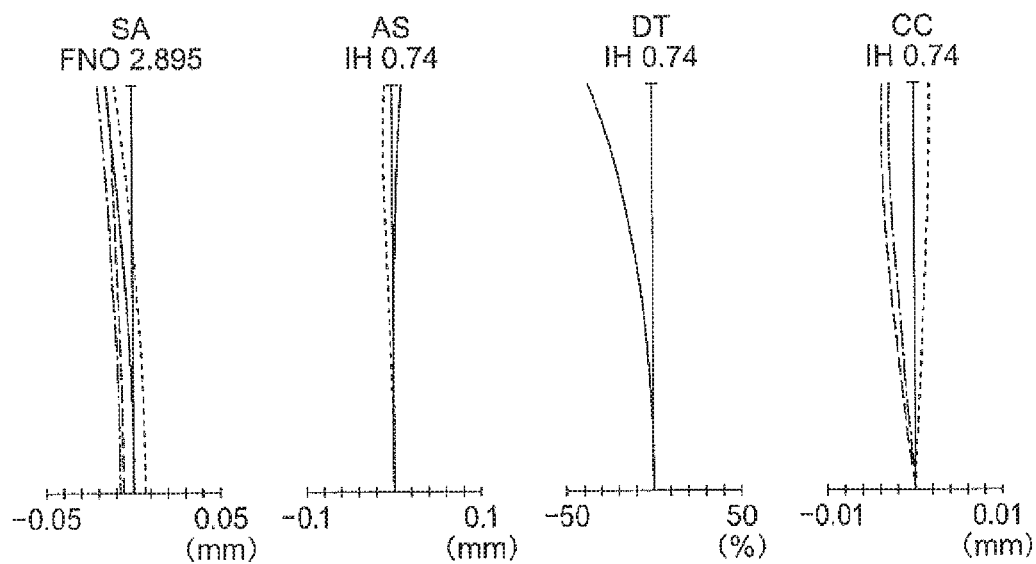
FIG. 31B, FIG. 31C, FIG. 31D, and FIG. 31E are aberration diagrams of the example 27.
Figure 32A:
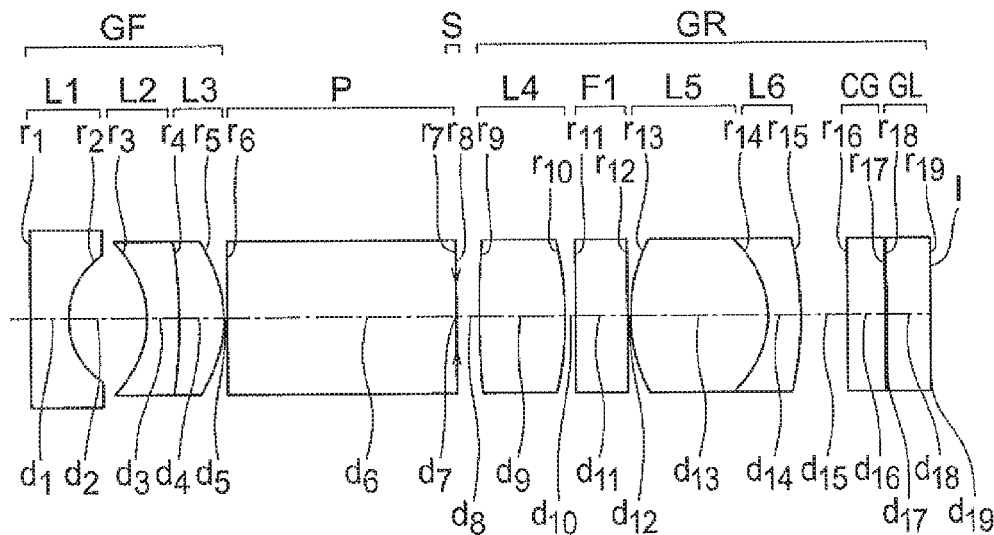
FIG. 32A is a diagram showing in cross-section, an arrangement of an oblique-viewing objective optical system according to an example 28.
Figures 32B, 32C, 32D, 32E:
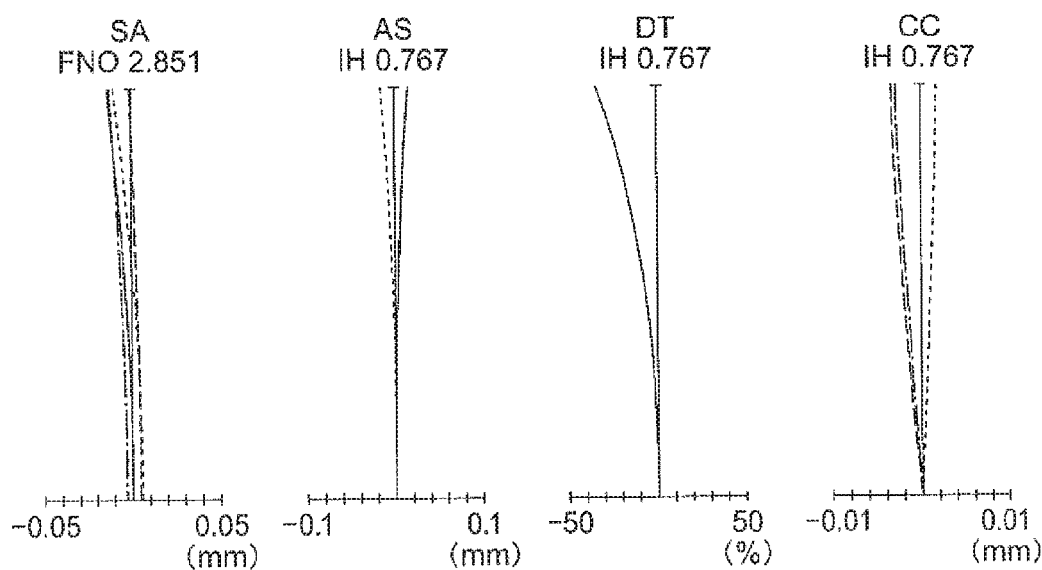
FIG. 32B, FIG. 32C, FIG. 32D, and FIG. 32E are aberration diagrams of the example 28.
Figure 33A:
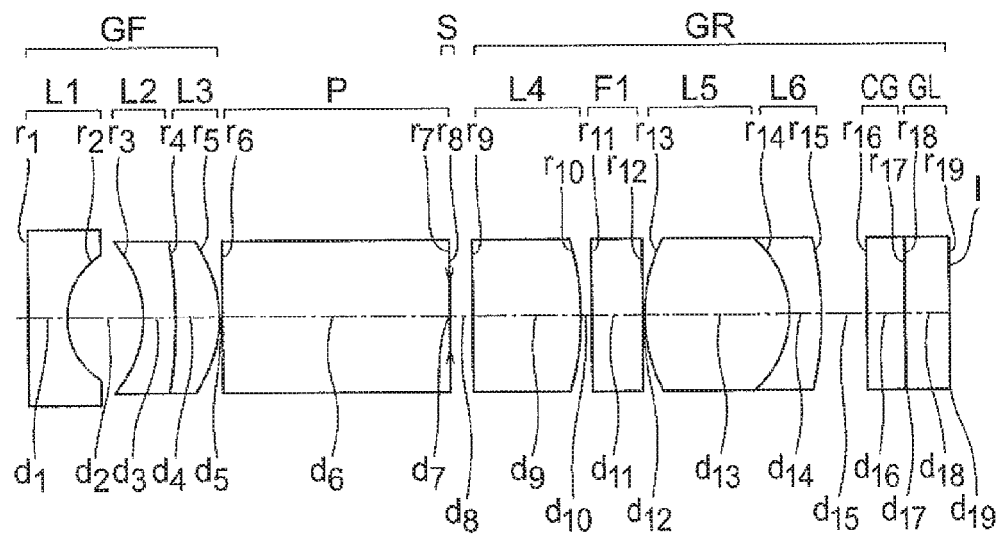
FIG. 33A is a diagram showing in cross-section, an arrangement of an oblique-viewing objective optical system according to an example 29.
Figures 33B, 33C, 33D, 33E:
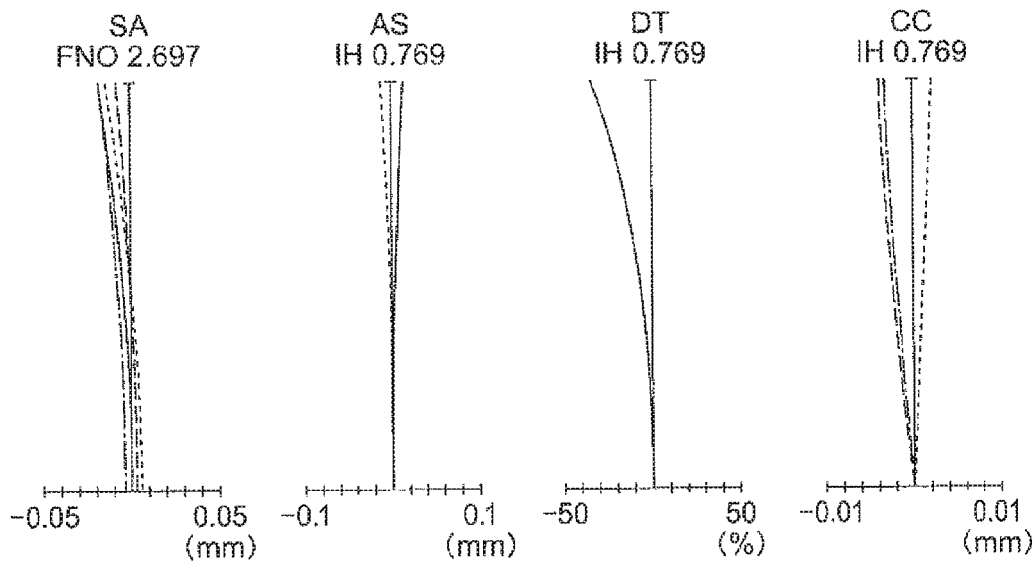
FIG. 33B, FIG. 33C, FIG. 33D, and FIG. 33E are aberration diagrams of the example 29.
Figure 34A:
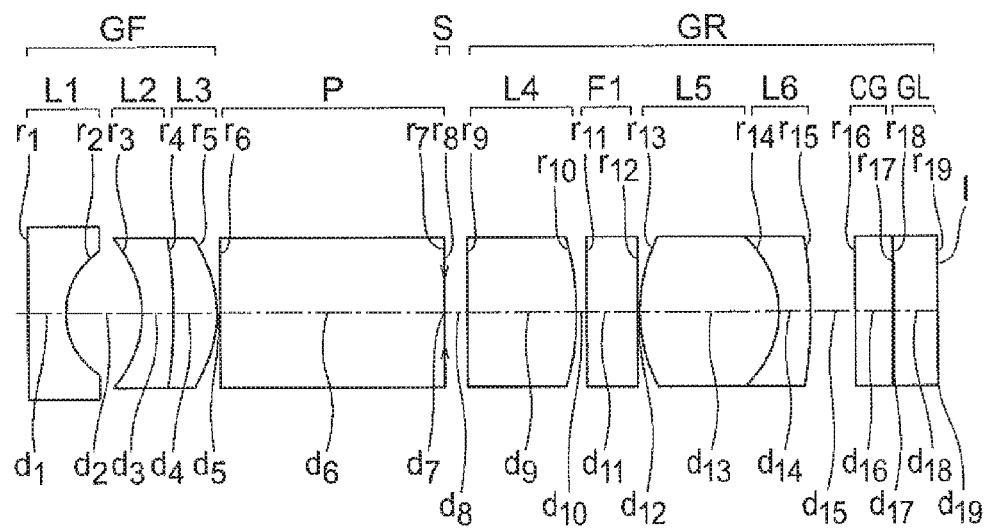
FIG. 34A is a diagram showing in cross-section, an arrangement of an oblique-viewing objective optical system according to an example 30.
Figures 34B, 34C, 34D, 34E:
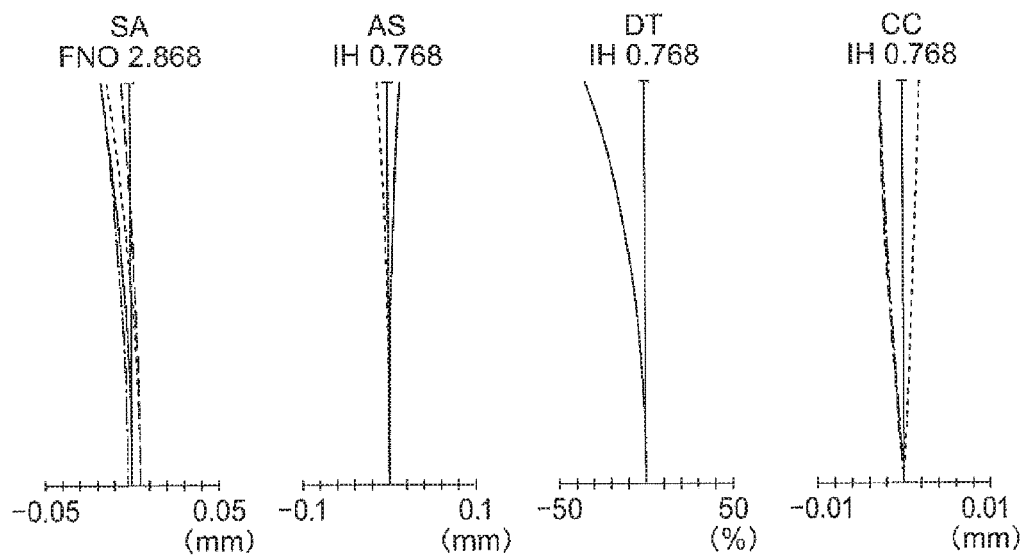
FIG. 34B, FIG. 34C, FIG. 34D, and FIG. 34E are aberration diagrams of the example 30.
Figure 35A:
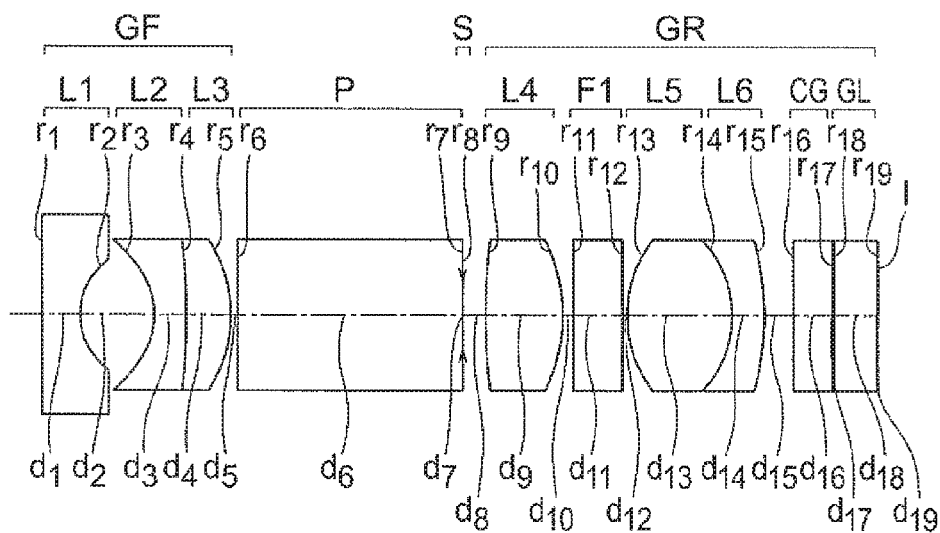
FIG. 35A is a diagram showing in cross-section, an arrangement of an oblique-viewing objective optical system according to an example 31.
Figures 35B, 35C, 35D, 35E:
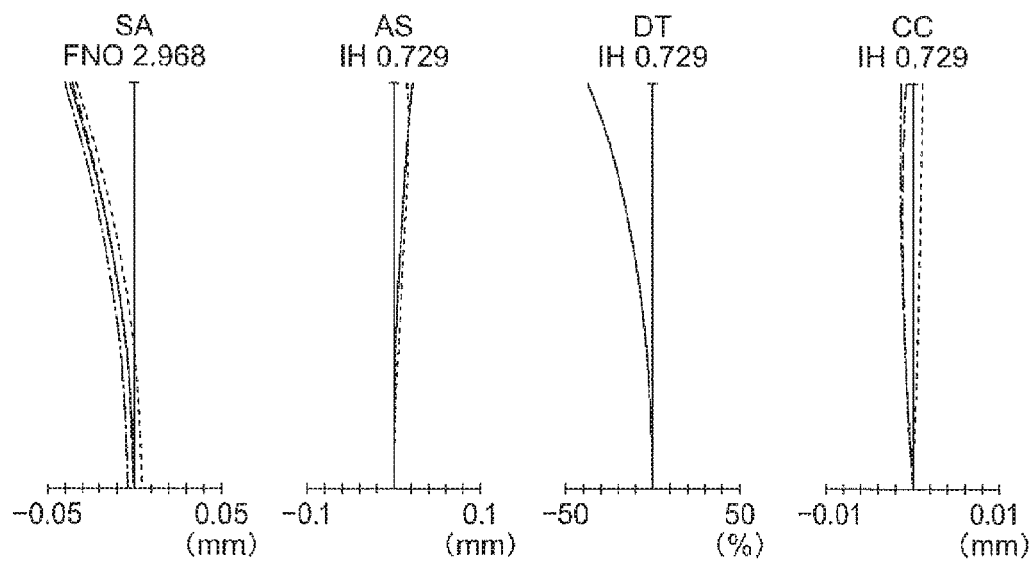
FIG. 35B, FIG. 35C, FIG. 35D, and FIG. 35E are aberration diagrams of the example 31.
Figure 36A:
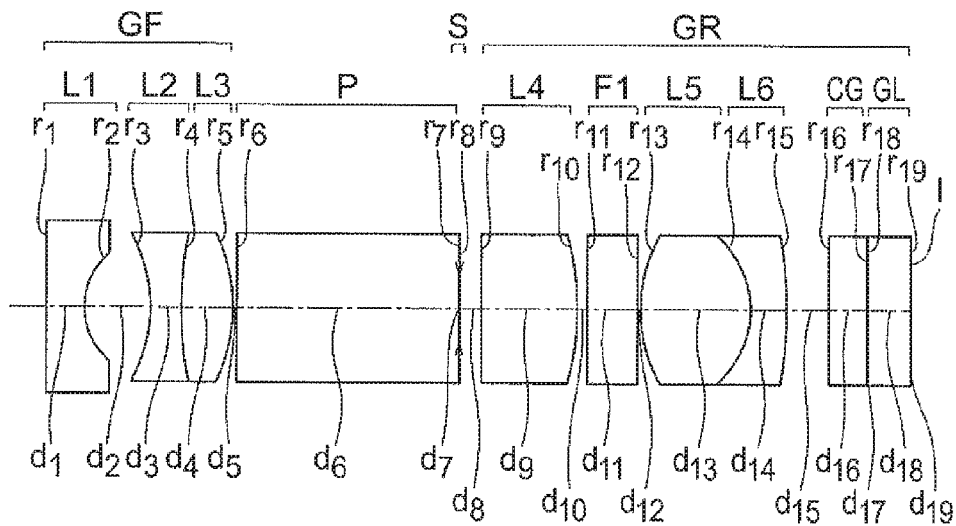
FIG. 36A is a diagram showing in cross-section, an arrangement of an oblique-viewing objective optical system according to an example 32.
Figures 36B, 36C, 36D, 36E:
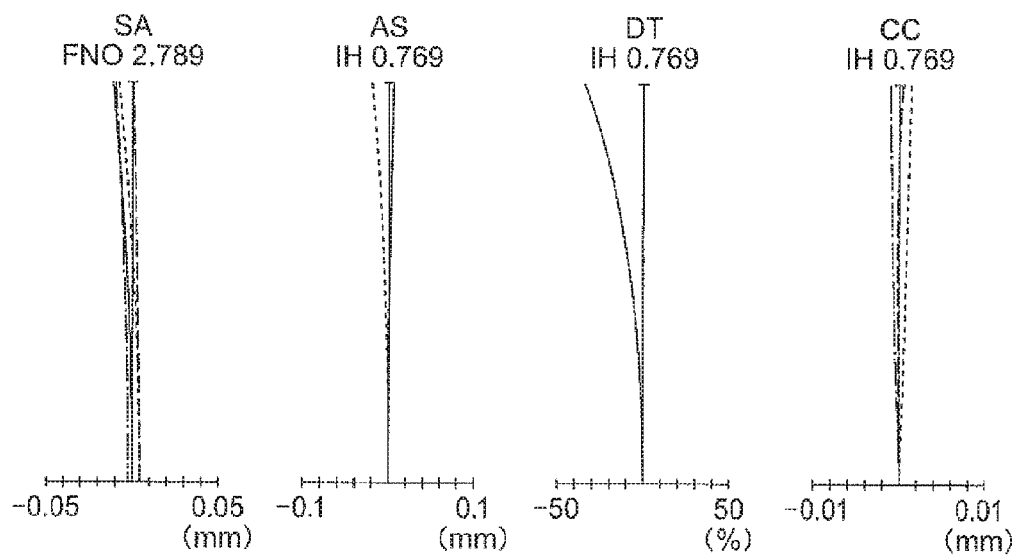
FIG. 36B, FIG. 36C, FIG. 36D, and FIG. 36E are aberration diagrams of the example 32.
Figure 37A:
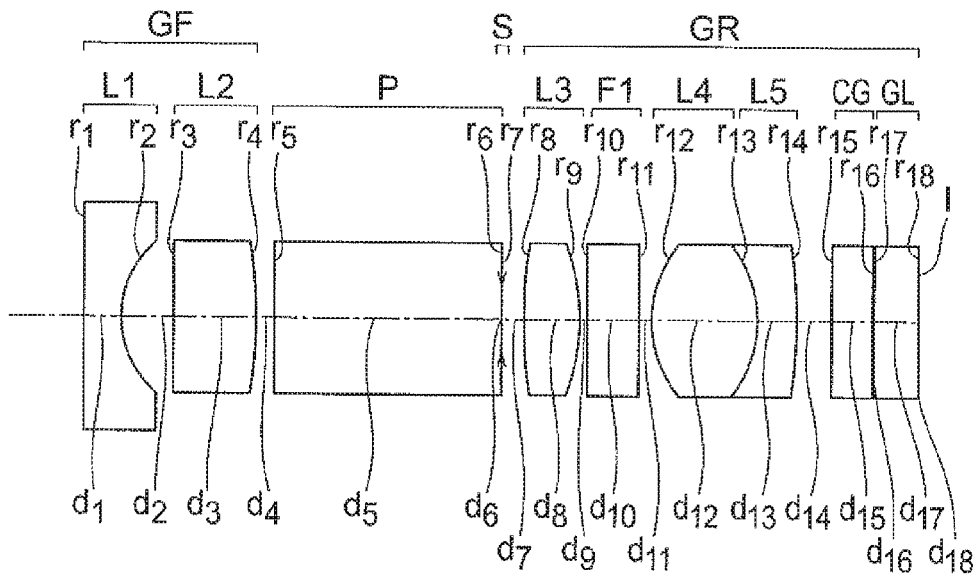
FIG. 37A is a diagram showing in cross-section, an arrangement of an oblique-viewing objective optical system according to an example 33.
Figures 37B, 37C, 37D, 37E:
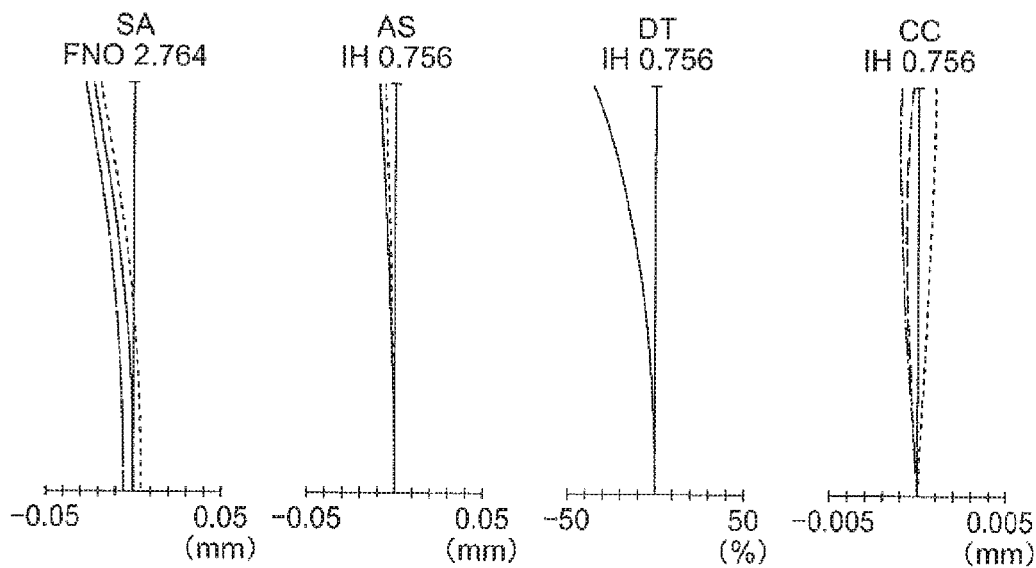
FIG. 37B, FIG. 37C, FIG. 37D, and FIG. 37E are aberration diagrams of the example 33.

Furthermore, it is also possible to form the prism P by a plurality of prisms. In FIG. 4C, an arrangement that enables side-viewing with two prisms has been shown, and in FIG. 4D, an arrangement that enables front-viewing with two prisms has been shown.

Moreover, by using a high refractive index glass material for the glass material of the prism P, it is possible to make an air-conversion length in prism short. When the air-conversion length in prism becomes short, since it is possible to suppress a height of a light ray at the front-side lens group from becoming high, small-sizing of a lens is possible. However, since the dispersion is large in the high refractive index glass material, the chromatic aberration due to prism is susceptible to occur. Therefore, it is necessary to suppress an increase in an amount of aberration in the overall optical system by correction by a lens.

On the other hand, in a case in which a low refractive index glass material is used for the glass material of the prism P, since the dispersion is small in the low refractive index glass material, the chromatic aberration due to prism is not susceptible to occur. However, since the air-conversion length in prism becomes long, the height of a light ray at the front-side lens group tends to become high. In this case, by disposing two lenses on the object side of the prism, it is possible to suppress the height of a light ray at the front-side lens group to be low. By making such arrangement, it is possible to suppress an increase in the lens outer diameter of the front-side lens group.

For making the oblique-viewing objective optical system an objective optical system having a high performance, the correction has to be carried out such that the chromatic aberration becomes extremely small. However, as mentioned above, the material of the prism is not restricted to a specific material. Therefore, even by using any glass material for the prism, an arrangement of an objective optical system having a small size and a high performance is possible.

A glass material of the first lens L1 may be let to be sapphire. Sapphire being a material having an extremely high degree of hardness is strong against external shock. Therefore, a lens surface on the object side cannot have a scratch easily. By using sapphire, projection of a scratch on an image or flare due to scratch are hard to occur.

A glass material for the first lens L1 is not restricted to sapphire. When a crystalline material having a high degree of hardness is used for the first lens L1, a surface of the lens cannot have a scratch easily.

In the rear-side lens group of the oblique-viewing objective optical system, two positive lenses are used. When a high refractive index glass material is used for the material of the positive lens, it is possible to make the radius of curvature of a lens surface large. In this case, it is possible to facilitate making the lens small-sized, while securing appropriately an edge thickness difference of the lens. However, since the dispersion is large for the high refractive index glass material, the chromatic aberration is susceptible to occur.

When a low refractive index glass material is used for the glass material of the positive lens, the radius of curvature of the positive lens becomes small. In this case, for securing an appropriate edge thickness difference, a center thickness of the positive lens is to be made large. However, when the center thickness is made too large, the length of lenses of the rear-side lens group becomes long. As a result, the space necessary for the focus adjustment becomes inadequate and it also makes the lens system large-sized.

As the pixel pitch of the image pickup element becomes extremely small, it is necessary to suppress the chromatic aberration to be extremely small. Consequently, although the refractive index becomes small, it is preferable to use a low-dispersion material which is advantageous for reducing the chromatic aberration instead of using a high refractive index glass material for the glass material of the positive lens.

For correcting the chromatic aberration adequately, it is preferable to use a glass material for which Abbe number is not less than 50 for example, for both of the glass material of the third lens L3 and the glass material of the fourth lens L4. Or, it is preferable to use a glass material for which Abbe number is not less than 60, for at least one of the glass material of the third lens L3 and the glass material of the fourth lens L4.

In such manner, it is extremely difficult to fulfil the high performance and small-sizing of the overall optical system in addition to the workability of the positive lens. However, in the oblique-viewing objective optical system of the present embodiment, by arranging the optical system most appropriately, an oblique-viewing objective optical system which has a remarkable workability, and in which the high performance and small-sizing are achieved is realized.

Moreover, when an absolute value of a radius of curvature of an object-side surface of the third lens L3 is made larger than an absolute value of an image-side surface of the third lens L3, aberration correction becomes easy.

Moreover, it is preferable to use a high-dispersion glass material having a refractive index not less than 1.9 and Abbe number not more than 25. By doing so, it is possible to correct the chromatic aberration favorably.

Moreover, by disposing the cemented lens CL at a position near the image plane, the height of a light ray passing through the cemented lens CL becomes high. By disposing the cemented lens CL at a position where the height of a light ray is high, it is possible to correct the chromatic aberration of magnification favorably. Thus, disposing the cemented lens CL at a position near the image surface is effective in correction of particularly the chromatic aberration of magnification.

Moreover, examples of the plane-parallel plate other than prism provided in the oblique-viewing objective optical system are infra-red ray cut filters or color temperature conversion filters. These filters are to be used for correcting sensitivity or correcting color of an image pickup element such as a CCD.

Moreover, a laser cut filter or a special function filter may be disposed in the oblique-viewing objective optical system. As a laser cut filter, filters for cutting laser light such as YAG laser and semiconductor laser are available. As a special function filter, a notch filter which cuts light rays of a specific wavelength region is available.

Moreover, for an optical filter, an absorbing filter, a reflecting filter, or a combination thereof may be used. Moreover, a filter to which an antireflection film is applied, may be used.

Moreover, a light transmitting surface of the prism may be provided with an interference film having an infrared light cut characteristic or a laser light cut characteristic.

Moreover, the plane-parallel plate filter disposed on the image-side surface of the oblique-viewing objective optical system of the present example is a cover glass CG and a glass lid GL used in an image pickup element. The image pickup element is to be fixed inside the frame member by holding aside surface and a front surface of the cover glass with the frame member. Moreover, an image plane I is a position of the light-receiving surface of the image pickup element.

Furthermore, by providing a filter F1 near the first lens L1, it is possible to make small a volume of an air layer formed on the image-side surface of the first lens L1. As a result, it is possible to reduce an effect of fogging due to dew formation on a lens surface.

Furthermore, the first lens L1 and the filter F1 may be cemented. Moreover, the first lens L1 and the filter F1 may be sealed by solder etc. to be air-tight. By doing so, it is possible to prevent occurrence of fogging more effectively.

Moreover, when a cemented lens is counted as one lens, the number of lenses in the oblique-viewing objective optical system is four. Although, the F-number for the oblique-viewing objective optical system is small, and the number of lenses is four which is small, an imaging performance is favorable.

Furthermore, in the oblique-viewing objective optical system, the lenses are disposed closely such that distances between lenses are the minimum. Therefore, it is possible to make the overall optical system small-sized.

Diagrams will be described below. In diagrams of examples 1 to 33, FIG. 5A, FIG. 6A, FIG. 7A, FIG. 8A, FIG. 9A, FIG. 10A, FIG. 11A, FIG. 12A, FIG. 13A, FIG. 14A, FIG. 15A, FIG. 16A, FIG. 17A, FIG. 18A, FIG. 19A, FIG. 20A, FIG. 21A, FIG. 22A, FIG. 23A, FIG. 24A, FIG. 25A, FIG. 26A, FIG. 27A, FIG. 28A, FIG. 29A, FIG. 30A, FIG. 31A, FIG. 32A, FIG. 33A, FIG. 34A, FIG. 35A, FIG. 36A, and FIG. 37A show a cross-sectional view of an oblique-viewing objective optical system. Moreover, P indicates a prism, F1 indicates a filter, CG indicates a cover glass, and GL indicates a glass lid.

Aberration diagrams will be described below. FIG. 5B, FIG. 6B, FIG. 7B, FIG. 8B, FIG. 9B, FIG. 10B, FIG. 11B, g. 12B, FIG. 13B, FIG. 14B, FIG. 15B, FIG. 16B, FIG. 17B, FIG. 18B, FIG. 19B, FIG. 20B, FIG. 21B, FIG. 22B, FIG. 23B, FIG. 24B, FIG. 25B, FIG. 26B, FIG. 27B, FIG. 28B, FIG. 29B, FIG. 30B, FIG. 31B, FIG. 32B, FIG. 33B, FIG. 34B, FIG. 35B, FIG. 36B, and FIG. 37B show a spherical aberration (SA).

FIG. 5C, FIG. 6C, FIG. 7C, FIG. 8C, FIG. 9C, FIG. 10C, FIG. 11C, FIG. 12C, FIG. 13C, FIG. 14C, FIG. 15C, FIG. 16C, FIG. 17C, FIG. 18C, FIG. 19C, FIG. 20C, FIG. 21C, FIG. 22C, FIG. 23C, FIG. 24C, FIG. 25C, FIG. 26C, FIG. 27C, FIG. 28C, FIG. 29C, FIG. 30C, FIG. 31C, FIG. 32C, FIG. 33C, FIG. 34C, FIG. 35C, FIG. 36C, and FIG. 37C show an astigmatism (AS).

FIG. 5D, FIG. 6D, FIG. 7D, FIG. 8D, FIG. 9D, FIG. 10D, FIG. 11D, FIG. 12D, FIG. 13D, FIG. 14D, FIG. 15D, FIG. 16D, FIG. 17D, FIG. 18D, FIG. 19D, FIG. 20D, FIG. 21D, FIG. 22D, FIG. 23D, FIG. 24D, FIG. 25D, FIG. 26D, FIG. 27D, FIG. 28D, FIG. 29D, FIG. 30D, FIG. 31D, FIG. 32D, FIG. 33D, FIG. 34D, FIG. 35D, FIG. 36D, and FIG. 37D show a distortion (DT).

FIG. 5E, FIG. 6E, FIG. 7E, FIG. 8E, FIG. 9E, FIG. 10E, FIG. 11E, FIG. 12E, FIG. 13E, FIG. 14E, FIG. 15E, FIG. 16E, FIG. 17E, FIG. 18E, FIG. 19E, FIG. 20E, FIG. 21E, FIG. 22E, FIG. 23E, FIG. 24E, FIG. 25E, FIG. 26E, FIG. 27E, FIG. 28E, FIG. 29E, FIG. 30E, FIG. 31E, FIG. 32E, FIG. 33E, FIG. 34E, FIG. 35E, FIG. 36E, and FIG. 37E show a chromatic aberration of magnification (CC).

In each aberration diagram, a horizontal axis indicates an amount of aberration. For spherical aberration, astigmatism, and chromatic aberration of magnification, the unit of amount of aberration is mm. Moreover, for distortion, the unit of amount of aberration is %. Moreover, IH denotes an image height and unit thereof is mm, and Fno denotes an F-number. Furthermore, the unit of a wavelength of aberration curve is nm.

Examples will be described below.

Example 1

An oblique-viewing objective optical system according to an example 1 will be described below. The oblique-viewing objective optical system of the example 1 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side. The comparison of the magnitude of the radius of curvature of a lens is made by absolute values. Similar is a case for examples 2 to 33.

A filter F1, a cover glass CG, and a glass lid GL are disposed in the rear-side lens group GR. The filter F1 is disposed between the biconvex positive lens L3 and the cemented lens.

Data of glass materials used for lenses, prism, and cover glass is shown below. Significance of parameters is as follows. Moreover, |≤1.9| indicates that it is not less than 1.9. Similar is a case for examples 2 to 33.

nd: refractive index for d-line
vd: Abbe number
HRI: high refractive index glass material
LRI: low refractive index glass material
HD: high-dispersion glass material
LD: low-dispersion glass material
HRI-HD: high refractive index, high-dispersion glass material
HRI-LD: high refractive index, low-dispersion glass material
LRI-LD: low refractive index, low-dispersion glass material

|  | nd | vd |  |
|---|---|---|---|
| lens L1 | 1.88 |  | HRI |
| lens L2 | 1.62 | 35 |  |
| prism | 1.88 |  | HRI |
| lens L3 | 1.62 | 53 |  |
| lens L4 | 1.51 | 64 | LD |
| lens L5 | ≤1.9 | 18 | HRI-HD |
| cover glass CG | 1.88 |  | HRI |

In the example 1, a full angle of view is 100 degrees.

Example 2

An oblique-viewing objective optical system according to an example 2 will be described below. The oblique-viewing objective optical system of the example 2 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
|---|---|---|---|
| lens L1 | 1.88 |  | HRI |
| lens L2 | 1.58 | 40 |  |
| prism | 1.76 | 71 | HRI-LD |
| lens L3 | 1.58 | 61 | LD |
| lens L4 | 1.51 | 64 | LD |
| lens L5 | ≤1.9 | 18 | HRI-HD |
| cover glass CG | 1.88 |  | HRI |

In the example 2, a full angle of view is 100 degrees.

Example 3

An oblique-viewing objective optical system according to an example 3 will be described below. The oblique-viewing objective optical system of the example 3 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
|---|---|---|---|
| lens L1 | 1.88 |  | HRI |
| lens L2 | 1.58 | 40 |  |
| prism | 1.51 | 64 | LD |
| lens L3 | 1.58 | 61 | LD |
| lens L4 | 1.51 | 64 | LD |
| lens L5 | ≤1.9 | 18 | HRI-HD |
| cover glass CG | 1.88 |  | HRI |

In the example 3, a full angle of view is 100 degrees.

An oblique-viewing objective optical system according to an example 4 will be described below. The oblique-viewing objective optical system of the example 4 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.88 |  | HRI |
| lens L2 | 1.74 | 27 |  |
| prism | 1.51 | 64 | LD |
| lens L3 | 1.51 | 64 | LD |
| lens L4 | 1.48 | 70 | LD |
| lens L5 | ≤1.9 | 18 | HRI-HD |
| cover glass CG | 1.88 |  | HRI |

In the example 4, a full angle of view is 100 degrees.

Example 4

An oblique-viewing objective optical system according to an example 5 will be described below. The oblique-viewing objective optical system of the example 5 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.88 |  | HRI |
| lens L2 | 1.74 | 27 |  |
| prism | 1.51 | 64 | LD |
| lens L3 | 1.58 | 61 | LD |
| lens L4 | 1.51 | 64 | LD |
| lens L5 | ≤1.9 | 18 | HRI-HD |
| cover glass CG | 1.51 |  | LRI |

In the example 5, a full angle of view is 100 degrees.

Example 6

An oblique-viewing objective optical system according to an example 6 will be described below. The oblique-viewing objective optical system of the example 6 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a biconvex positive lens L2.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.88 |  | HRI |
| lens L2 | 1.74 | 27 |  |
| prism | 1.51 | 64 | LD |
| lens L3 | 1.61 | 54 | LD |
| lens L4 | 1.51 | 64 | LD |
| lens L5 | ≤1.9 | 18 | HRI-HD |
| cover glass CG | 1.51 |  | LRI |

In the example 6, a full angle of view is 100 degrees.

Example 7

An oblique-viewing objective optical system according to an example 7 will be described below. The oblique-viewing objective optical system of the example 7 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
|---|---|---|---|
| lens L1 | 1.88 |  | HRI |
| lens L2 | 1.74 | 27 |  |
| prism | 1.51 | 64 | LD |
| lens L3 | 1.61 | 54 | LD |
| lens L4 | 1.51 | 64 | LD |
| lens L5 | ≤1.9 | 18 | HRI-HD |
| cover glass CG | 1.51 |  | LRI |

In the example 7, a full angle of view is 100 degrees.

Example 8

An oblique-viewing objective optical system according to an example 8 will be described below. The oblique-viewing objective optical system of the example 8 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
|---|---|---|---|
| lens L1 | 1.88 |  | HRI |
| lens L2 | 1.74 | 27 |  |
| prism | 1.8 | 40 | HRI |
| lens L3 | 1.61 | 54 | LD |
| lens L4 | 1.51 | 64 | LD |
| lens L5 | ≤1.9 | 18 | HRI-HD |
| cover glass CG | 1.51 |  | LRI |

In the example 8, a full angle of view is 100 degrees.

Example 9

An oblique-viewing objective optical system according to an example 9 will be described below. The oblique-viewing objective optical system of the example 9 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens. By using a high refractive index glass material for the cover glass, it is possible to arrange the oblique-viewing objective optical system without narrowing the space necessary for focus adjustment.

|  | nd | vd |  |
|---|---|---|---|
| lens L1 | 1.88 |  | HRI |
| lens L2 | 1.74 | 27 |  |
| prism | 1.88 | 40 | HRI |
| lens L3 | 1.61 | 54 | LD |
| lens L4 | 1.51 | 64 | LD |
| lens L5 | ≤1.9 | 18 | HRI-HD |
| cover glass CG | 1.88 |  | HRI |

In the example 9, a full angle of view is 100 degrees.

Example 10

An oblique-viewing objective optical system according to an example 10 will be described below. The oblique-viewing objective optical system of the example 10 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|   | nd | vd |   |
|---|---|---|---|
| lens L1 | 1.88 |  | HRI |
| lens L2 | 1.74 | 41 |  |
| prism | 1.51 | 64 | LRI |
| lens L3 | 1.62 | 53 | LD |
| lens L4 | 1.75 | 52 | LD |
| lens L5 | ≤1.9 | 18 | HRI-HD |
| cover glass CG | 1.51 |  | LRI |

In the example 10, a full angle of view is 120 degrees. Compared to the example 1 for example, the angle of view is wider in the example 10.

Example 11

An oblique-viewing objective optical system according to an example 11 will be described below. The oblique-viewing objective optical system of the example 11 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L5, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group G. The filter F1 is disposed between the biconvex positive lens L3 and the cemented lens.

|   | nd | vd |   |
|---|---|---|---|
| lens L1 | 1.88 |  | HRI |
| lens L2 | 1.7 | 41 |  |
| prism | 1.51 | 64 | LRI |
| lens L3 | 1.62 | 53 | LD |
| lens L4 | 1.75 | 52 | LD |
| lens L5 | ≤1.9 | 18 | HRI-HD |
| cover glass CG | 1.51 |  | LRI |

In the example 11, an angle of view is 140 degrees. The lens arrangement of the example 11 is similar to the lens arrangement of the example 10, but compared to the example 10, the angle of view is wider in the example 11.

Example 12

An oblique-viewing objective optical system according to an example 12 will be described below. The oblique-viewing objective optical system of the example 12 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a positive meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, the biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|   | nd | vd |   |
|---|---|---|---|
| lens L1 | 1.88 |  | HRI |
| lens L2 | 1.7 | 41 |  |
| prism | 1.8 | 40 | HRI |
| lens L3 | 1.62 | 53 | LD |
| lens L4 | 1.75 | 52 | LD |
| lens L5 | ≤1.9 | 18 | HRI-HD |
| cover glass CG | 1.88 |  | HRI |

In the example 12, an angle of view is 140 degrees. A lens arrangement of the example 12 is similar to the lens arrangement of the example 10, but compared to the example 10, the angle of view is wider in the example 12.

Example 13

An oblique-viewing objective optical system according to an example 13 will be described below. The oblique-viewing objective optical system of the example 13 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a positive refractive power is formed by the negative meniscus lens L2 and the positive meniscus lens L3.

A crystalline material made of sapphire is used for the planoconcave negative lens L1. Sapphire being hard, a lens surface doesn't get a scratch easily, and also being strong against external impact, is not cracked easily.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
| --- | --- | --- | --- |
| lens L1 | 1.76 |  | HRI |
| lens L2 | 1.58 | 61 |  |
| lens L3 | 1.53 | 48 |  |
| prism | 1.88 | 40 | HRI |
| lens L4 | 1.58 | 61 | LD |
| lens L5 | 1.72 | 54 | LD |
| lens L6 | ≦1.9 | 18 | HRI-HD |
| cover glass CG | 1.88 |  | HRI |

In the example 13, a full angle of view is 100 degrees.

Example 14

An oblique-viewing objective optical system according to an example 14 will be described below. The oblique-viewing objective optical system of the example 14 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a positive refractive power is formed by the negative meniscus lens L2 and the positive meniscus lens L3.

A crystalline material made of sapphire is used for the planoconcave negative lens L1. Sapphire being hard, a lens surface doesn't get a scratch easily, and also being strong against external impact, is not cracked easily.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
| --- | --- | --- | --- |
| lens L1 | 1.76 |  | HRI |
| lens L2 | 1.58 | 61 |  |
| lens L3 | 1.53 | 48 |  |
| prism | 1.8 | 40 | HRI |
| lens L4 | 1.72 | 54 | LD |
| lens L5 | 1.72 | 54 | LD |
| lens L6 | ≦1.9 | 18 | HRI-HD |
| cover glass CG | 1.88 |  | HRI |

In the example 14, a full angle of view is 100 degrees.

Example 15

An oblique-viewing objective optical system according to an example 15 will be described below. The oblique-viewing objective optical system of the example 15 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a positive refractive power is formed by the negative meniscus lens L2 and the positive meniscus lens L3.

The optical-patch converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.53 | 48 |  |
| prism | 1.8 | 40 | HRI |
| lens L4 | 1.74 | 49 |  |
| lens L5 | 1.72 | 54 | LD |
| lens L6 | ≤1.9 | 18 | HRI-HD |
| cover glass CG | 1.88 |  | HRI |

In the example 15, a full angle of view is 100 degrees.

Example 16

An oblique-viewing objective optical system according to an example 16 will be described below. The oblique-viewing objective optical system of the example 16 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a biconcave negative lens L2, and a biconvex positive lens L3. Here, a cemented lens having a positive refractive power is formed by the biconcave negative lens L2 and the biconvex positive lens L3.

A crystalline material made of sapphire is used for the planoconcave negative lens L1. Sapphire being hard, a lens surface doesn't get a scratch easily, and also being strong against external impact, is not cracked easily.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.58 | 40 |  |
| prism | 1.88 | 40 | HRI |
| lens L4 | 1.71 | 47 | HRI |
| lens L5 | 1.72 | 54 | LD |
| lens L6 | ≤1.9 | 18 | HRI-HD |
| cover glass CG | 1.88 |  | HRI |

In the example 16, a full angle of view is 100 degrees.

Example 17

An oblique-viewing objective optical system according to an example 17 will be described below. The oblique-viewing objective optical system of the example 17 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a positive refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.54 | 45 |  |
| prism | 1.8 | 40 | HRI |
| lens L4 | 1.58 | 61 | LD |
| lens L5 | 1.75 | 52 | HRI |
| lens L6 | ≤1.9 | 18 | HRI-HD |
| cover glass CG | 1.88 |  | HRI |

In the example 17, a full angle of view is 120 degrees. Compared to the example 13 for instance, the angle of view is wider in the example 17.

Example 18

An oblique-viewing objective optical system according to an example 18 will be described below. The oblique-viewing objective optical system of the example 18 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a positive refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
| --- | --- | --- | --- |
| lens L1 | 1.88 |  | HRI |
| lens L2 | 1.58 | 61 |  |
| lens L3 | 1.54 | 45 |  |
| prism | 1.8 | 40 | HRI |
| lens L4 | 1.58 | 61 | LD |
| lens L5 | 1.75 | 52 | HRI |
| lens L6 | ≤1.9 | 18 | HRI-HD |
| cover glass CG | 1.88 |  | HRI |

In the example 18, an angle of view is 140 degrees. The lens arrangement of the example 18 and the lens arrangement of the example 17 are similar, but compared to the example 17, the angle of view is wider in the example 18.

Example 19

An oblique-viewing objective optical system according to an example 19 will be described below. The oblique-viewing objective optical system of the example 19 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a biconcave negative lens L2, and a biconvex positive lens L3. Here, a cemented lens having a positive refractive power is formed by the biconcave negative lens L2 and the biconvex positive lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
| --- | --- | --- | --- |
| lens L1 | 1.88 |  | HRI |
| lens L2 | 1.58 | 61 |  |
| lens L3 | 1.54 | 45 |  |
| prism | 1.88 | 40 | HRI |
| lens L4 | 1.58 | 61 | LD |
| lens L5 | 1.75 | 52 | HRI |
| lens L6 | ≤1.9 | 18 | HRI-HD |
| cover glass CG | 1.88 |  | HRI |

In the example 19, a full angle of view is 150 degrees. Compared to the example 18, the angle of view is wider in the example 19.

Example 20

An oblique-viewing objective optical system according to an example 20 will be described below. The oblique-viewing objective optical system of the example 20 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.48 | 70 | LRI-LD |
| prism | 1.88 | 40 | HRI |
| lens L3 | 1.53 | 59 | LD |
| lens L4 | 1.51 | 64 | LD |
| lens L5 | ≤1.9 | 18 | HRI-HD |
| cover glass CG | 1.88 |  | HRI |

In the example 20, a full angle of view is 100 degrees.

Example 21

An oblique-viewing objective optical system according to an example 21 will be described below. The oblique-viewing objective optical system of the example 21 includes in order form an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.48 | 70 | LRI-LD |
| prism | 1.51 | 64 | LRI-LD |
| lens L3 | 1.51 | 64 | LD |
| lens L4 | 1.51 | 64 | LD |
| lens L5 | ≤1.9 | 18 | HRI-HD |
| cover glass CG | 1.88 |  | HRI |

In the example 21, a full angle of view is 100 degrees.

Example 22

An oblique-viewing objective optical system according to an example 22 will be described below. The oblique-viewing objective optical system of the example 22 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.51 | 64 | LRI-LD |
| prism | 1.51 | 64 | LRI-LD |
| lens L3 | 1.58 | 61 | LD |
| lens L4 | 1.51 | 64 | LD |
| lens L5 | ≤1.9 | 18 | HRI-HD |
| cover glass CG | 1.51 | 64 | LRI |

In the example 22, a full angle of view is 100 degrees.

Example 23

An oblique-viewing objective optical system according to an example 23 will be described below. The oblique-viewing objective optical system of the example 23 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in a rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.51 | 64 | LRI-LD |
| prism | 1.51 | 64 | LRI-LD |
| lens L3 | 1.62 | 58 | LD |
| lens L4 | 1.51 | 64 | LD |
| lens L5 | ≤1.9 | 18 | HRI-HD |
| cover glass CG | 1.51 | 64 | LRI |

In the example 23, a full angle of view is 100 degrees.

Example 24

An oblique-viewing objective optical system according to an example 24 will be described below. The oblique-viewing objective optical system of the example 24 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.48 | 70 | LRI-LD |
| prism | 1.51 | 64 | LRI-LD |
| lens L3 | 1.56 | 60 | LD |
| lens L4 | 1.51 | 64 | LD |
| lens L5 | ≤1.9 | 18 | HRI-HD |
| cover glass CG | 1.88 | 40 | HRI |

In the example 24, a full angle of view is 119.6 degrees. Compared to the example 20 for instance, the angle of view is wider in the example 24.

Example 25

An oblique-viewing objective optical system according to an example 25 will be described below. The oblique-viewing objective optical system of the example 25 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a negative meniscus lens L2 having a convex surface directed toward an image-plane side.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.51 | 64 | LRI-LD |
| lens L2 | 1.51 | 64 | LRI-LD |
| prism | 1.51 | 64 | LRI-LD |
| lens L3 | 1.62 | 58 | LD |
| lens L4 | 1.54 | 59 | LD |
| lens L5 | ≤1.9 | 18 | HRI-HD |
| cover glass CG | 1.51 | 64 | LRI |

In the example 25, a full angle of view is 140 degrees. Compared to the example 24, the angle of view is wider in the example 25.

Example 26

An oblique-viewing objective optical system according to an example 26 will be described below. The oblique-viewing objective optical system of the example 26 includes in order from an object side, a front-side lens group GF having a negative refractive power, an optical path converting element P, an aperture stop S, and a rear-side lens group GR having a positive refractive power.

The front-side lens group GF includes a biconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.51 |  | LRI |
| lens L2 | 1.58 | 61 |  |
| lens L3 | 1.53 | 48 |  |
| prism | 1.51 | 64 | LRI-LD |
| lens L4 | 1.72 | 54 | HRI-LD |
| lens L5 | 1.58 | 61 | LD |
| lens L6 | ≤1.9 | 18 | HRI-HD |
| cover glass CG | 1.51 |  | LRI |

In the example 26, a full angle of view is 100 degrees.

Example 27

An oblique-viewing objective optical system according to an example 27 will be described below. The oblique-viewing objective optical system of the example 27 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.53 | 48 |  |
| prism | 1.51 | 64 | LRI-LD |
| lens L4 | 1.72 | 54 | HRI-LD |

-continued

|  | nd | vd |  |
|---|---|---|---|
| lens L5 | 1.58 | 61 | LD |
| lens L6 | ≤1.9 | 18 | HRI-HD |
| cover glass CG | 1.51 |  | LRI |

In the example 27, a full angle of view is 100 degrees.

Example 28

An oblique-viewing objective optical system according to an example 28 will be described below. The oblique-viewing objective optical system of the example 28 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.53 | 48 |  |
| prism | 1.51 | 64 | LRI-LD |
| lens L4 | 1.72 | 54 | HRI-LD |
| lens L5 | 1.72 | 54 | LD |
| lens L6 | ≤1.9 | 18 | HRI-HD |
| cover glass CG | 1.51 |  | LRI |

In the example 28, a full angle of view is 100 degrees.

Example 29

An oblique-viewing objective optical system according to an example 29 will be described below. The oblique-viewing objective optical system of the example 29 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.53 | 48 |  |
| prism | 1.51 | 64 | LRI-LD |
| lens L4 | 1.72 | 54 | HRI-LD |
| lens L5 | 1.75 | 52 | HRI-LD |
| lens L6 | ≤1.9 | 18 | HRI-HD |
| cover glass CG | 1.88 |  | HRI |

In the example 29, a full angle of view is 100 degrees.

Example 30

An oblique-viewing objective optical system according to an example 30 will be described below. The oblique-viewing objective optical system of the example 30 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical-patch converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
|---|---|---|---|
| lens L1 | 1.88 |  | HRI |
| lens L2 | 1.58 | 61 |  |
| lens L3 | 1.53 | 48 |  |
| prism | 1.8 | 40 | HRI |
| lens L4 | 1.72 | 54 | HRI-LD |
| lens L5 | 1.75 | 52 | LD |
| lens L6 | ≤1.9 | 18 | HRI-HD |
| cover glass CG | 1.88 |  | HRI |

In the example 30, a full angle of view is 100 degrees.

Example 31

An oblique-viewing objective optical system according to an example 31 will be described below. The oblique-viewing objective optical system of the example 31 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a negative meniscus lens L2 having a convex surface directed toward an image-plane side, and a positive meniscus lens L3 having a convex surface directed toward the image-plane side. Here, a cemented lens having a negative refractive power is formed by the negative meniscus lens L2 and the positive meniscus lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and the glass lid GL are disposed in the rear-side lens group GR. The filter F1 is disposed between the biconvex positive lens L4 and the cemented lens.

|  | nd | vd |  |
|---|---|---|---|
| lens L1 | 1.51 | 64 | LRI-LD |
| lens L2 | 1.58 | 61 |  |

|  | nd | vd |  |
| --- | --- | --- | --- |
| lens L3 | 1.53 | 48 |  |
| prism | 1.51 | 64 | LRI-LD |
| lens L4 | 1.48 | 70 | LD |
| lens L5 | 1.58 | 61 | LD |
| lens L6 | ≤1.9 | 18 | HRI-HD |
| cover glass CG | 1.51 |  | LRI |

In the example 31, a full angle of view is 100 degrees.

Example 32

An oblique-viewing objective optical system according to an example 32 will be described below. The oblique-viewing objective optical system of the example 32 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, a biconcave negative lens L2, and a biconvex positive lens L3. Here, a cemented lens having a negative refractive power is formed by the biconcave negative lens L2 and the biconvex positive lens L3.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L4, a biconvex positive lens L5, and a negative meniscus lens L6 having a convex surface directed toward an image side. Here, a cemented lens having a positive refractive power is formed by the biconvex positive lens L5 and the negative meniscus lens L6. A surface having a smaller radius of curvature of the biconvex positive lens L4 is directed toward the image-plane side.

A filter F1, a cover glass CG, and a glass lid GL are disposed in the rear-side lens group GR. The filter F1 is disposed between the biconvex positive lens L4 and the cemented lens.

|  | nd | vd |  |
| --- | --- | --- | --- |
| lens L1 | 1.88 |  | HRI |
| lens L2 | 1.58 | 61 |  |
| lens L3 | 1.59 | 39 |  |
| prism | 1.88 | 40 | HRI |
| lens L4 | 1.71 | 47 | HRI-LD |
| lens L5 | 1.72 | 54 | LD |
| lens L6 | ≤1.9 | 18 | HRI-HD |
| cover glass CG | 1.88 |  | HRI |

In the example 32, a full angle of view is 100 degrees.

Example 33

An oblique-viewing objective optical system according to an example 33 will be described below. The oblique-viewing objective optical system of the example 33 includes in order from an object side, a front-side lens group GF having a negative refractive power, an optical path converting element P, an aperture stop S, and a rear-side lens group GR having a positive refractive power.

The front-side lens group GF includes a planoconcave negative lens L1 of which an object side is a plane surface, and a planoconvex positive lens L2 of which an object side is a plane surface.

The optical path converting element P is disposed between the front-side lens group GF and the rear-side lens group GR. The optical path converting element P is a prism.

The aperture stop S is disposed between the optical path converting element P and the rear-side lens group GR. More specifically, the aperture stop S is provided to an image-side surface of the optical path converting element P.

The rear-side lens group GR includes a biconvex positive lens L3, a biconvex positive lens L4, and a negative meniscus lens L5 having a convex surface directed toward an image side. Here, a cemented lens having a positive refractive power is formed by the biconvex positive lens L4 and the negative meniscus lens L5. A surface having a smaller radius of curvature of the biconvex positive lens L3 is directed toward the image-plane side.

A filter F1, a cover glass CG, and a glass lid GL are disposed in the rear-side lens group GR. The filter F1 is disposed between the biconvex positive lens L3 and the cemented lens.

|  | nd | vd |  |
| --- | --- | --- | --- |
| lens L1 | 1.88 |  | HRI |
| lens L2 | 1.74 | 27 | HRI |
| lens L3 | 1.51 | 64 | LRI-LD |
| prism | 1.61 | 54 | HRI-LD |
| lens L4 | 1.51 | 64 | LD |
| lens L5 | ≤1.9 | 18 | HRI-HD |
| cover glass CG | 1.51 |  | LRI |

In the example 33, a full angle of view is 100 degrees.

As described above, the oblique-viewing objective optical system of each example includes the front-side lens group which is disposed on the object side of the prism, and the rear-side lens group which is disposed on the image side of the prism, and the front-side lens group has a negative refractive power, and includes the lens having a negative refractive power, having a concave surface directed toward the image-plane side, and the single lens having a convex surface directed toward the image-plane side or the cemented lens, and the rear-side lens group has a positive refractive power, and includes the lens having a positive refractive power, and the cemented lens having a positive refractive power, and the cemented lens is formed by cementing in order of the lens having a positive refractive power and the lens having a negative refractive power, and the aperture stop is provided between the prism and the rear-side lens group.

The oblique-viewing objective optical system according to each example has the optimum lens arrangement with the optical performance improved in responding small-sizing and increasing number of pixels of the image pickup element, and such arrangement also contributes to thinning of diameter of the front-end portion of endoscope. Furthermore, since the oblique-viewing objective optical system of each example satisfies each conditional expression, various aberrations are corrected favorably.

Numerical data of each example described above is shown below. In Surface data, r denotes radius of curvature of each surface, d denotes a thickness of each optical member or air distance, nd denotes a refractive index of each optical member for d-line, and vd denotes an Abbe number for each optical member. In Various data, IH denotes an image height, ω denotes a half angle of view, Fno denotes an F-number, f denotes a focal length of the overall oblique-viewing objective optical system, D1 denotes an air-conversion length from an image-side surface of a lens positioned nearest to an image plane in the front-side lens group up to the aperture stop, D2 denotes an air-conversion length from an image-side surface of a rearmost lens in the rear-side lens group up to the image plane, L denotes an overall length of the oblique-viewing objective optical system, fF denotes a focal length of the front-side lens group, fR denotes a focal length of the rear-side lens group, and vd (L2) denotes an Abbe number of the second lens. Moreover, unit of r, d, IH, air-conversion length, and each overall length and focal length of the overall oblique-viewing objective optical system is mm.

Example 1

Unit mm
Surface data

| Surface no. | r | d | nd | vd |
|---|---|---|---|---|
| 1 | ∞ | 0.5062 | 1.88300 | 40.76 |
| 2 | 1.3194 | 0.7749 | | |
| 3 | −69.5360 | 1.0234 | 1.62588 | 35.70 |
| 4 | −4.4939 | 0.2531 | | |
| 5 | ∞ | 3.0374 | 1.88300 | 40.76 |
| 6 | ∞ | 0.0000 | | |
| 7(Stop) | ∞ | 0.3037 | | |
| 8 | 8.7102 | 0.8155 | 1.62230 | 53.17 |
| 9 | −2.8173 | 0.0943 | | |
| 10 | ∞ | 0.6750 | 1.49400 | 75.00 |
| 11 | ∞ | 0.1687 | | |
| 12 | 1.6635 | 1.3899 | 1.51633 | 64.14 |
| 13 | −1.7043 | 0.5062 | 1.92286 | 18.90 |
| 14 | −12.2064 | 0.6059 | | |
| 15 | ∞ | 0.5062 | 1.88300 | 40.76 |
| 16 | ∞ | 0.0169 | 1.51300 | 64.00 |
| 17 | ∞ | 0.5906 | 1.50510 | 63.26 |
| 18 (Image plane) | ∞ | 0.0000 | | |

Various data

| | |
|---|---|
| IH | 0.766 |
| ω | 49.93 |
| Fno | 2.935 |
| f | 1 |
| D1 | 1.866 |
| D2 | 1.278 |
| L | 11.268 |
| |fF| | 2.43 |
| fR | 2.149 |
| |f1| | 1.494 |
| vd(L2) | 35.7 |

Example 2

Unit mm
Surface data

| Surface no. | r | d | nd | vd |
|---|---|---|---|---|
| 1 | ∞ | 0.5192 | 1.88300 | 40.76 |
| 2 | 1.2301 | 1.2236 | | |
| 3 | −2.4328 | 0.6352 | 1.58144 | 40.75 |
| 4 | −2.0468 | 0.2596 | | |
| 5 | ∞ | 3.1153 | 1.76820 | 71.79 |
| 6 | ∞ | 0.0000 | | |
| 7(Stop) | ∞ | 0.3115 | | |
| 8 | 7.8933 | 0.8839 | 1.58913 | 61.14 |
| 9 | −3.3555 | 0.0967 | | |
| 10 | ∞ | 0.6923 | 1.49400 | 75.00 |
| 11 | ∞ | 0.1731 | | |
| 12 | 2.0108 | 2.0624 | 1.51633 | 64.14 |
| 13 | −1.4835 | 0.5192 | 1.92286 | 18.90 |
| 14 | −7.0564 | 0.7632 | | |
| 15 | ∞ | 0.5192 | 1.88300 | 40.76 |
| 16 | ∞ | 0.0173 | 1.51300 | 64.00 |
| 17 | ∞ | 0.6058 | 1.50510 | 63.26 |
| 18 (Image plane) | ∞ | 0.0000 | | |

Various data

| | |
|---|---|
| IH | 0.786 |
| ω | 49.901 |
| Fno | 2.913 |
| f | 1 |
| D1 | 2.021 |
| D2 | 1.453 |
| L | 12.398 |
| |fF| | 2 |
| fR | 2.476 |
| |f1| | 1.393 |
| vd(L2) | 40.75 |

Example 3

Unit mm
Surface data

| Surface no. | r | d | nd | vd |
|---|---|---|---|---|
| 1 | ∞ | 0.5183 | 1.88300 | 40.76 |
| 2 | 1.2902 | 1.0754 | | |
| 3 | −2.7566 | 0.7775 | 1.58144 | 40.75 |
| 4 | −2.3756 | 0.2592 | | |
| 5 | ∞ | 3.1100 | 1.51633 | 64.14 |
| 6 | ∞ | 0.0000 | | |
| 7(Stop) | ∞ | 0.3110 | | |
| 8 | 7.8819 | 0.8621 | 1.58913 | 61.14 |
| 9 | −3.4604 | 0.0966 | | |
| 10 | ∞ | 0.6911 | 1.49400 | 75.00 |
| 11 | ∞ | 0.1728 | | |
| 12 | 1.9654 | 2.0894 | 1.51633 | 64.14 |
| 13 | −1.4850 | 0.5183 | 1.92286 | 18.90 |
| 14 | −8.2062 | 0.7483 | | |
| 15 | ∞ | 0.5183 | 1.88300 | 40.76 |
| 16 | ∞ | 0.0173 | 1.51300 | 64.00 |
| 17 | ∞ | 0.6047 | 1.50510 | 63.26 |
| 18 (Image plane) | ∞ | 0.0000 | | |

Various data

| | |
|---|---|
| IH | 0.784 |
| ω | 49.912 |
| Fno | 2.959 |
| f | 1 |
| D1 | 2.31 |
| D2 | 1.437 |
| L | 12.37 |
| |fF| | 2.003 |
| fR | 2.473 |
| |f1| | 1.461 |
| vd(L2) | 40.75 |

Example 4

Unit mm
Surface data

| Surface no. | r | d | nd | vd |
|---|---|---|---|---|
| 1 | ∞ | 0.5139 | 1.88300 | 40.76 |
| 2 | 1.3854 | 0.8379 | | |
| 3 | −6.3453 | 1.1330 | 1.74077 | 27.79 |
| 4 | −3.8981 | 0.1713 | | |
| 5 | ∞ | 3.0835 | 1.51633 | 64.14 |
| 6 | ∞ | 0.0000 | | |
| 7(Stop) | ∞ | 0.3083 | | |
| 8 | 7.6238 | 0.8543 | 1.51633 | 64.14 |
| 9 | −2.9335 | 0.0958 | | |
| 10 | ∞ | 0.6852 | 1.49400 | 75.00 |
| 11 | ∞ | 0.1713 | | |
| 12 | 1.8426 | 1.8426 | 1.48749 | 70.23 |
| 13 | −1.5314 | 0.5139 | 1.92286 | 18.90 |
| 14 | −4.1089 | 0.7559 | | |
| 15 | ∞ | 0.5139 | 1.88300 | 40.76 |
| 16 | ∞ | 0.0171 | 1.51300 | 64.00 |
| 17 | ∞ | 0.5996 | 1.50510 | 63.26 |
| 18 | ∞ | 0.0000 | | |
| (Image plane) | | | | |

Various data

| | |
|---|---|
| IH | 0.778 |
| ω | 49.914 |
| Fno | 2.969 |
| f | 1 |
| D1 | 2.205 |
| D2 | 1.439 |
| L | 12.098 |
| \|fF\| | 2.359 |
| fR | 2.469 |
| \|f1\| | 1.569 |
| vd(L2) | 27.79 |

Example 5

Unit mm
Surface data

| Surface no. | r | d | nd | vd |
|---|---|---|---|---|
| 1 | ∞ | 0.5716 | 1.88300 | 40.76 |
| 2 | 1.4865 | 1.3095 | | |
| 3 | −5.4021 | 0.7246 | 1.74077 | 27.79 |
| 4 | −3.8365 | 0.2858 | | |
| 5 | ∞ | 3.4293 | 1.51633 | 64.14 |
| 6 | ∞ | 0.0000 | | |
| 7(Stop) | ∞ | 0.3429 | | |
| 8 | 8.0445 | 1.0374 | 1.58913 | 61.14 |
| 9 | −3.6908 | 0.1065 | | |
| 10 | ∞ | 0.7621 | 1.49400 | 75.00 |
| 11 | ∞ | 0.1905 | | |
| 12 | 2.0697 | 1.8351 | 1.51633 | 64.14 |
| 13 | −1.7932 | 0.5716 | 1.92286 | 18.90 |
| 14 | −6.0848 | 0.7025 | | |
| 15 | ∞ | 0.6287 | 1.51633 | 64.14 |
| 16 | ∞ | 0.0191 | 1.51300 | 64.00 |
| 17 | ∞ | 0.6668 | 1.50510 | 63.26 |
| 18 | ∞ | 0.0000 | | |
| (Image plane) | | | | |

Various data

| | |
|---|---|
| IH | 0.77 |
| ω | 49.885 |
| Fno | 2.954 |
| f | 1 |
| D1 | 2.547 |
| D2 | 1.573 |
| L | 13.184 |
| \|fF\| | 2.341 |
| fR | 2.622 |
| \|f1\| | 1.683 |
| vd(L2) | 27.79 |

Example 6

Unit mm
Surface data

| Surface no. | r | d | nd | vd |
|---|---|---|---|---|
| 1 | ∞ | 0.5570 | 1.88300 | 40.76 |
| 2 | 1.4967 | 1.3302 | | |
| 3 | 27.8259 | 0.6536 | 1.74077 | 27.79 |
| 4 | −9.9577 | 0.2785 | | |
| 5 | ∞ | 3.3419 | 1.51633 | 64.14 |
| 6 | ∞ | 0.0000 | | |
| 7(Stop) | ∞ | 0.3342 | | |
| 8 | 17.6150 | 0.8477 | 1.61405 | 54.99 |
| 9 | −3.1277 | 0.1038 | | |
| 10 | ∞ | 0.7427 | 1.49400 | 75.00 |
| 11 | ∞ | 0.1857 | | |
| 12 | 1.7287 | 1.6032 | 1.51633 | 64.14 |
| 13 | −1.7376 | 0.5570 | 1.92286 | 18.90 |
| 14 | −8.7562 | 0.6416 | | |
| 15 | ∞ | 0.5570 | 1.51633 | 64.14 |
| 16 | ∞ | 0.0186 | 1.51300 | 64.00 |
| 17 | ∞ | 0.6498 | 1.50510 | 63.26 |
| 18 | ∞ | 0.0000 | | |
| (Image plane) | | | | |

Various data

| | |
|---|---|
| IH | 0.75 |
| ω | 49.917 |
| Fno | 2.805 |
| f | 1 |
| D1 | 2.482 |
| D2 | 1.453 |
| L | 12.402 |
| \|fF\| | 2.535 |
| fR | 2.406 |
| \|f1\| | 1.695 |
| vd(L2) | 27.79 |

Example 7

Unit mm
Surface data

| Surface no. | r | d | nd | vd |
|---|---|---|---|---|
| 1 | ∞ | 0.5612 | 1.88300 | 40.76 |
| 2 | 1.4828 | 0.7761 | | |
| 3 | −81.7714 | 1.2159 | 1.74077 | 27.79 |
| 4 | −7.2782 | 0.2806 | | |
| 5 | ∞ | 3.3672 | 1.51633 | 64.14 |
| 6 | ∞ | 0.0000 | | |
| 7(Stop) | ∞ | 0.3367 | | |
| 8 | 10.1814 | 0.8947 | 1.61405 | 54.99 |
| 9 | −3.2206 | 0.1046 | | |
| 10 | ∞ | 0.7483 | 1.49400 | 75.00 |
| 11 | ∞ | 0.1871 | | |

-continued

Unit mm
Surface data

| | | | | |
|---|---|---|---|---|
| 12 | 1.7951 | 1.5299 | 1.51633 | 64.14 |
| 13 | −1.8511 | 0.5612 | 1.92286 | 18.90 |
| 14 | −8.4511 | 0.6480 | | |
| 15 | ∞ | 0.5612 | 1.51633 | 64.14 |
| 16 | ∞ | 0.0187 | 1.51300 | 64.00 |
| 17 | ∞ | 0.6547 | 1.50510 | 63.26 |
| 18 | ∞ | 0.0000 | | |
| (Image plane) | | | | |

Various data

| | |
|---|---|
| IH | 0.756 |
| ω | 49.91 |
| Fno | 2.748 |
| f | 1 |
| D1 | 2.501 |
| D2 | 1.466 |
| L | 12.446 |
| \|fF\| | 2.4 |
| fR | 2.376 |
| \|f1\| | 1.679 |
| νd(L2) | 27.79 |

Example 8

Unit mm
Surface data

| Surface no. | r | d | nd | νd |
|---|---|---|---|---|
| 1 | ∞ | 0.5648 | 1.88300 | 40.76 |
| 2 | 1.4260 | 0.7849 | | |
| 3 | −50.1550 | 1.2236 | 1.74077 | 27.79 |
| 4 | −6.3567 | 0.2824 | | |
| 5 | ∞ | 3.3885 | 1.80610 | 40.92 |
| 6 | ∞ | 0.0000 | | |
| 7(Stop) | ∞ | 0.3389 | | |
| 8 | 9.9395 | 0.8913 | 1.61405 | 54.99 |
| 9 | −3.0645 | 0.1052 | | |
| 10 | ∞ | 0.7530 | 1.49400 | 75.00 |
| 11 | ∞ | 0.1883 | | |
| 12 | 1.8206 | 1.4188 | 1.51633 | 64.14 |
| 13 | −1.9127 | 0.5648 | 1.92286 | 18.90 |
| 14 | −7.5390 | 0.6575 | | |
| 15 | ∞ | 0.5648 | 1.51633 | 64.14 |
| 16 | ∞ | 0.0188 | 1.51300 | 64.00 |
| 17 | ∞ | 0.6589 | 1.50510 | 63.26 |
| 18 | ∞ | 0.0000 | | |
| (Image plane) | | | | |

Various data

| | |
|---|---|
| IH | 0.761 |
| ω | 49.928 |
| Fno | 2.785 |
| f | 1 |
| D1 | 2.159 |
| D2 | 1.48 |
| L | 12.404 |
| \|fF\| | 2.407 |
| fR | 2.336 |
| \|f1\| | 1.615 |
| νd(L2) | 27.79 |

Example 9

Unit mm
Surface data

| Surface no. | r | d | nd | νd |
|---|---|---|---|---|
| 1 | ∞ | 0.5652 | 1.88300 | 40.76 |
| 2 | 1.4209 | 0.7867 | | |
| 3 | −43.7553 | 1.2247 | 1.74077 | 27.79 |
| 4 | −5.8565 | 0.2826 | | |
| 5 | ∞ | 3.3913 | 1.88300 | 40.76 |
| 6 | ∞ | 0.0000 | | |
| 7(Stop) | ∞ | 0.3391 | | |
| 8 | 9.2500 | 0.8969 | 1.61405 | 54.99 |
| 9 | −3.0400 | 0.1053 | | |
| 10 | ∞ | 0.7536 | 1.49400 | 75.00 |
| 11 | ∞ | 0.1884 | | |
| 12 | 1.7914 | 1.3681 | 1.51633 | 64.14 |
| 13 | −1.9111 | 0.5652 | 1.92286 | 18.90 |
| 14 | −7.8580 | 0.6773 | | |
| 15 | ∞ | 0.5652 | 1.88300 | 40.76 |
| 16 | ∞ | 0.0188 | 1.51300 | 64.00 |
| 17 | ∞ | 0.6594 | 1.50510 | 63.26 |
| 18 | ∞ | 0.0000 | | |
| (Image plane) | | | | |

Various data

| | |
|---|---|
| IH | 0.761 |
| ω | 49.932 |
| Fno | 2.884 |
| f | 1 |
| D1 | 2.084 |
| D2 | 1.428 |
| L | 12.388 |
| \|fF\| | 2.495 |
| fR | 2.307 |
| \|f1\| | 1.609 |
| νd(L2) | 27.79 |

Example 10

Unit mm
Surface data

| Surface no. | r | d | nd | νd |
|---|---|---|---|---|
| 1 | ∞ | 0.6524 | 1.88300 | 40.76 |
| 2 | 1.6794 | 1.5882 | | |
| 3 | −4.3655 | 0.8310 | 1.70154 | 41.24 |
| 4 | −3.7554 | 0.2175 | | |
| 5 | ∞ | 3.9145 | 1.51633 | 64.14 |
| 6 | ∞ | 0.0000 | | |
| 7(Stop) | ∞ | 0.3915 | | |
| 8 | 9.6178 | 0.9462 | 1.62230 | 53.17 |
| 9 | −4.9574 | 0.1087 | | |
| 10 | ∞ | 0.8699 | 1.49400 | 75.00 |
| 11 | ∞ | 0.2175 | | |
| 12 | 3.2222 | 2.5044 | 1.75500 | 52.32 |
| 13 | −1.7773 | 0.6524 | 1.92286 | 18.90 |
| 14 | −13.5540 | 0.6209 | | |
| 15 | ∞ | 0.6524 | 1.51633 | 64.14 |
| 16 | ∞ | 0.0217 | 1.51300 | 64.00 |
| 17 | ∞ | 0.7612 | 1.50510 | 63.26 |
| 18 | ∞ | 0.0000 | | |
| (Image plane) | | | | |

Various data

| | |
|---|---|
| IH | 0.879 |
| ω | 59.849 |
| Fno | 2.847 |
| f | 1 |

-continued

| Unit mm Surface data | |
|---|---|
| D1 | 2.799 |
| D2 | 1.571 |
| L | 14.95 |
| \|fF\| | 2.481 |
| fR | 2.805 |
| \|f1\| | 1.902 |
| vd(L2) | 41.24 |

Example 11

| Unit mm Surface data | | | | |
|---|---|---|---|---|
| Surface no. | r | d | nd | vd |
| 1 | ∞ | 0.7039 | 1.88300 | 40.76 |
| 2 | 1.7723 | 1.8532 | | |
| 3 | −4.1698 | 0.7591 | 1.70154 | 41.24 |
| 4 | −3.6874 | 0.2346 | | |
| 5 | ∞ | 4.2234 | 1.51633 | 64.14 |
| 6 | ∞ | 0.0000 | | |
| 7(Stop) | ∞ | 0.4223 | | |
| 8 | 10.7127 | 1.1361 | 1.62230 | 53.17 |
| 9 | −5.2256 | 0.1173 | | |
| 10 | ∞ | 0.9385 | 1.49400 | 75.00 |
| 11 | ∞ | 0.2346 | | |
| 12 | 3.1601 | 2.6022 | 1.75500 | 52.32 |
| 13 | −1.8834 | 0.7039 | 1.92286 | 18.90 |
| 14 | −21.7315 | 0.5068 | | |
| 15 | ∞ | 0.7039 | 1.51633 | 64.14 |
| 16 | ∞ | 0.0235 | 1.51300 | 64.00 |
| 17 | ∞ | 0.8212 | 1.50510 | 63.26 |
| 18 (Image plane) | ∞ | 0.0000 | | |

| Various data | |
|---|---|
| IH | 0.948 |
| ω | 69.755 |
| Fno | 2.977 |
| f | 1 |
| D1 | 3.02 |
| D2 | 1.532 |
| L | 15.985 |
| \|fF\| | 2.59 |
| fR | 2.907 |
| \|f1\| | 2.007 |
| vd(L2) | 41.24 |

Example 12

| Unit mm Surface data | | | | |
|---|---|---|---|---|
| Surface no. | r | d | nd | vd |
| 1 | ∞ | 0.7058 | 1.88300 | 40.76 |
| 2 | 1.7114 | 1.8865 | | |
| 3 | −4.3112 | 0.7460 | 1.70154 | 41.24 |
| 4 | −3.7270 | 0.2353 | | |
| 5 | ∞ | 4.2349 | 1.80610 | 40.92 |
| 6 | ∞ | 0.0000 | | |
| 7 (Stop) | ∞ | 0.4235 | | |
| 8 | 10.3467 | 1.1767 | 1.62230 | 53.17 |
| 9 | −4.8423 | 0.1176 | | |
| 10 | ∞ | 0.9411 | 1.49400 | 75.00 |
| 11 | ∞ | 0.2353 | | |

-continued

| Unit mm Surface data | | | | |
|---|---|---|---|---|
| 12 | 3.1648 | 2.5823 | 1.75500 | 52.32 |
| 13 | −1.8865 | 0.7058 | 1.92286 | 18.90 |
| 14 | −20.6467 | 0.5212 | | |
| 15 | ∞ | 0.7058 | 1.88300 | 40.76 |
| 16 | ∞ | 0.0235 | 1.51300 | 64.00 |
| 17 | ∞ | 0.8235 | 1.50510 | 63.26 |
| 18 (Image plane) | ∞ | 0.0000 | | |

| Various data | |
|---|---|
| IH | 0.951 |
| ω | 69.779 |
| Fno | 2.891 |
| f | 1 |
| D1 | 2.58 |
| D2 | 1.459 |
| L | 16.065 |
| \|fF\| | 2.522 |
| fR | 2.839 |
| \|f1\| | 1.938 |
| vd (L2) | 41.24 |

Example 13

| Unit mm Surface data | | | | |
|---|---|---|---|---|
| Surface no. | r | d | nd | vd |
| 1 | ∞ | 0.9676 | 1.76820 | 71.79 |
| 2 | 1.5597 | 2.1057 | | |
| 3 | −3.1361 | 0.8064 | 1.58913 | 61.14 |
| 4 | −5.1221 | 1.1289 | 1.53172 | 48.84 |
| 5 | −2.7614 | 0.0599 | | |
| 6 | ∞ | 5.8059 | 1.80610 | 40.92 |
| 7 | ∞ | 0.0000 | | |
| 8 (Stop) | ∞ | 0.5806 | | |
| 9 | 70.8526 | 1.4477 | 1.58913 | 61.14 |
| 10 | −5.1448 | 0.2580 | | |
| 11 | ∞ | 1.2902 | 1.49400 | 75.00 |
| 12 | ∞ | 0.0968 | | |
| 13 | 4.0515 | 2.5531 | 1.72916 | 54.68 |
| 14 | −2.7894 | 0.9676 | 1.92286 | 18.90 |
| 15 | −9.9702 | 0.8135 | | |
| 16 | ∞ | 0.9676 | 1.88300 | 40.76 |
| 17 | ∞ | 0.0323 | 1.51300 | 64.00 |
| 18 | ∞ | 1.1289 | 1.50510 | 63.26 |
| 19 (Image plane) | ∞ | 0.0000 | | |

| Various data | |
|---|---|
| IH | 0.764 |
| ω | 49.988 |
| Fno | 2.91 |
| f | 1 |
| D1 | 3.275 |
| D2 | 2.099 |
| L | 21.011 |
| \|fF\| | 4.01 |
| fR | 3.668 |
| \|f1\| | 2.03 |

Example 14

Unit mm
Surface data

| Surface no. | r | d | nd | νd |
|---|---|---|---|---|
| 1 | ∞ | 0.9733 | 1.76820 | 71.79 |
| 2 | 1.4955 | 1.7058 | | |
| 3 | −2.9530 | 0.8111 | 1.58913 | 61.14 |
| 4 | −9.2593 | 1.4600 | 1.53172 | 48.84 |
| 5 | −2.7583 | 0.0768 | | |
| 6 | ∞ | 5.8399 | 1.80610 | 40.92 |
| 7 | ∞ | 0.0000 | | |
| 8 (Stop) | ∞ | 0.5840 | | |
| 9 | 188.4216 | 1.7096 | 1.72916 | 54.68 |
| 10 | −6.3042 | 0.2596 | | |
| 11 | ∞ | 1.2978 | 1.49400 | 75.00 |
| 12 | ∞ | 0.0973 | | |
| 13 | 4.0875 | 2.6251 | 1.72916 | 54.68 |
| 14 | −2.7601 | 1.0382 | 1.92286 | 18.90 |
| 15 | −10.8193 | 0.8820 | | |
| 16 | ∞ | 0.9733 | 1.88300 | 40.76 |
| 17 | ∞ | 0.0324 | 1.51300 | 64.00 |
| 18 | ∞ | 1.1355 | 1.50510 | 63.26 |
| 19 (Image plane) | ∞ | 0.0000 | | |

Various data

| | |
|---|---|
| IH | 0.796 |
| ω | 50 |
| Fno | 2.978 |
| f | 1 |
| D1 | 3.31 |
| D2 | 2.175 |
| L | 21.502 |
| \|fF\| | 3.788 |
| fR | 3.754 |
| \|f1\| | 1.947 |

Example 15

Unit mm
Surface data

| Surface no. | r | d | nd | νd |
|---|---|---|---|---|
| 1 | ∞ | 0.9810 | 1.88300 | 40.76 |
| 2 | 1.5515 | 1.6149 | | |
| 3 | −3.2685 | 0.8175 | 1.58913 | 61.14 |
| 4 | −11.3393 | 1.4716 | 1.53172 | 48.84 |
| 5 | −2.7957 | 0.0942 | | |
| 6 | ∞ | 5.8863 | 1.80610 | 40.92 |
| 7 | ∞ | 0.0000 | | |
| 8 (Stop) | ∞ | 0.5886 | | |
| 9 | 142.1161 | 1.7757 | 1.74320 | 49.34 |
| 10 | −6.5604 | 0.2616 | | |
| 11 | ∞ | 1.3081 | 1.49400 | 75.00 |
| 12 | ∞ | 0.0981 | | |
| 13 | 4.2497 | 2.7058 | 1.72916 | 54.68 |
| 14 | −2.7222 | 1.0465 | 1.92286 | 18.90 |
| 15 | −11.1714 | 1.0170 | | |
| 16 | ∞ | 0.9810 | 1.88300 | 40.76 |
| 17 | ∞ | 0.0327 | 1.51300 | 64.00 |
| 18 | ∞ | 1.1446 | 1.50510 | 63.26 |
| 19 (Image plane) | ∞ | 0.0000 | | |

Various data

| | |
|---|---|
| IH | 0.775 |
| ω | 50 |
| Fno | 2.943 |
| f | 1 |
| D1 | 3.353 |
| D2 | 2.32 |
| L | 21.825 |
| \|fF\| | 3.528 |
| fR | 3.874 |
| \|f1\| | 1.757 |

Example 16

Unit mm
Surface data

| Surface no. | r | d | nd | νd |
|---|---|---|---|---|
| 1 | ∞ | 0.9763 | 1.88300 | 40.76 |
| 2 | 1.8323 | 1.7507 | | |
| 3 | −3.5431 | 0.8136 | 1.58913 | 61.14 |
| 4 | 36.3604 | 1.3440 | 1.58144 | 40.75 |
| 5 | −3.7537 | 0.0911 | | |
| 6 | ∞ | 5.8579 | | |
| 7 | ∞ | 0.0000 | | |
| 8 (Stop) | ∞ | 0.5858 | | |
| 9 | 255.3489 | 2.2080 | 1.71700 | 47.92 |
| 10 | −6.0825 | 0.2604 | | |
| 11 | ∞ | 1.3018 | 1.49400 | 75.00 |
| 12 | ∞ | 0.0976 | | |
| 13 | 4.0474 | 2.8067 | 1.72916 | 54.68 |
| 14 | −2.6506 | 0.9763 | 1.92286 | 18.90 |
| 15 | −10.7949 | 1.0357 | | |
| 16 | ∞ | 0.9763 | 1.88300 | 40.76 |
| 17 | ∞ | 0.0325 | 1.51300 | 64.00 |
| 18 | ∞ | 1.1390 | 1.50510 | 63.26 |
| 19 (Image plane) | ∞ | 0.0000 | | |

Various data

| | |
|---|---|
| IH | 0.771 |
| ω | 49.999 |
| Fno | 2.81 |
| f | 1 |
| D1 | 3.202 |
| D2 | 2.333 |
| L | 22.254 |
| \|fF\| | 2.968 |
| fR | 3.737 |
| \|f1\| | 2.075 |

Example 17

Unit mm
Surface data

| Surface no. | r | d | nd | νd |
|---|---|---|---|---|
| 1 | ∞ | 1.9763 | 1.88300 | 40.76 |
| 2 | 1.6796 | 2.3721 | | |
| 3 | −3.0453 | 0.9102 | 1.58913 | 61.14 |
| 4 | −12.8380 | 1.3271 | 1.54814 | 45.79 |
| 5 | −3.0049 | 0.0236 | | |
| 6 | ∞ | 6.5535 | 1.80610 | 40.92 |
| 7 | ∞ | 0.0000 | | |
| 8 (Stop) | ∞ | 0.6553 | | |
| 9 | 35.1593 | 1.9478 | 1.58913 | 61.14 |
| 10 | −7.7012 | 0.2913 | | |
| 11 | ∞ | 1.4563 | 1.49400 | 75.00 |
| 12 | ∞ | 0.1092 | | |
| 13 | 4.4231 | 3.7637 | 1.75500 | 52.32 |
| 14 | −2.6317 | 1.0922 | 1.92286 | 18.90 |
| 15 | −13.0401 | 0.7946 | | |
| 16 | ∞ | 1.0922 | 1.88300 | 40.76 |
| 17 | ∞ | 0.0364 | 1.51300 | 64.00 |

-continued

| | | | | |
|---|---|---|---|---|
| 18 | ∞ | 1.2743 | 1.50510 | 63.26 |
| 19 | ∞ | 0.0000 | | |
| (Image plane) | | | | |

Various data

| | |
|---|---|
| IH | 0.863 |
| ω | 60 |
| Fno | 2.936 |
| f | 1 |
| D1 | 3.652 |
| D2 | 2.245 |
| L | 24.792 |
| |fF| | 3.419 |
| fR | 4.327 |
| |f1| | 1.902 |

Example 18

Unit mm
Surface data

| Surface no. | r | d | nd | vd |
|---|---|---|---|---|
| 1 | ∞ | 1.1926 | 1.88300 | 40.76 |
| 2 | 1.8627 | 2.4500 | | |
| 3 | −3.0179 | 0.9938 | 1.58913 | 61.14 |
| 4 | −27.9725 | 1.2403 | 1.54814 | 45.79 |
| 5 | −3.1399 | 0.1988 | | |
| 6 | ∞ | 7.1554 | 1.80610 | 40.92 |
| 7 | ∞ | 0.0000 | | |
| 8 (Stop) | ∞ | 0.7155 | | |
| 9 | 21.1481 | 2.4670 | 1.58913 | 61.14 |
| 10 | −8.1016 | 0.3180 | | |
| 11 | ∞ | 1.5901 | 1.49400 | 75.00 |
| 12 | ∞ | 0.1193 | | |
| 13 | 4.9099 | 3.5777 | 1.75500 | 52.32 |
| 14 | −2.6387 | 1.1131 | 1.92286 | 18.90 |
| 15 | −9.5801 | 0.8340 | | |
| 16 | ∞ | 1.1926 | 1.88300 | 40.76 |
| 17 | ∞ | 0.0398 | 1.51300 | 64.00 |
| 18 | ∞ | 1.3913 | 1.50510 | 63.26 |
| 19 | ∞ | 0.0000 | | |
| (Image plane) | | | | |

Various data

| | |
|---|---|
| IH | 0.942 |
| ω | 70.033 |
| Fno | 2.797 |
| f | 1 |
| D1 | 4.161 |
| D2 | 2.418 |
| L | 26.589 |
| |fF| | 3.424 |
| fR | 4.491 |
| |f1| | 2.11 |

Example 19

Unit mm
Surface data

| Surface no. | r | d | nd | vd |
|---|---|---|---|---|
| 1 | ∞ | 1.2193 | 1.88300 | 40.76 |
| 2 | 1.8883 | 2.5516 | | |
| 3 | −2.8986 | 1.0161 | 1.58913 | 61.14 |
| 4 | 68.5175 | 1.2912 | 1.54814 | 45.79 |
| 5 | −3.2174 | 0.2032 | | |
| 6 | ∞ | 7.3158 | 1.88300 | 40.76 |
| 7 | ∞ | 0.0000 | | |
| 8 (Stop) | ∞ | 0.7316 | | |
| 9 | 24.1646 | 2.6992 | 1.58913 | 61.14 |
| 10 | −8.6042 | 0.3251 | | |
| 11 | ∞ | 1.6257 | 1.49400 | 75.00 |
| 12 | ∞ | 0.1219 | | |
| 13 | 5.3247 | 3.8611 | 1.75500 | 52.32 |
| 14 | −2.7178 | 1.2193 | 1.92286 | 18.90 |
| 15 | −8.4132 | 1.0584 | | |
| 16 | ∞ | 1.2193 | 1.88300 | 40.76 |
| 17 | ∞ | 0.0406 | 1.51300 | 64.00 |
| 18 | ∞ | 1.4225 | 1.50510 | 63.26 |
| 19 | ∞ | 0.0000 | | |
| (Image plane) | | | | |

Various data

| | |
|---|---|
| IH | 0.963 |
| ω | 75 |
| Fno | 2.972 |
| f | 1 |
| D1 | 4.088 |
| D2 | 2.678 |
| L | 27.922 |
| |fF| | 3.206 |
| fR | 4.737 |
| |f1| | 2.139 |

Example 20

Unit mm
Surface data

| Surface no. | r | d | nd | vd |
|---|---|---|---|---|
| 1 | ∞ | 0.5057 | 1.51633 | 64.14 |
| 2 | 1.1020 | 0.8409 | | |
| 3 | −2.8069 | 0.9920 | 1.48749 | 70.23 |
| 4 | −3.4857 | 0.2529 | | |
| 5 | ∞ | 3.0343 | 1.88300 | 40.76 |
| 6 | ∞ | 0.0000 | | |
| 7 (Stop) | ∞ | 0.3034 | | |
| 8 | 8.0661 | 0.8963 | 1.53996 | 59.46 |
| 9 | −2.7079 | 0.0942 | | |
| 10 | ∞ | 0.6743 | 1.49400 | 75.00 |
| 11 | ∞ | 0.1686 | | |
| 12 | 1.9196 | 1.7549 | 1.51633 | 64.14 |
| 13 | −1.5319 | 0.5057 | 1.92286 | 18.90 |
| 14 | −3.8070 | 0.6942 | | |
| 15 | ∞ | 0.5057 | 1.88300 | 40.76 |
| 16 | ∞ | 0.0169 | 1.51300 | 64.00 |
| 17 | ∞ | 0.5900 | 1.50510 | 63.26 |
| 18 | ∞ | 0.0000 | | |
| (Image plane) | | | | |

Various data

| | |
|---|---|
| IH | 0.765 |
| ω | 49.95 |
| Fno | 2.91 |
| f | 1 |
| D1 | 1.864 |
| D2 | 1.366 |
| L | 11.83 |
| |fF| | 2.225 |
| fR | 2.293 |
| |f1| | 2.134 |
| vd (L2) | 70.23 |

Example 21

Unit mm
Surface data

| Surface no. | r | d | nd | vd |
|---|---|---|---|---|
| 1 | ∞ | 0.4976 | 1.15633 | 64.14 |
| 2 | 1.1610 | 1.2278 | | |
| 3 | −1.7619 | 0.6556 | 1.48749 | 70.23 |
| 4 | −2.0605 | 0.1659 | | |
| 5 | ∞ | 2.9858 | 1.51633 | 64.14 |
| 6 | ∞ | 0.0000 | | |
| 7 (Stop) | ∞ | 0.2686 | | |
| 8 | 6.4367 | 0.8348 | 1.51633 | 64.14 |
| 9 | −3.0351 | 0.0927 | | |
| 10 | ∞ | 0.6635 | 1.49400 | 75.00 |
| 11 | ∞ | 0.1659 | | |
| 12 | 1.8818 | 1.8151 | 1.51633 | 64.14 |
| 13 | −1.4895 | 0.4976 | 1.92286 | 18.90 |
| 14 | −4.0348 | 0.6762 | | |
| 15 | ∞ | 0.4976 | 1.88300 | 40.76 |
| 16 | ∞ | 0.0166 | 1.15300 | 64.00 |
| 17 | ∞ | 0.5806 | 1.50510 | 63.26 |
| 18 | ∞ | 0.0000 | | |
| (Image plane) | | | | |

Various data

| | |
|---|---|
| IH | 0.753 |
| ω | 49.946 |
| Fno | 2.973 |
| f | 1 |
| D1 | 2.135 |
| D2 | 1.337 |
| L | 11.672 |
| \|fF\| | 2.405 |
| fR | 2.356 |
| \|f1\| | 2.249 |
| vd (L2) | 70.23 |

Example 22

Unit mm
Surface data

| Surface no. | r | d | nd | vd |
|---|---|---|---|---|
| 1 | ∞ | 0.5602 | 1.51633 | 64.14 |
| 2 | 1.1547 | 1.0724 | | |
| 3 | −1.9181 | 0.9124 | 1.51633 | 64.14 |
| 4 | −2.2743 | 0.2801 | | |
| 5 | ∞ | 3.3614 | 1.51633 | 64.14 |
| 6 | ∞ | 0.0000 | | |
| 7(Stop) | ∞ | 0.3361 | | |
| 8 | 7.1862 | 0.9594 | 1.58913 | 61.14 |
| 9 | −3.5738 | 0.1044 | | |
| 10 | ∞ | 0.7470 | 1.49400 | 75.00 |
| 11 | ∞ | 0.1867 | | |
| 12 | 1.8467 | 1.4511 | 1.51633 | 64.14 |
| 13 | −1.8306 | 0.5602 | 1.92286 | 18.90 |
| 14 | −7.1502 | 0.6907 | | |
| 15 | ∞ | 0.6163 | 1.51633 | 64.14 |
| 16 | ∞ | 0.0187 | 1.51300 | 64.00 |
| 17 | ∞ | 0.6536 | 1.50510 | 63.26 |
| 18 | ∞ | 0.0000 | | |
| (Image plane) | | | | |

Various data

| | |
|---|---|
| IH | 0.754 |
| ω | 50.424 |
| Fno | 3.226 |
| f | 1 |
| D1 | 2.497 |
| D2 | 1.544 |
| L | 12.511 |
| \|fF\| | 2.538 |
| fR | 2.458 |
| \|f1\| | 2.236 |
| vd (L2) | 64.14 |

Example 23

Unit mm
Surface data

| Surface no. | r | d | nd | vd |
|---|---|---|---|---|
| 1 | ∞ | 0.5584 | 1.51633 | 64.14 |
| 2 | 1.2161 | 1.1444 | | |
| 3 | −2.2766 | 0.8457 | 1.51633 | 64.14 |
| 4 | −2.6096 | 0.2792 | | |
| 5 | ∞ | 3.3502 | 1.51633 | 64.14 |
| 6 | ∞ | 0.0000 | | |
| 7(Stop) | ∞ | 0.3350 | | |
| 8 | 7.4115 | 0.9358 | 1.62299 | 58.16 |
| 9 | −3.6548 | 0.1040 | | |
| 10 | ∞ | 0.7445 | 1.49400 | 75.00 |
| 11 | ∞ | 0.1861 | | |
| 12 | 1.9692 | 1.4314 | 1.51633 | 64.14 |
| 13 | −1.8620 | 0.5584 | 1.92286 | 18.90 |
| 14 | −5.3473 | 0.6787 | | |
| 15 | ∞ | 0.6142 | 1.51633 | 64.14 |
| 16 | ∞ | 0.0186 | 1.51300 | 64.00 |
| 17 | ∞ | 0.6514 | 1.50510 | 63.26 |
| 18 | ∞ | 0.0000 | | |
| (Image plane) | | | | |

Various data

| | |
|---|---|
| IH | 0.752 |
| ω | 49.927 |
| Fno | 2.89 |
| f | 1 |
| D1 | 2.489 |
| D2 | 1.529 |
| L | 12.436 |
| \|fF\| | 2.607 |
| fR | 2.434 |
| \|f1\| | 2.355 |
| vd (L2) | 64.14 |

Example 24

Unit mm
Surface data

| Surface no. | r | d | nd | vd |
|---|---|---|---|---|
| 1 | ∞ | 0.9985 | 1.51633 | 64.14 |
| 2 | 2.0780 | 2.1397 | | |
| 3 | −2.1807 | 1.6323 | 1.48749 | 70.23 |
| 4 | −21.4579 | 0.3328 | | |
| 5 | ∞ | 5.9913 | 1.51633 | 64.14 |
| 6 | ∞ | 0.0000 | | |
| 7(Stop) | ∞ | 0.5991 | | |
| 8 | 14.6278 | 2.4643 | 1.56384 | 60.67 |
| 9 | −5.6190 | 0.1664 | | |
| 10 | ∞ | 1.3314 | 1.49400 | 75.00 |
| 11 | ∞ | 0.3328 | | |
| 12 | 3.0359 | 2.6436 | 1.51633 | 64.14 |
| 13 | −2.7137 | 0.9985 | 1.92286 | 18.90 |
| 14 | −6.3416 | 1.6851 | | |
| 15 | ∞ | 0.9985 | 1.88300 | 40.76 |
| 16 | ∞ | 0.0333 | 1.51300 | 64.00 |

-continued

| | | | | |
|---|---|---|---|---|
| 17 | ∞ | 1.1650 | 1.50510 | 63.26 |
| 18 | ∞ | 0.0000 | | |
| (Image plane) | | | | |

| Various data | |
|---|---|
| IH | 0.789 |
| ω | 59.815 |
| Fno | 2.952 |
| f | 1 |
| D1 | 4.284 |
| D2 | 3.011 |
| L | 23.513 |
| \|fF\| | 1.847 |
| fR | 4.107 |
| \|f1\| | 4.025 |
| vd (L2) | 70.23 |

Example 25

Unit mm
Surface data

| Surface no. | r | d | nd | vd |
|---|---|---|---|---|
| 1 | ∞ | 0.6620 | 1.51825 | 64.14 |
| 2 | 1.4171 | 1.6872 | | |
| 3 | -2.3903 | 0.8845 | 1.51825 | 64.14 |
| 4 | -3.5608 | 0.1103 | | |
| 5 | ∞ | 3.9719 | 1.51825 | 64.14 |
| 6 | ∞ | 0.0000 | | |
| 7(Stop) | ∞ | 0.3972 | | |
| 8 | 10.9867 | 1.0974 | 1.62555 | 58.16 |
| 9 | -4.2262 | 0.1233 | | |
| 10 | ∞ | 0.8826 | 1.49557 | 75.00 |
| 11 | ∞ | 0.2207 | | |
| 12 | 2.3035 | 1.8323 | 1.54212 | 59.46 |
| 13 | -1.9842 | 0.6620 | 1.93429 | 18.90 |
| 14 | -4.7958 | 0.7844 | | |
| 15 | ∞ | 0.7282 | 1.51825 | 64.14 |
| 16 | ∞ | 0.0221 | 1.51500 | 64.00 |
| 17 | ∞ | 0.7723 | 1.50700 | 63.26 |
| 18 | ∞ | 0.0000 | | |
| (Image plane) | | | | |

| Various data | |
|---|---|
| IH | 0.891 |
| ω | 70 |
| Fno | 2.91 |
| f | 1 |
| D1 | 2.726 |
| D2 | 1.791 |
| L | 14.838 |
| \|fF\| | 2.38 |
| fR | 2.781 |
| \|f1\| | 2.734 |
| vd (L2) | 64.14 |

Example 26

Unit mm
Surface data

| Surface no. | r | d | nd | vd |
|---|---|---|---|---|
| 1 | ∞ | 0.9231 | 1.51633 | 64.14 |
| 2 | 1.6681 | 1.8315 | | |
| 3 | -2.2544 | 0.9231 | 1.58913 | 61.14 |
| 4 | -10.7875 | 0.9231 | 1.53172 | 48.84 |
| 5 | -3.7817 | 0.1099 | | |
| 6 | ∞ | 5.5388 | 1.51633 | 64.14 |
| 7 | ∞ | 0.0000 | | |
| 8(Stop) | ∞ | 0.5539 | | |
| 9 | 25.5699 | 1.9391 | 1.72916 | 54.68 |
| 10 | -5.9517 | 0.4000 | | |
| 11 | ∞ | 1.2308 | 1.49400 | 75.00 |
| 12 | ∞ | 0.0923 | | |
| 13 | 3.0306 | 2.5105 | 1.58913 | 61.14 |
| 14 | -2.8577 | 0.9231 | 1.92286 | 18.90 |
| 15 | -7.6560 | 0.5475 | | |
| 16 | ∞ | 1.0154 | 1.51633 | 64.14 |
| 17 | ∞ | 0.0308 | 1.51300 | 64.00 |
| 18 | ∞ | 1.0770 | 1.50510 | 63.26 |
| 19 | ∞ | 0.0000 | | |
| (Image plane) | | | | |

| Various data | |
|---|---|
| IH | 0.729 |
| ω | 49.996 |
| Fno | 2.489 |
| f | 1 |
| D1 | 3.763 |
| D2 | 1.953 |
| L | 20.57 |
| \|fF\| | 2.707 |
| fR | 3.526 |
| \|f1\| | 3.231 |

Example 27

Unit mm
Surface data

| Surface no. | r | d | nd | vd |
|---|---|---|---|---|
| 1 | ∞ | 0.9372 | 1.88300 | 40.76 |
| 2 | 2.4472 | 1.9660 | | |
| 3 | -1.9633 | 0.7810 | 1.58913 | 61.14 |
| 4 | -22.1376 | 1.0934 | 1.53172 | 48.84 |
| 5 | -3.5969 | 0.0708 | | |
| 6 | ∞ | 5.6232 | 1.51633 | 64.14 |
| 7 | ∞ | 0.0000 | | |
| 8(Stop) | ∞ | 0.5623 | | |
| 9 | 10.4450 | 2.4566 | 1.72916 | 54.68 |
| 10 | -9.4629 | 0.2499 | | |
| 11 | ∞ | 1.2496 | 1.49400 | 75.00 |
| 12 | ∞ | 0.0937 | | |
| 13 | 3.5658 | 2.9714 | 1.58913 | 61.14 |
| 14 | -2.4471 | 0.7810 | 1.92286 | 18.90 |
| 15 | -6.4505 | 1.1303 | | |
| 16 | ∞ | 0.9372 | 1.51633 | 64.14 |
| 17 | ∞ | 0.0312 | 1.51300 | 64.00 |
| 18 | ∞ | 1.0934 | 1.50510 | 63.26 |
| 19 | ∞ | 0.0000 | | |
| (Image plane) | | | | |

| Various data | |
|---|---|
| IH | 0.74 |
| ω | 50.005 |
| Fno | 2.895 |
| f | 1 |
| D1 | 3.779 |
| D2 | 2.495 |
| L | 22.028 |
| \|fF\| | 2.172 |
| fR | 4.01 |
| \|f1\| | 2.772 |

Example 28

Unit mm
Surface data

| Surface no. | r | d | nd | vd |
|---|---|---|---|---|
| 1 | ∞ | 0.9703 | 1.88300 | 40.76 |
| 2 | 1.9374 | 1.9951 | | |
| 3 | −2.7169 | 0.8086 | 1.58913 | 61.14 |
| 4 | −14.7411 | 1.1320 | 1.53172 | 48.84 |
| 5 | −3.4923 | 0.0855 | | |
| 6 | ∞ | 5.8217 | 1.51633 | 64.14 |
| 7 | ∞ | 0.0000 | | |
| 8(Stop) | ∞ | 0.5822 | | |
| 9 | 21.2486 | 2.1947 | 1.72916 | 54.68 |
| 10 | −8.2644 | 0.2587 | | |
| 11 | ∞ | 1.2937 | 1.49400 | 75.00 |
| 12 | ∞ | 0.0970 | | |
| 13 | 4.5944 | 3.4743 | 1.72916 | 54.68 |
| 14 | −2.6083 | 0.8086 | 1.92286 | 18.90 |
| 15 | −10.2363 | 1.1721 | | |
| 16 | ∞ | 0.9703 | 1.51633 | 64.14 |
| 17 | ∞ | 0.0323 | 1.51300 | 64.00 |
| 18 | ∞ | 1.1320 | 1.50510 | 63.26 |
| 19 | ∞ | 0.0000 | | |
| (Image plane) | | | | |

Various data

| | |
|---|---|
| IH | 0.767 |
| ω | 50.001 |
| Fno | 2.851 |
| f | 1 |
| D1 | 3.925 |
| D2 | 2.585 |
| L | 22.829 |
| |fF| | 2.465 |
| fR | 4.099 |
| |f1| | 2.194 |

Example 29

Unit mm
Surface data

| Surface no. | r | d | nd | vd |
|---|---|---|---|---|
| 1 | ∞ | 0.9732 | 1.88300 | 40.76 |
| 2 | 1.9571 | 1.9435 | | |
| 3 | −2.9974 | 0.8110 | 1.58913 | 61.14 |
| 4 | −13.7469 | 1.1355 | 1.53172 | 48.84 |
| 5 | −3.4767 | 0.0935 | | |
| 6 | ∞ | 5.8395 | 1.51633 | 64.14 |
| 7 | ∞ | 0.0000 | | |
| 8(Stop) | ∞ | 0.5839 | | |
| 9 | 55.9845 | 2.7878 | 1.72916 | 54.68 |
| 10 | −7.3251 | 0.2595 | | |
| 11 | ∞ | 1.2977 | 1.49400 | 75.00 |
| 12 | ∞ | 0.0973 | | |
| 13 | 4.6802 | 3.6626 | 1.75500 | 52.32 |
| 14 | −2.6170 | 0.8110 | 1.92286 | 18.90 |
| 15 | −10.9745 | 1.1821 | | |
| 16 | ∞ | 0.9732 | 1.88300 | 40.76 |
| 17 | ∞ | 0.0324 | 1.51300 | 64.00 |
| 18 | ∞ | 1.1355 | 1.50510 | 63.26 |
| 19 | ∞ | 0.0000 | | |
| (Image plane) | | | | |

Various data

| | |
|---|---|
| IH | 0.769 |
| ω | 50 |
| Fno | 2.697 |
| f | 1 |
| D1 | 3.945 |
| D2 | 2.475 |
| L | 23.619 |
| |fF| | 2.721 |
| fR | 4.079 |
| |f1| | 2.216 |

Example 30

Unit mm
Surface data

| Surface no. | r | d | nd | vd |
|---|---|---|---|---|
| 1 | ∞ | 0.9725 | 1.88300 | 40.76 |
| 2 | 1.9111 | 1.9861 | | |
| 3 | −2.9855 | 0.8104 | 1.58913 | 61.14 |
| 4 | −14.5063 | 1.1345 | 1.53172 | 48.84 |
| 5 | −3.5537 | 0.0903 | | |
| 6 | ∞ | 5.8347 | 1.80610 | 40.92 |
| 7 | ∞ | 0.0000 | | |
| 8(Stop) | ∞ | 0.5835 | | |
| 9 | 51.3462 | 2.8547 | 1.72916 | 54.68 |
| 10 | −7.0255 | 0.2593 | | |
| 11 | ∞ | 1.2966 | 1.49400 | 75.00 |
| 12 | ∞ | 0.0972 | | |
| 13 | 4.6055 | 3.5917 | 1.75500 | 52.32 |
| 14 | −2.6216 | 0.8104 | 1.92286 | 18.90 |
| 15 | −11.2717 | 1.1627 | | |
| 16 | ∞ | 0.9725 | 1.88300 | 40.76 |
| 17 | ∞ | 0.0324 | 1.51300 | 64.00 |
| 18 | ∞ | 1.1345 | 1.50510 | 63.26 |
| 19 | ∞ | 0.0000 | | |
| (Image plane) | | | | |

Various data

| | |
|---|---|
| IH | 0.768 |
| ω | 50 |
| Fno | 2.868 |
| f | 1 |
| D1 | 3.321 |
| D2 | 2.454 |
| L | 23.624 |
| |fF| | 2.577 |
| fR | 3.998 |
| |f1| | 2.164 |

Example 31

Unit mm
Surface data

| Surface no. | r | d | nd | vd |
|---|---|---|---|---|
| 1 | ∞ | 0.9226 | 1.51633 | 64.14 |
| 2 | 1.7069 | 1.7909 | | |
| 3 | −2.1879 | 0.7689 | 1.58913 | 61.14 |
| 4 | −23.0503 | 1.0764 | 1.53172 | 48.84 |
| 5 | −3.7068 | 0.1922 | | |
| 6 | ∞ | 5.5357 | 1.51633 | 64.14 |
| 7 | ∞ | 0.0000 | | |
| 8(Stop) | ∞ | 0.5536 | | |
| 9 | 15.9443 | 1.8848 | 1.48749 | 70.23 |
| 10 | −4.1174 | 0.2460 | | |
| 11 | ∞ | 1.2302 | 1.49400 | 75.00 |
| 12 | ∞ | 0.0923 | | |
| 13 | 3.0881 | 2.5677 | 1.58913 | 61.14 |
| 14 | −2.6929 | 0.7689 | 1.92286 | 18.90 |
| 15 | −7.3328 | 0.7351 | | |
| 16 | ∞ | 0.9226 | 1.51633 | 64.14 |
| 17 | ∞ | 0.0308 | 1.51300 | 64.00 |

-continued

| | | | | |
|---|---|---|---|---|
| 18 | ∞ | 1.0764 | 1.50510 | 63.26 |
| 19 | ∞ | 0.0000 | | |
| (Image plane) | | | | |

Various data

| | |
|---|---|
| IH | 0.729 |
| ω | 50 |
| Fno | 2.968 |
| f | 1 |
| D1 | 3.843 |
| D2 | 2.079 |
| L | 20.395 |
| \|fF\| | 2.702 |
| fR | 3.528 |
| \|f1\| | 3.306 |

Example 32

Unit mm
Surface data

| Surface no. | r | d | nd | vd |
|---|---|---|---|---|
| 1 | ∞ | 0.9737 | 1.88300 | 40.76 |
| 2 | 1.9496 | 1.7057 | | |
| 3 | −4.0191 | 0.8114 | 1.58913 | 61.14 |
| 4 | 8.4542 | 1.3523 | 1.59551 | 39.24 |
| 5 | −4.9365 | 0.0951 | | |
| 6 | ∞ | 5.8420 | 1.88300 | 40.76 |
| 7 | ∞ | 0.0000 | | |
| 8(Stop) | ∞ | 0.5842 | | |
| 9 | 67.4510 | 2.5304 | 1.71700 | 47.92 |
| 10 | −6.2916 | 0.2596 | | |
| 11 | ∞ | 1.2982 | 1.49400 | 75.00 |
| 12 | ∞ | 0.0974 | | |
| 13 | 3.9748 | 2.8533 | 1.72916 | 54.68 |
| 14 | −2.6289 | 0.9737 | 1.92286 | 18.90 |
| 15 | −11.2155 | 1.0871 | | |
| 16 | ∞ | 0.9737 | 1.88300 | 40.76 |
| 17 | ∞ | 0.0325 | 1.51300 | 64.00 |
| 18 | ∞ | 1.1359 | 1.50510 | 63.26 |
| 19 | ∞ | 0.0000 | | |
| (Image plane) | | | | |

Various data

| | |
|---|---|
| IH | 0.769 |
| ω | 50 |
| Fno | 2.789 |
| f | 1 |
| D1 | 3.198 |
| D2 | 2.38 |
| L | 22.606 |
| \|fF\| | 2.627 |
| fR | 3.722 |
| \|f1\| | 2.208 |

Example 33

Unit mm
Surface data

| Surface no. | r | d | nd | vd |
|---|---|---|---|---|
| 1 | ∞ | 0.5611 | 1.88300 | 40.76 |
| 2 | 1.4627 | 0.7714 | | |
| 3 | ∞ | 1.2157 | 1.74077 | 27.79 |
| 4 | −7.7008 | 0.2806 | | |
| 5 | ∞ | 3.3666 | 1.51633 | 64.14 |
| 6 | ∞ | 0.0000 | | |
| 7(Stop) | ∞ | 0.3367 | | |
| 8 | 10.1391 | 0.8213 | 1.61405 | 54.99 |
| 9 | −3.0652 | 0.1046 | | |
| 10 | ∞ | 0.7481 | 1.49400 | 75.00 |
| 11 | ∞ | 0.1870 | | |
| 12 | 1.7777 | 1.5695 | 1.51633 | 64.14 |
| 13 | −1.8580 | 0.5611 | 1.92286 | 18.90 |
| 14 | −11.7188 | 0.5528 | | |
| 15 | ∞ | 0.5611 | 1.51633 | 64.14 |
| 16 | ∞ | 0.0187 | 1.51300 | 64.00 |
| 17 | ∞ | 0.6546 | 1.50510 | 63.26 |
| 18 | ∞ | 0.0000 | | |
| (Image plane) | | | | |

Various data

| | |
|---|---|
| IH | 0.756 |
| ω | 49.904 |
| Fno | 2.764 |
| f | 1 |
| D1 | 2.501 |
| D2 | 1.37 |
| L | 12.311 |
| \|fF\| | 2.369 |
| fR | 2.327 |
| \|f1\| | 1.657 |
| vd (L2) | 27.79 |

Next, values of conditional expressions in each example are given below. '-' (hyphen) indicates that there is no corresponding arrangement.

| | Example1 | Example2 | Example3 | Example4 |
|---|---|---|---|---|
| (1)D1/f | 1.866 | 2.021 | 2.31 | 2.205 |
| (2)D2/f | 1.278 | 1.453 | 1.437 | 1.439 |
| (3)L/f | 11.268 | 12.398 | 12.37 | 12.098 |
| (4)D1/D2 | 1.46 | 1.391 | 1.608 | 1.533 |
| (5)\|fF/f\| | 2.43 | 2 | 2.003 | 2.359 |
| (6)fR/f | 2.149 | 2.476 | 2.473 | 2.469 |
| (7)\|f1/f\| | 1.494 | 1.393 | 1.461 | 1.569 |
| (8)\|f1/f2\| | 0.196 | 0.101 | 0.087 | 0.138 |
| (9)\|nd (L2f) − nd(L2b)\| | — | — | — | — |

| | Example5 | Example6 | Example7 | Example8 |
|---|---|---|---|---|
| (1)D1/f | 2.547 | 2.482 | 2.501 | 2.159 |
| (2)D2/f | 1.573 | 1.453 | 1.466 | 1.48 |
| (3)L/f | 13.184 | 12.402 | 12.446 | 12.404 |
| (4)D1/D2 | 1.62 | 1.709 | 1.707 | 1.458 |
| (5)\|fF/f\| | 2.341 | 2.535 | 2.4 | 2.407 |
| (6)fR/f | 2.622 | 2.406 | 2.376 | 2.336 |
| (7)\|f1/f\| | 1.683 | 1.695 | 1.679 | 1.615 |

-continued

|  | | | | |
|---|---|---|---|---|
| (8)\|f1/f2\| | 0.113 | 0.17 | 0.157 | 0.166 |
| (9)\|nd (L2f) − nd(L2b)\| | — | — | — | — |

|  | Example9 | Example10 | Example11 | Example12 |
|---|---|---|---|---|
| (1)D1/f | 2.084 | 2.799 | 3.02 | 2.58 |
| (2)D2/f | 1.428 | 1.571 | 1.532 | 1.459 |
| (3)L/f | 12.388 | 14.95 | 15.985 | 16.065 |
| (4)D1/D2 | 1.459 | 1.781 | 1.971 | 1.769 |
| (5)\|fF/f\| | 2.495 | 2.481 | 2.59 | 2.522 |
| (6)fR/f | 2.307 | 2.805 | 2.907 | 2.839 |
| (7)\|f1/f\| | 1.609 | 1.902 | 2.007 | 1.938 |
| (8)\|f1/f2\| | 0.179 | 0.078 | 0.073 | 0.075 |
| (9)\|nd (L2f) − nd(L2b)\| | — | — | — | — |

|  | Example13 | Example14 | Example15 | Example16 |
|---|---|---|---|---|
| (1)D1/f | 3.275 | 3.31 | 3.353 | 3.202 |
| (2)D2/f | 2.099 | 2.175 | 2.32 | 2.333 |
| (3)L/f | 21.011 | 21.502 | 21.825 | 22.254 |
| (4)D1/D2 | 1.56 | 1.522 | 1.445 | 1.373 |
| (5)\|fF/f\| | 4.01 | 3.788 | 3.528 | 2.968 |
| (6)fR/f | 3.668 | 3.754 | 3.874 | 3.737 |
| (7)\|f1/f\| | 2.03 | 1.947 | 1.757 | 2.075 |
| (8)\|f1/f2\| | 0.122 | 0.107 | 0.114 | 0.049 |
| (9)\|nd (L2f) − nd(L2b)\| | 0.05741 | 0.05741 | 0.05741 | 0.00769 |

|  | Example17 | Example18 | Example19 | Example20 |
|---|---|---|---|---|
| (1)D1/f | 3.652 | 4.161 | 4.088 | 1.864 |
| (2)D2/f | 2.245 | 2.418 | 2.678 | 1.366 |
| (3)L/f | 24.792 | 26.589 | 27.922 | 11.83 |
| (4)D1/D2 | 1.626 | 1.721 | 1.527 | 1.365 |
| (5)\|fF/f\| | 3.419 | 3.424 | 3.206 | 2.225 |
| (6)fR/f | 4.327 | 4.491 | 4.737 | 2.293 |
| (7)\|f1/f\| | 1.902 | 2.11 | 2.139 | 2.134 |
| (8)\|f1/f2\| | 0.081 | 0.062 | 0.038 | 0.038 |
| (9)\|nd (L2f) − nd(L2b)\| | 0.04099 | 0.04099 | 0.04099 | — |

|  | Example21 | Example22 | Example23 | Example24 |
|---|---|---|---|---|
| (1)D1/f | 2.135 | 2.497 | 2.489 | 4.284 |
| (2)D2/f | 1.337 | 1.544 | 1.529 | 3.011 |
| (3)L/f | 11.672 | 12.511 | 12.436 | 23.513 |
| (4)D1/D2 | 1.597 | 1.617 | 1.628 | 1.423 |
| (5)\|fF/f\| | 2.405 | 2.538 | 2.607 | 1.847 |
| (6)fR/f | 2.356 | 2.458 | 2.434 | 4.107 |
| (7)\|f1/f\| | 2.249 | 2.236 | 2.355 | 4.025 |
| (8)\|f1/f2\| | 0.025 | 0.012 | 0.009 | 0.786 |
| (9)\|nd (L2f) − nd(L2b)\| | — | — | — | — |

|  | Example25 | Example26 | Example27 | Example28 |
|---|---|---|---|---|
| (1)D1/f | 2.726 | 3.763 | 3.779 | 3.925 |
| (2)D2/f | 1.791 | 1.953 | 2.495 | 2.585 |
| (3)L/f | 14.838 | 20.57 | 22.028 | 22.829 |
| (4)D1/D2 | 1.522 | 1.927 | 1.514 | 1.518 |
| (5)\|fF/f\| | 2.38 | 2.707 | 2.172 | 2.465 |
| (6)fR/f | 2.781 | 3.526 | 4.01 | 4.099 |
| (7)\|f1/f\| | 2.734 | 3.231 | 2.772 | 2.194 |
| (8)\|f1/f2\| | 0.145 | 0.231 | 0.266 | 0.043 |
| (9)\|nd (L2f) − nd(L2b)\| | — | 0.05741 | 0.05741 | 0.05741 |

|  | Example29 | Example30 | Example31 | Example32 |
|---|---|---|---|---|
| (1)D1/f | 3.945 | 3.321 | 3.843 | 3.198 |
| (2)D2/f | 2.475 | 2.454 | 2.079 | 2.38 |
| (3)L/f | 23.619 | 23.624 | 20.395 | 22.606 |
| (4)D1/D2 | 1.594 | 1.353 | 1.848 | 1.343 |
| (5)\|fF/f\| | 2.721 | 2.577 | 2.702 | 2.627 |
| (6)fR/f | 4.079 | 3.998 | 3.528 | 3.722 |
| (7)\|f1/f\| | 2.216 | 2.164 | 3.306 | 2.208 |
| (8)\|f1/f2\| | 0.004 | 0.015 | 0.256 | 0.003 |
| (9)\|nd (L2f) − nd(L2b)\| | 0.05741 | 0.05741 | 0.05741 | 0.00638 |

|  | Example33 |
|---|---|
| (1)D1/f | 2.501 |
| (2)D2/f | 1.37 |

-continued

| | |
|---|---|
| (3)L/f | 12.311 |
| (4)D1/D2 | 1.825 |
| (5)\|fF/f\| | 2.369 |
| (6)fR/f | 2.327 |
| (7)\|f1/f\| | 1.657 |
| (8)\|f1/f2\| | 0.159 |
| (9)\|nd (L2f) − nd(L2b)\| | — |

Figure 38:
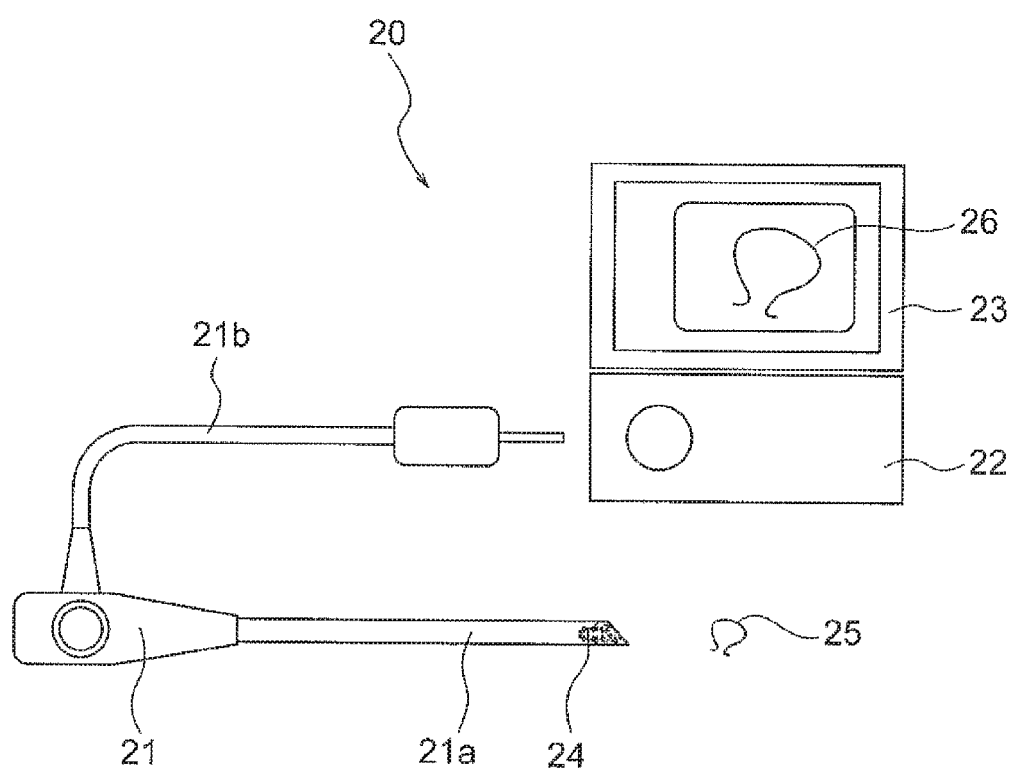
FIG. 38 is a diagram showing an arrangement of an endoscope apparatus.

FIG. 38 is an example of an arrangement of an endoscope apparatus in which the oblique-viewing objective optical system of the present embodiment is used. An endoscope apparatus 20 includes an endoscope for oblique viewing 21 (hereinafter, referred to as the 'endoscope 21'), a video processor 22, and a monitor 23. The endoscope 21 includes an inserting portion 21a and a signal cable 21b. An oblique-viewing objective optical system 24 is disposed at a front end of the inserting portion 21a. In this case, the oblique-viewing objective optical system 24 is an oblique-viewing objective optical system for front-view observation. Any one of the oblique-viewing objective optical systems according to the examples 1 to 33 is to be used as the oblique-viewing objective optical system 24.

Moreover, although it is not shown in the diagram, an illumination optical system which illuminates an object 25 is disposed near the oblique-viewing objective optical system 24. The illumination optical system includes a light source, an illumination optical element, and an optical fiber bundle. As the light source, light emitting elements such as a light-emitting diode (LED: Light Emitting Diode) and a laser diode (LD: Laser Diode) are available. As the illumination optical element, a lens element is available. A lens element has a function of diffusing or focusing illumination light. The optical fiber bundle transmits the illumination light to the endoscope 21.

Moreover, the endoscope 21 is connected to the video processor 22 via the signal cable 21b. An image of the object 25 formed by the oblique-viewing objective optical system 24 is captured by the image pickup element. The image of the object 25 that has been captured is converted to a video signal by an electric-circuit system built-in in the video processor 22. Based on the video signal, a video picture 26 is displayed on the monitor 23.

An electric circuit system which drives the light source such as an LED is provided to an interior of the video processor 22.

Moreover, by providing a light-emitting element such as an LED and LD inside the endoscope 21, there is no need to provide a light source outside the endoscope 21. Furthermore, by providing these light-emitting elements to a front-end portion of the endoscope 21, there is no need to provide the optical fiber bundle that transmits the illumination light.

Furthermore, a lamp such as a xenon lamp or a halogen lamp may be used as the light source. Moreover, in the endoscope apparatus 20, a light-source unit having a built-in light source may be integrated with the video processor 22. However, the light-source unit may be arranged separately from the video processor 22. In this case, the light-source unit and the video processor 22 are to be connected separately to the endoscope 21.

As described above, according to the oblique-viewing objective optical system of the present invention, it is possible to provide an oblique-viewing objective optical system having a high performance and a small size, and which is appropriate for an image pickup element with a large number of pixels and small size. Furthermore, by using the oblique-viewing objective optical system of the present invention, it is possible to provide an endoscope for oblique viewing in which a high-quality image is achieved, and which has a front-end portion having a thinned diameter.

Various embodiments of the present invention have been described heretofore. However, the present invention is not limited only to the embodiments described above, and embodiments in which arrangements of these embodiments have been combined appropriately without departing from the scope of the invention are also within the scope of the present invention.

(Appended Mode)

The present invention also includes the following inventions which are conceived form abovementioned embodiments and examples.

(Appended Mode 1)

An oblique-viewing objective optical system, comprising in order from an object side:

a front-side lens group having a negative refractive power;

an optical path converting element;

an aperture stop; and a rear-side lens group having a positive refractive power, wherein the front-side lens group includes a first lens and a second lens, and the rear-side lens group includes a third lens and a cemented lens having a positive refractive power, and the first lens is a negative lens having a concave surface directed toward an image-plane side, and the second lens is a single lens having a convex surface directed toward the image-plane side or a cemented lens, and the third lens is a positive lens, and the cemented lens includes a positive lens which is a biconvex lens, and a negative lens having a meniscus shape, and the following conditional expressions (1) to (3) are satisfied:

$$1.6 < D1/f < 4.7 \quad (1),$$

$$1.0 < D2/f < 3.3 \quad (2), \text{ and}$$

$$9.0 < L/f < 31.0 \quad (3)$$

where,

D1 denotes an air-conversion length from an image-side surface of a lens positioned nearest to an image plane in the front-side lens group up to the aperture stop, D2 denotes an air-conversion length from an image-side surface of a rearmost lens in the rear-side lens group up to an image plane, L denotes an overall length of the oblique-viewing objective optical system, and f denotes a focal length of the overall oblique-viewing objective optical system.

(Appended Mode 2)

The oblique-viewing objective optical system according to Appended Mode 1, wherein the following conditional expression (4) is satisfied:

$$1.0<D1/D2<2.5 \quad (4)$$

where,

D1 denotes the air-conversion length from the image-side surface of the lens positioned nearest to the image plane in the front-side lens group up to the aperture stop, and D2 denotes the air-conversion length from the image-side surface of the rearmost lens in the rear-side lens group up to the image plane.

(Appended Mode 3)

The oblique-viewing objective optical system according to Appended Mode 2, wherein the following conditional expressions (5) and (6) are satisfied:

$$1.6<|fF/f|<4.5 \quad (5), \text{ and}$$

$$1.9<fR/f<5.3 \quad (6)$$

where, fF denotes a focal length of the front-side lens group, fR denotes a focal length of the rear-side lens group, and f denotes the focal length of the overall oblique-viewing objective optical system.

(Appended Mode 4)

The oblique-viewing objective optical system according to Appended Mode 2, wherein the following conditional expressions (7) and (8) are satisfied:

$$1.2<|f1/f|<4.5 \quad (7), \text{ and}$$

$$0.001<|f1/f2|<0.9 \quad (8)$$

where, f1 denotes a focal length of the first lens, f2 denotes a focal length of the second lens, and f denotes the focal length of the overall oblique-viewing objective optical system.

(Appended Mode 5)

The oblique-viewing objective optical system according to Appended Mode 4, wherein the second lens has a positive refractive power, and the following conditional expression (7') is satisfied:

$$1.2<|f1/f|<2.4 \quad (7')$$

where, f1 denotes the focal length of the first lens, and f denotes the focal length of the overall oblique-viewing objective optical system.

(Appended Mode 6)

The oblique-viewing objective optical system according to Appended Mode 4, wherein the second lens has a negative refractive power, and the following conditional expression (7") is satisfied:

$$1.9<|f1/f|<4.5 \quad (7")$$

where, f1 denotes the focal length of the first lens, and f denotes the focal length of the overall oblique-viewing objective optical system.

(Appended Mode 7)

The oblique-viewing objective optical system according to Appended Mode 4, wherein the second lens has a positive refractive power, and the following conditional expression (8') is satisfied $$0.02<|f1/f2|<0.22 \quad (8')$$

where, f1 denotes the focal length of the first lens, and f2 denotes the focal length of the second lens.

(Appended Mode 8)

The oblique-viewing objective optical system according to Appended Mode 1, wherein the second lens is a cemented lens, and the following conditional expression (9) is satisfied $$|nd(L2f)-nd(L2b)|\leq 0.1 \quad (9)$$

where, nd (L2f) denotes a refractive index of an object-side lens in the cemented lens of the second lens, and nd (L2b) denotes a refractive index of an image-plane side lens in the cemented lens of the second lens.

(Appended Mode 9)

An endoscope for oblique-viewing, comprising:

the oblique-viewing objective optical system according to any one of Appended Mode s 1 to 8.

According to the present invention, it is possible to realize an oblique-viewing objective optical system having a high performance and a small size. Moreover, it is possible to provide an endoscope for oblique viewing in which a high-quality image is achieved, and which has a front-end portion having a thinned diameter.

In such manner, the present invention is useful for an oblique-viewing objective optical system having a high performance and a small size. Moreover, the present invention is useful for an endoscope for oblique viewing in which a high-quality image is achieved, and which has a front-end portion having a thinned diameter.

What is claimed is:

1. An oblique-viewing objective optical system, comprising in order from an object side:

a front-side lens group having a negative refractive power;

an optical path converting element;

an aperture stop; and a rear-side lens group having a positive refractive power, wherein the front-side lens group includes a first lens and a second lens, and the rear-side lens group includes a third lens and a cemented lens having a positive refractive power, and the first lens is a negative lens having a concave surface directed toward an image-plane side, and the second lens is a single lens having a convex surface directed toward the image-plane side or a cemented lens, and the third lens is a positive lens, and the cemented lens in the rear-side lens group includes a positive lens which is a biconvex lens, and a negative lens having a meniscus shape, and the following conditional expressions (1) to (3) are satisfied:

$$1.6<D1/f<4.7 \quad (1),$$

$$1.0<D2/f<3.3 \quad (2), \text{ and}$$

$$9.0<L/f<31.0 \quad (3)$$

where,

D1 denotes an air-conversion length from an image-side surface of a lens positioned nearest to an image plane in the front-side lens group up to the aperture stop, D2 denotes an air-conversion length from an image-side surface of a rearmost lens in the rear-side lens group up to an image plane, L denotes an overall length of the oblique-viewing objective optical system, and f denotes a focal length of the overall oblique-viewing objective optical system.

2. The oblique-viewing objective optical system according to claim 1, wherein the following conditional expression (4) is satisfied:

$$1.0 < D1/D2 < 2.5 \quad (4)$$

where,

D1 denotes the air-conversion length from the image-side surface of the lens positioned nearest to the image plane in the front-side lens group up to the aperture stop, and D2 denotes the air-conversion length from the image-side surface of the rearmost lens in the rear-side lens group up to the image plane.

3. The oblique-viewing objective optical system according to claim 2, wherein the following conditional expressions (5) and (6) are satisfied:

$$1.6 < |fF/f| < 4.5 \quad (5), \text{ and}$$

$$1.9 < fR/f < 5.3 \quad (6)$$

where, fF denotes a focal length of the front-side lens group, fR denotes a focal length of the rear-side lens group, and f denotes the focal length of the overall oblique-viewing objective optical system.

4. The oblique-viewing objective optical system according to claim 2, wherein the following conditional expressions (7) and (8) are satisfied:

$$1.2 < |f1/f| < 4.5 \quad (7), \text{ and}$$

$$0.001 < |f1/f2| < 0.9 \quad (8)$$

where, f1 denotes a focal length of the first lens, f2 denotes a focal length of the second lens, and f denotes the focal length of the overall oblique-viewing objective optical system.

5. The oblique-viewing objective optical system according to claim 4, wherein the second lens has a positive refractive power, and the following conditional expression (7') is satisfied:

$$1.2 < |f1/f| < 2.4 \quad (7')$$

where, f1 denotes the focal length of the first lens, and f denotes the focal length of the overall oblique-viewing objective optical system.

6. The oblique-viewing objective optical system according to claim 4, wherein the second lens has a negative refractive power, and the following conditional expression (7") is satisfied:

$$1.9 < |f1/f| < 4.5 \quad (7")$$

where, f1 denotes the focal length of the first lens, and f denotes the focal length of the overall oblique-viewing objective optical system.

7. The oblique-viewing objective optical system according to claim 4, wherein the second lens has a positive refractive power, and the following conditional expression (8') is satisfied $$0.02 < |f1/f2| < 0.22 \quad (8')$$

where, f1 denotes the focal length of the first lens, and f2 denotes the focal length of the second lens.

8. The oblique-viewing objective optical system according to claim 1, wherein the second lens is a cemented lens, and the following conditional expression (9) is satisfied $$|nd(L2f) - nd(L2b)| \le 0.1 \quad (9)$$

where, nd (L2f) denotes a refractive index of an object-side lens in the cemented lens of the second lens, and nd (L2b) denotes a refractive index of an image-plane side lens in the cemented lens of the second lens.

9. An endoscope for oblique-viewing, comprising:

the oblique-viewing objective optical system according to claim 1.

* * * * *

UNITED STATES PATENT AND TRADEMARK OFFICE
CERTIFICATE OF CORRECTION

PATENT NO. : 9,933,610 B2
APPLICATION NO. : 15/719499
DATED : April 3, 2018
INVENTOR(S) : Yoshiharu Takasugi Page 1 of 1

It is certified that error appears in the above-identified patent and that said Letters Patent is hereby corrected as shown below:

In the Specification

Column 2, Line 43, delete "system." and insert --system--.

Column 6, Line 55, after "23" insert --;--.

Column 9, Line 38, delete "carryout" and insert --carry out--.

Column 22, Line 9, delete "g." and insert --FIG.--.

Column 47, Line 3, delete "co" and insert --ω--.

Column 55, Line 27, delete "0.796" and insert --0.769--.

Column 56, Line 22, delete "6 ∞ 5.8579" and insert --6 ∞ 5.8579 1.88300 40.76--.

Column 56, Line 53, delete "1.9763" and insert --1.0922--.

Column 56, Line 54, delete "1.6796" and insert --1.6793--.

Column 59, Line 7, delete "1.15633" and insert --1.51633--.

Column 59, Line 13, delete "0.2686" and insert --0.2986--.

Column 59, Line 20, delete "1.15300" and insert --1.51300--.

Column 72, Line 19, delete "Mode s" and insert --Modes--.

Signed and Sealed this
Ninth Day of October, 2018

Andrei Iancu
*Director of the United States Patent and Trademark Office*